(12) United States Patent
Brown, III et al.

(10) Patent No.: US 10,221,446 B1
(45) Date of Patent: *Mar. 5, 2019

(54) SIGNAL PROPAGATION BIOMOLECULES, DEVICES AND METHODS

(71) Applicants: Carl Brown, III, Albuquerque, NM (US); Steven Wayde Graves, Santa Fe, NM (US); Darko Stefanovic, Albuquerque, NM (US); Matthew Richard Lakin, Albuquerque, NM (US)

(72) Inventors: Carl Brown, III, Albuquerque, NM (US); Steven Wayde Graves, Santa Fe, NM (US); Darko Stefanovic, Albuquerque, NM (US); Matthew Richard Lakin, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,594

(22) Filed: Oct. 3, 2016

Related U.S. Application Data

(63) Continuation of application No. 14/283,993, filed on May 21, 2014, now Pat. No. 9,476,090.

(60) Provisional application No. 61/825,738, filed on May 21, 2013, provisional application No. 61/861,600, filed on Aug. 2, 2013.

(51) Int. Cl.
*C12Q 1/68* (2018.01)
*C12Q 1/6818* (2018.01)
*C07H 21/02* (2006.01)
*C07H 21/04* (2006.01)

(52) U.S. Cl.
CPC .................. *C12Q 1/6818* (2013.01)

(58) Field of Classification Search
None
See application file for complete search history.

(56) References Cited

U.S. PATENT DOCUMENTS

2013/0071839 A1* 3/2013 Seelig .................. C12O 1/6876
435/6.11

OTHER PUBLICATIONS

Macdonald et al., "Solution-Phase Molecular-Scale Computation With Deoxyribozyme-Based Logic Gates and Fluorescent Readouts" 335 Method in Molecular Biology 343-363 (2006).*
Shlyahovsky et al., "Logic Gates and Antisense DNA Devices Operating on a Translator Nucleic Acid Scaffold" 3(7) ACS Nano 1831-1843 (2009).*
Noguera et al., "Carbon nanoparticles in lateral flow methods to detect genes encoding virulence factors of Shiga toxin-producing *Escherichia coli*" 399 Analytical and Bioanalytical Chemistry 831-838 (2011).*

* cited by examiner

*Primary Examiner* — Nancy J Leith
(74) *Attorney, Agent, or Firm* — Gonzales Patent Services; Ellen M. Gonzales

(57) ABSTRACT

This disclosure describes a structured polynucleotide, devices that include the structured polynucleotide, and methods involving the structured polynucleotide and/or devices. Generally, the structured polynucleotide includes five domains. A first domain acts as a toehold for an input DNA logic gate to initiate binding to an SCS biomolecule. A second domain acts as a substrate recognition sequence for an upstream DNA logic gate. A third domain acts as a toehold for a output DNA logic gate to initiate binding of the SCS biomolecule to the gate. A fourth domain acts as an effector sequence to alter the state of the output logic gate. A fifth domain acts as a cage sequence to lock the effector sequence in an inactive state until an input gate binds to the structured polynucleotide.

19 Claims, 42 Drawing Sheets
(41 of 42 Drawing Sheet(s) Filed in Color)

Specification includes a Sequence Listing.

Fig. 3

D)
Table 1

| Strand | Sequence | Conc. (nM) | SEQ ID NO: |
|---|---|---|---|
| Input | GCCGGTCGAA AACTAAGA TACAT | 100 | 1 |
| DNAzyme (Dz) | GAACTATC TCCGAGCCGGTCGAA AACTAAGA | 100 | 2 |
| Inhibitor (Inh) | ATGTA TCTTAGTT TTCGACCGGC | 125 | 3 |
| Substrate | FAM-TCTTAGTT rAG GATAGTTC AT-TAM | 250 | 4 |

Table 2

| Strand | Sequence | Conc. (nM) | SEQ ID NO: |
|---|---|---|---|
| Input | ATGTA TCTTAGTT TTCGACCGGC | 125 | 5 |
| DNAzyme (Dz) | GAACTATC TCCGAGCCGGTCGAA AACTAAGA | 100 | 6 |
| Substrate | FAM-TCTTAGTT rAG GATAGTTC AT-TAM | 250 | 7 |

Table 3

| Strand | Sequence | Conc. (nM) | SEQ ID NO: |
|---|---|---|---|
| Input$_1$ | CGGTCGAA AACTAAGA TGGAG | 100 | 8 |
| Input$_2$ | GACCT GAACTATC TCCGAGC | 100 | 9 |
| DNAzyme (Dz) | GAACTATC TCCGAGCCGGTCGAA AACTAAGA | 100 | 10 |
| Inhibitor (Inh) | CTCCA TCTTAGTT TTCGACCGGCTCGGA GATAGTTC AGGTC | 125 | 11 |
| Substrate | FAM-TCTTAGTT rAG GATAGTTC AT-TAM | 250 | 12 |

*Figure 4*

D)
Table 4

| Strand | Sequence | Conc. (nM) | SEQ ID NO: |
|---|---|---|---|
| Input$_1$ | AACTAAGA TGATGTGGAG | 100 | 13 |
| Input$_2$ | GAGGTTGATG GAACTATC | 100 | 14 |
| DNAzyme (Dz) | GAACTATC TCCGAGCCGGTCGAA AACTAAGA | 100 | 15 |
| Inhibitor (Inh), n=0 | CTCCACATCA TCTTAGTT TTCGACCGGCTCGGA GATAGTTC CATCAACCTC | 125 | 16 |
| Inhibitor (Inh), n=1 | CTCCACATCA TCTTAGTT TTCGACCAGCTCGGA GATAGTTC CATCAACCTC | 125 | 17 |
| Inhibitor (Inh), n=2 | CTCCACATCA TCTTAGTT TTCAACCGGCTAGGA GATAGTTC CATCAACCTC | 125 | 18 |
| Inhibitor (Inh), n=3 | CTCCACATCA TCTTAGTT TTCAACCAGCTAGGA GATAGTTC CATCAACCTC | 125 | 19 |
| Substrate | FAM-TCTTAGTT rAG GATAGTTC AT-TAM | 50 | 20 |

*Fig. 5*

A) Out = (In₁ AND In₂) OR (NOT In₃)

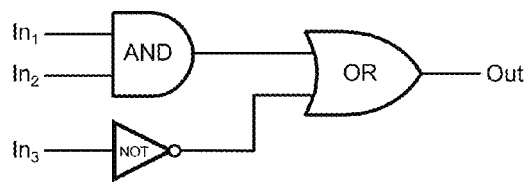

B)

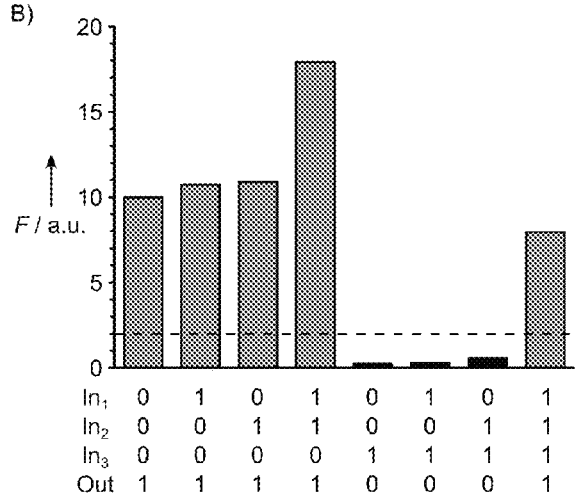

C)
Table 5

| Strand | Sequence | Conc. (nM) | SEQ ID NO: |
|---|---|---|---|
| Input₁ | AACTAAGA TGATGTGGAG | 100 | 21 |
| Input₂ | GAGGTTGATG GAACTATC | 100 | 22 |
| DNAzyme AND gate strand | GAACTATC TCCGAGCCGGTCGAA AACTAAGA | 100 | 23 |
| Inhibitor for AND gate | CTCCACATCA TCTTAGTT TTCAACCAGCTAGGA GATAGTTC CATCAACCTC | 125 | 24 |
| Substrate for AND gate | FAM-TCTTAGTT rAG GATAGTTC AT-TAM | 50 | 25 |
| Input₃ | CGGCTCGGA TCTATCCA CATTC | 125 | 26 |
| DNAzyme NOT gate strand | TGGATAGA TCCGAGCCGGTCGAA AACTAAGA | 100 | 27 |
| Substrate for NOT gate | FAM-TCTTAGTT rAG TCTATCCA AT-TAM | 50 | 28 |

Table 12

| Strand (D1v1) | Sequence | Conc (nM) | SEQ ID NO: |
|---|---|---|---|
| Dz | GAACTATCTCCGAGCCGGTCGAAAACTAAGA | 100 | 109 |
| INH | CTCCATCTTAGTTTTCGACCGGCT | 120 | 110 |
| SCS | CTCCATCTTAGTTGGGTATTrAGCCGGACAGCCGGTCGAAAACTAAGATGGAG | 100 | 111 |
| UE | GTCCGCTCCGAGCCGGTCGAAAATACCC | 100 | 112 |
| Substrate | FAM-TCTTAGTTrAGGATAGTTCAT-TAM | 50 | 113 |

Table 13

| Strand (D1v2) | Sequence | Conc (nM) | SEQ ID NO: |
|---|---|---|---|
| Dz | GAACTATCTCCGAGCCGGTCGAAAACTAAGA | 100 | 114 |
| INH | CTCCATCTTCGTTTTCGACCGGCT | 120 | 115 |
| SCS | CTCCATCTTCGTTGGGTATTrAGCCGGACAGCCGGTCGAAAACGAAGATGGAG | 100 | 116 |
| UE | GTCCGCTCCGAGCCGGTCGAAAATACCC | 100 | 117 |
| Substrate | FAM-TCTTAGTTrAGGATAGTTCAT-TAM | 50 | 118 |

Table 14

| Strand (D1v3) | Sequence | Conc (nM) | SEQ ID NO: |
|---|---|---|---|
| Dz | GAACTATCTCCGAGCCGGTCGAAAACTAAGA | 100 | 119 |
| INH | CTCCATCTTAGTTTTCGACCGGCT | 120 | 120 |
| SCS | CTCCATCTTAGTTTGGGTATTrAGCCGGACAGCCGGTCGAAAACTAAGATGGAG | 100 | 121 |
| UE | GTCCGCTCCGAGCCGGTCGAAAATACCC | 100 | 122 |
| Substrate | FAM-TCTTAGTTrAGGATAGTTCAT-TAM | 50 | 123 |

Table 15

| Strand (D1v4) | Sequence | Conc (nM) | SEQ ID NO: |
|---|---|---|---|
| Dz | GAACTATCTCCGAGCCGGTCGAAAACTAAGA | 100 | 124 |
| INH | CTCCATCTTAGTTTTCGACCGGCT | 120 | 125 |
| SCS | CTCCATCTTAGTTTTGGGTATTrAGCCGGACAGCCGGTCGAAAACTAAGATGGAG | 100 | 126 |
| UE | GTCCGCTCCGAGCCGGTCGAAAATACCC | 100 | 127 |
| Substrate | FAM-TCTTAGTTrAGGATAGTTCAT-TAM | 50 | 128 |

*Figure 11* C) (continued)

Table 16

| Strand (D1v5) | Sequence | Conc (nM) | SEQ ID NO: |
|---|---|---|---|
| Dz | GAACTATCTCCGAGCCGGTCGAAAACTAAGA | 100 | 129 |
| INH | CTCCATCTTAGTTTTCGACCGGCT | 120 | 130 |
| SCS | CTCCATCTTAGTTTTCGAGGGTATrAGGCGGACAGCCGGTCGAAAACTAAGATGGAG | 100 | 131 |
| UE | GTCCGCTCCGAGCCGGTCGAAAATACCC | 100 | 132 |
| Substrate | FAM-TCTTAGTTrAGGATAGTTCAT-TAM | 50 | 133 |

Table 17

| Strand (D1v6) | Sequence | Conc (nM) | SEQ ID NO: |
|---|---|---|---|
| Dz | GAACTATCTCCGAGCCGGTCGAAAACTAAGA | 100 | 134 |
| INH | CTCCATCTTAGTTTTCGACCGGCT | 120 | 135 |
| SCS | CTCCATCTAAGTTTTCGGGTATrAGGCGGACAGCCGGTCGAAAACTAAGATGGAG | 100 | 136 |
| UE | GTCCGCTCCGAGCCGGTCGAAAATACCC | 100 | 137 |
| Substrate | FAM-TCTTAGTTrAGGATAGTTCAT-TAM | 50 | 138 |

Table 18

| Strand (D1v7) | Sequence | Conc (nM) | SEQ ID NO: |
|---|---|---|---|
| Dz | GAACTATCTCCGAGCCGGTCGAAAACTAAGA | 100 | 139 |
| INH | CTCCATCTTAGTTTTCGACCGGCT | 120 | 140 |
| SCS | CTCCATCTTAGTTTTCGAGGGTATrAGGCGGACAGCCGGTCGAAAACTAAGATGGAG | 100 | 141 |
| UE | GTCCGCTCCGAGCCGGTCGAAAATACCC | 100 | 142 |
| Substrate | FAM-TCTTAGTTrAGGATAGTTCAT-TAM | 50 | 143 |

Table 19

| Strand (D1v8) | Sequence | Conc (nM) | SEQ ID NO: |
|---|---|---|---|
| Dz | GAACTATCTCCGAGCCGGTCGAAAACTAAGA | 100 | 144 |
| INH | CTCCATCTTAGTTTTCGACCGGCT | 120 | 145 |
| SCS | CTCCATCTAAGTTTTCGAGGGTATrAGGCGGACAGCCGGTCGAAAACTAAGATGGAG | 100 | 146 |
| UE | GTCCGCTCCGAGCCGGTCGAAAATACCC | 100 | 147 |
| Substrate | FAM-TCTTAGTTrAGGATAGTTCAT-TAM | 50 | 148 |

Table 20

| Strand (D1v4) | Sequence | Conc (nM) | SEQ ID NO: |
|---|---|---|---|
| Dz | GAACTATCTCCGAGCCGGTCGAAAACTAAGA | 100 | 149 |
| INH | CTCCATCTTAGTTTTCGACCGGCT | 120 | 150 |
| SCS | AGCCGGTCGAAAACTAAGATGGAGGGTATrAGGCGGACTAGTTTTCGACCGGCT | 100 | 151 |
| UE | GTCCGCTCCGAGCCGGTCGAAAATACCC | 100 | 152 |
| Substrate | FAM-TCTTAGTTrAGGATAGTTCAT-TAM | 50 | 153 |

Table 21

| Strand (D2v1) | Sequence | Conc (nM) | SEQ ID NO: |
|---|---|---|---|
| Dz | GAACTATCTCCGAGCCGGTCGAAAACTAAGA | 100 | 154 |
| INH | CTCCATCTTAGTTTTCGACCGGCT | 120 | 155 |
| SCS | AGCCGGTCGAAAACTAAGACGTGAGGGTATTrAGGCGGACTCACG | 100 | 156 |
| UE | GAGTCCGCTCCGAGCCGGTCGAAAATACCCT | 100 | 157 |
| Substrate | FAM-TCTTAGTrAGCATAGTTCAT-TAM | 50 | 158 |

Table 22

| Strand (D2v2) | Sequence | Conc (nM) | SEQ ID NO: |
|---|---|---|---|
| Dz | GAACTATCTCCGAGCCGGTCGAAAACTAAGA | 100 | 159 |
| INH | CTCCATCTTAGTTTTCGACCGGCT | 120 | 160 |
| SCS | AGCCGGTCGAAAACTAAGACGCCCAGGGTATTrAGGCGGACTGGGCG | 100 | 161 |
| UE | CAGTCCGCTCCGAGCCGGTCGAAAATACCCT | 100 | 162 |
| Substrate | FAM-TCTTAGTrAGCATAGTTCAT-TAM | 50 | 163 |

Table 23

| Strand (D3) | Sequence | Conc (nM) | SEQ ID NO: |
|---|---|---|---|
| Dz | GAACTATCTCCGAGCCGGTCGAAAACTAAGA | 100 | 164 |
| INH | CGGGTTCTTAGTTTTCGACC | 120 | 165 |
| SCS | AGCCGGTCGAAAACTAAGACGCCCAGGGTATTrAGGCGG ACTGGGCG | 100 | 166 |
| UE | GTTATGCTCCGAGCCGGTCGAAACCCGTTTCT | 100 | 167 |
| Substrate | FAM-TCTTAGTrAGGATAGTTCAT-TAM | 50 | 168 |

Table 24

| Strand (D4) | Sequence | Conc (nM) | SEQ ID NO: |
|---|---|---|---|
| Dz | GAACTATCTCCGAGCCGGTCGAAAACTAAGA | 100 | 169 |
| INH | GAAGTTCTTAGTTTTCGACC | 120 | 170 |
| SCS | GGGATGTGAAGTrAGGATGGGACGGTCGAAAACTAAGAACTTCAC | 100 | 171 |
| UE | GTCCCATCTCCGAGCCGGTCGAAACTTCACATCCC | 100 | 172 |
| Substrate | FAM-TCTTAGTrAGGATAGTTCAT-TAM | 50 | 173 |

Table 25

| Strand (D4v1) | Sequence | Conc (nM) | SEQ ID NO: |
|---|---|---|---|
| M2-5' | GGGATGTGAAGTrAGGATGGGACAATCGAAAACTAAGAACTTCAC | 100 | 174 |
| M2-3' | GGGATGTGAAGTrAGGATGGGACGGTCGAAAACTAAAGACTTCAC | 100 | 175 |
| M2-5'3' | GGGATGTGAAGTrAGGATGGGACAATCGAAAACTAAAGAC TTCAC | 100 | 176 |
| S9 | GGGATGAGTGAAGTrAGGATGGGACGGTCGAAAACTAAGAACTTCACTC | 100 | 177 |
| 7GC | GGGATGTGCCGTrAGGATGGGACGGTCGAAAACTAAGAACGGCAC | 100 | 178 |
| 9GC | GGGATGAGTGCCGTrAGGATGGGACGGTCGAAAACTAAGAACGGCACTC | 100 | 179 |

Table 26

| Strand (D5v1) | Sequence | Conc (nM) | SEQ ID NO: |
|---|---|---|---|
| Dz | GAACTATCTCCGAGCCGGTCGAAAACTAAGA | 100 | 180 |
| INH | CGTATCTTAGTTTTCGACC | 120 | 181 |
| SCS | GGTCGAAAACTAAGAATACGGGACTACAGTAGTAGTrAG CGTATGAGGG | 100 | 182 |
| UE | CCCTCATACGCTCCGAGCCGGTCGAAACTACTAACT | 100 | 183 |
| Substrate | FAM-TCTTAGTrAGATAGTTCAT-TAM | 50 | 184 |

Table 27

| Strand (D5v2) | Sequence | Conc (nM) | SEQ ID NO: |
|---|---|---|---|
| Dz | GAACTATCTCCGAGCCGGTCGAAACTAAGA | 100 | 185 |
| INH | GCCACTCTTAGTTTTCGACC | 120 | 186 |
| SCS | GGTCGAAAACTAAGAGTGGCACTACAGAGGCCACTC ATAAA | 100 | 187 |
| UE | TTTATGAGTGGCTCCGAGCCGGTCGAAAGTCTGGT | 100 | 188 |
| Substrate | FAM-TCTTAGTrAGATAGTTCAT-TAM | 50 | 189 |

Fig. 16
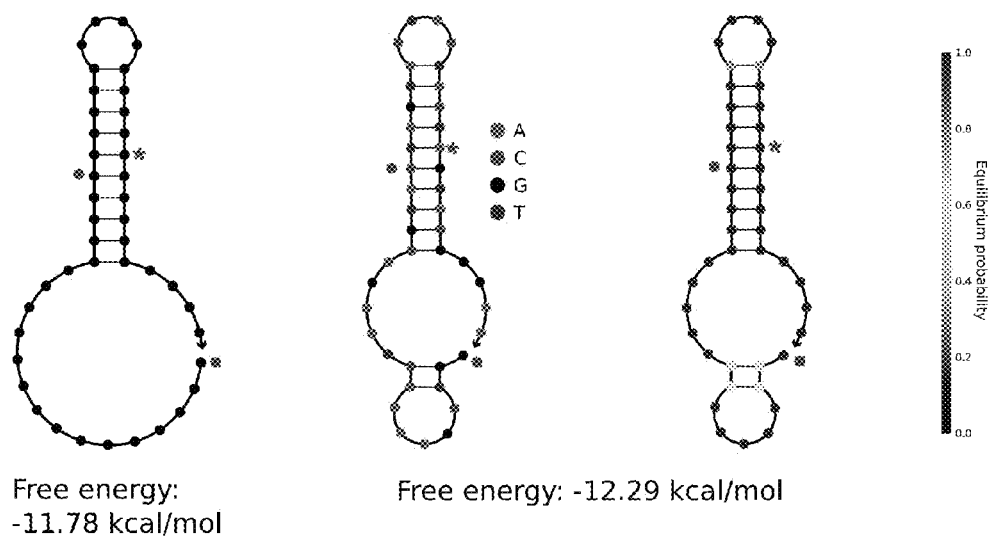
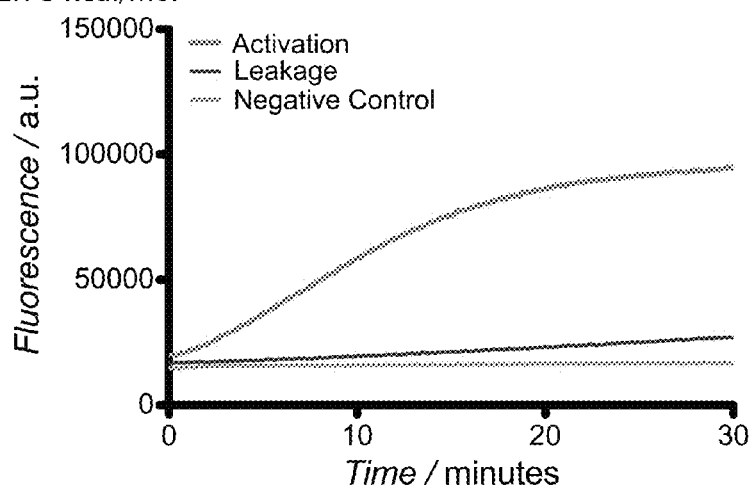

Table 28

| Strand (D6) | Sequence | Conc (nM) | SEQ ID NO: |
|---|---|---|---|
| Dz | GAACTATCTCCGAGCCGGTCGAAAACTAAGA | 100 | 190 |
| INH | CGACCCGTCTTAGTTTTCGACCGGC | 120 | 191 |
| SCS | GGTCGAAAACTAAGACGTACTAGTACTACTACTAGTACGGGAA | 100 | 192 |
| SCS ACT | GGTCGAAAACTAAGACGTACTAGTACTACTACTA | 100 | 193 |
| Substrate | FAM-TCTTAGTrAGGATAGTTCAT-TAM | 50 | 194 |

Table 29

| Strand (D7v1) | Sequence | Conc (nM) | SEQ ID NO: |
|---|---|---|---|
| Dz | GAACTATCTCCGAGCCGGTCGAAAACTAAGA | 100 | 195 |
| INH | GTAGCTCTTAGTTTCGACC | 120 | 196 |
| SCS | CACGCGTAGCGGTCGAAAACTAAGAGCTACAATrAGGCG TGAGG | 100 | 197 |
| UE | CCTCACGCTCCGAGCCGGTCGAATTGTAGC | 100 | 198 |
| Substrate | FAM-TCTTAGTrAGCATAGTTCAT-TAM | 50 | 199 |

Table 30

| Strand (D7v2) | Sequence | Conc (nM) | SEQ ID NO: |
|---|---|---|---|
| Dz | GAACTATCTCCGAGCCGGTCGAAAACTAAGA | 100 | 200 |
| INH | TTTACTCTTAGTTTCGACC | 120 | 201 |
| SCS | CCCTACGACTTTACGGTCGAAAACTAAGAGTAAAGTGCA ATrAGCGTAGGGATGAA | 100 | 202 |
| UE | TTCATCCCTACGTCCGAGCCGGTCGAATTGCACTTTAC | 100 | 203 |
| Substrate | FAM-TCTTAGTrAGCATAGTTCAT-TAM | 50 | 204 |

Table 31

| Strand (D7v3) | Sequence | Conc (nM) | SEQ ID NO: |
|---|---|---|---|
| Dz | GAACTATCTCCGAGCCGGTCGAAAACTAAGA | 100 | 205 |
| INH | TCTGATCTTAGTTTCGACC | 120 | 206 |
| SCS | AAAGCCGTGATCGGTCGAAAACTAAGATCAGATACATrAG CGGCTTAAC | 100 | 207 |
| UE | GTTAAAGCCGTCCGAGCCGGTCGAAATGTATCTGA | 100 | 208 |
| Substrate | FAM-TCTTAGTrAGCATAGTTCAT-TAM | 50 | 209 |

Table 32

| Strand (D7v4) | Sequence | Conc (nM) | SEQ ID NO: |
|---|---|---|---|
| Dz | GAACTATCTCCGAGCCGGTCGAAAACTAAGA | 100 | 210 |
| INH | TCCAATCTTAGTTTCGACC | 120 | 211 |
| SCS | CAAACGCTCCAATCGGTCGAAAACTAAGATTGGATAACTr AGGCCTTTGATG | 100 | 212 |
| UE | CATCAAAGGCTCCGAGCCGGTCGAAAGTTATCCAA | 100 | 213 |
| Substrate | FAM-TCTTAGTrAGCATAGTTCAT-TAM | 50 | 214 |

Table 33

| Strand (D8v1) | Sequence | Conc (nM) | SEQ ID NO: |
|---|---|---|---|
| Dz | GAACTATCTCCGAGCCGGTCGAAAACTAAGA | 100 | 215 |
| INH | ATGTACTTAGTTTTCGACC | 120 | 216 |
| SCS | CACGCCTATCTTAGGTCGAAACTAAGATTCATTTACTrAGGGCGTGATTAG | 100 | 217 |
| SCS ACT | CACGCCTATCTTAGGTCGAAACTAAGATTCATTTACTA | 100 | 218 |
| UE 11-10 | CTAATCACGCCTCCGAGCCGGTCGAAGTAAATGAA | 100 | 219 |
| UE 11-8 | CTAATCACGCCTCCGAGCCGGTCGAAGTAAATG | 100 | 220 |
| UE 10-8 | TAATCACGCCTCCGAGCCGGTCGAAGTAAATG | 100 | 221 |
| Substrate | FAM-TCTTAGTTrAGGATAGTTCAT-TAM | 50 | 222 |

Table 34

| Strand (D8v2) | Sequence | Conc (nM) | SEQ ID NO: |
|---|---|---|---|
| Dz | GAACTATCTCCGAGCCGGTCGAAAACTAAGA | 100 | 223 |
| INH | TCCAACTTAGTTTTCGACC | 120 | 224 |
| SCS | CACGCCTGTCTTAGGTCGAAACTAAGATTCATTACAGGGCGTGATTAG | 100 | 225 |
| SCS ACT | CACGCCTGTCTTAGGTCGAAACTAAGATTCATTACA | 100 | 226 |
| Substrate | FAM-TCTTAGTTrAGGATAGTTCAT-TAM | 50 | 227 |

Table 35

| Strand (D8v3) | Sequence | Conc (nM) | SEQ ID NO: |
|---|---|---|---|
| Dz | GAACTATCTCCGAGCCGGTCGAAAACTAAGA | 100 | 228 |
| INH | ATGTACTTAGTTTTCGACC | 120 | 229 |
| SCS | ACGCCTATCTTAGGTCGAAAACTAAGATTCATTACrAGGGCGTGATT | 100 | 230 |
| UE | AATCACGCCCTCCGAGCCGGTCGAAGTAAGA | 100 | 231 |
| Substrate | FAM-TCTTAGTTrAGGATAGTTCAT-TAM | 50 | 232 |

Table 36

| Strand (D8v4) | Sequence | Conc (nM) | SEQ ID NO: |
|---|---|---|---|
| Dz | GAACTATCTCCGAGCCGGTCGAAAACTAAGA | 100 | 233 |
| INH | ATGTACTTAGTTTTCGACCGGC | 120 | 234 |
| SCS | CGCCCTAATCTTAGGTCGAAAACTAAGATACATACTrAGGGCGTGATG | 100 | 235 |
| UE | ATCACGCCTCCGAGCCGGTCGAAGTATGTA | 100 | 236 |
| Substrate | FAM-TCTTAGTTrAGGATAGTTCAT-TAM | 50 | 237 |

Fig. 22
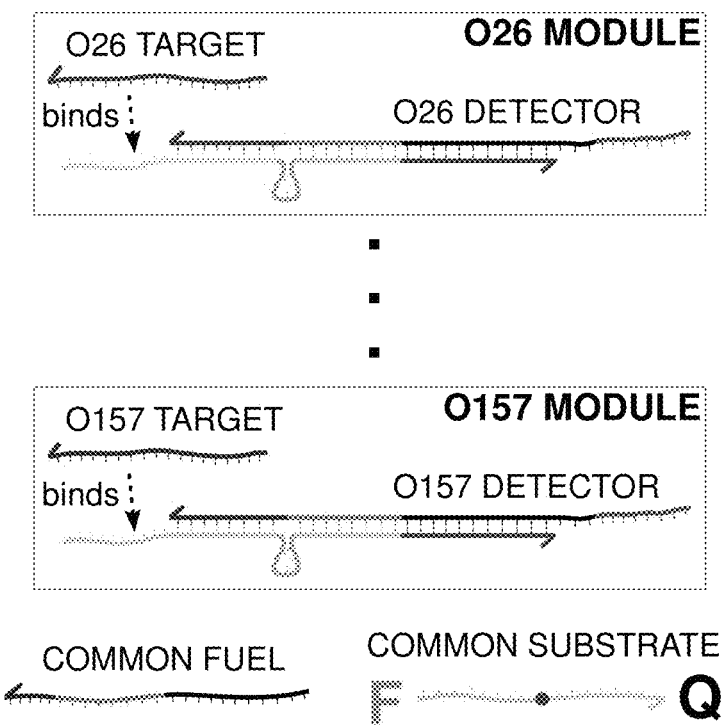
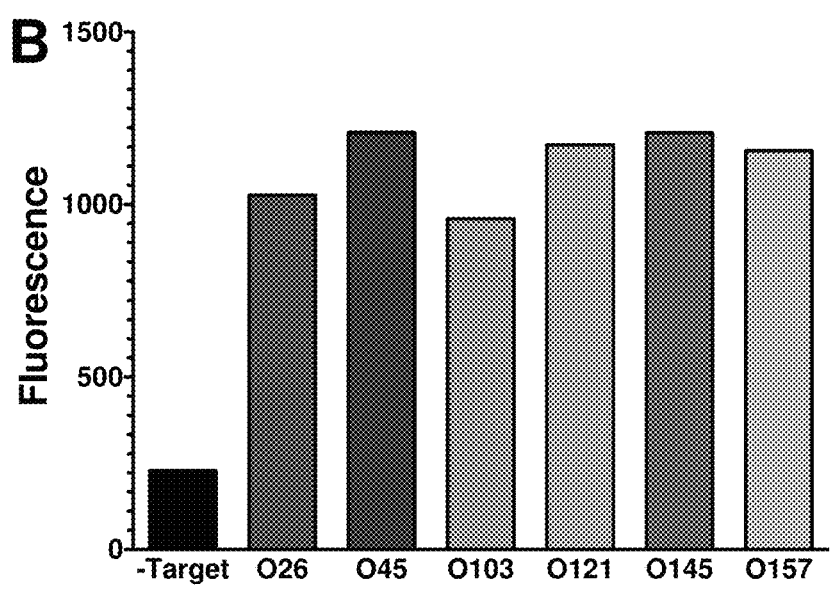

*Fig. 28*

Table 6.

| Strand | Sequence | |
|---|---|---|
| Layer 5 DNAzyme | GGGAGCCGTCCGAGCCGGTCGAAACTGTGGT | SEQ ID NO:29 |
| SCS$_5$ | GCCGCTATACAAAGGTCGAAATATTTGTACCACAGTrAGCGGCTCCC | SEQ ID NO:30 |
| Layer 4 DNAzyme | GGTAGCGCTCCGAGCCGGTCGAAATATTTGT | SEQ ID NO:31 |
| Layer 4 inhibitor | GTGGTACAAATATTTCGACCGGC | SEQ ID NO:32 |
| SCS$_4$ | GCGCCTATTCCCCGGTCGAAACAGGGGAACAAATATrAGGCGCTACC | SEQ ID NO:33 |
| Layer 3 DNAzyme | ACATGCCTCCGAGCCGGTCGAAACAGGGGA | SEQ ID NO:34 |
| Layer 3 inhibitor | TTTGTTCCCCTGTTTCGACCGGC | SEQ ID NO:35 |
| SCS$_3$ | GCCGCTAATACATGGTCGAAAGTATGTATCCCCTGTrAGCGGCATGT | SEQ ID NO:36 |
| Layer 2 DNAzyme | ATCACGCCTCCGAGCCGGTCGAAAGTATGTA | SEQ ID NO:37 |
| Layer 2 inhibitor | GGGGATACATACTTTCGACCGGC | SEQ ID NO:38 |
| SCS$_2$ | CGCCCTAATCTTAGGTCGAAAACTAAGATACATACTrAGGGCGTGATG | SEQ ID NO:39 |
| Layer 1 DNAzyme | GAACTATCTCCGAGCCGGTCGAAAACTAAGA | SEQ ID NO:40 |
| Layer 1 inhibitor | ATGTATCTTAGTTTTCGACCGGC | SEQ ID NO:41 |
| Layer 1 reporter substrate | /FAM/-TCTTAGTTrAGGATAGTTCAT-/TAM/ | SEQ ID NO:42 |

*Fig. 29*

Table 7.

| Strand | Sequence | |
|---|---|---|
| Upstream DNAzyme | ATCACGCCTCCGAGCCGGTCGAAAGTATGTA | SEQ ID NO:43 |
| Upstream inhibitor | CTCCTGTGCATACATACTTTCAACCAGCTAGGAGGCGTGATGATGAGTTTG | SEQ ID NO:44 |
| Input 1 | AGTATGTATGCACAGGAG | SEQ ID NO:45 |
| Input 2 | CAAACTCATCATCACGCC | SEQ ID NO:46 |
| SCS | CGCCCTAATCTTAGGTCGAAAACTAAGATACATACTrAGGGCGTGATG | SEQ ID NO:47 |
| Downstream DNAzyme | GAACTATCTCCGAGCCGGTCGAAAACTAAGA | SEQ ID NO:48 |
| Downstream inhibitor | ATGTATCTTAGTTTTCGACCGGC | SEQ ID NO:49 |
| Downstream reporter substrate | /FAM/-TCTTAGTTrAGGATAGTTCAT-/TAM/ | SEQ ID NO:50 |

*Fig. 30*

Table 8.

| Strand | Sequence | |
|---|---|---|
| Upstream DNAzyme | ATCACGCCTCCGAGCCGGTCGAAAGTATGTA | SEQ ID NO:51 |
| Upstream inhibitor | AAACATACATACTTTCGACCGGC | SEQ ID NO:52 |
| Input | GGTCGAAAGTATGTATGTTT | SEQ ID NO:53 |
| SCS | CGCCCTAATCTTAGGTCGAAAACTAAGATACATACTrAGGGCGTGATG | SEQ ID NO:54 |
| Downstream DNAzyme | TGATAGTTCATGTATCTTAGTTTTCGGAACTATCAGCGATGACTGTTTTCAGTCCACCCATGTAACTAAGA | SEQ ID NO:55 |
| Downstream reporter substrate | /FAM/-TCTTAGTTrAGGATAGTTCAT-/TAM/ | SEQ ID NO:56 |

*Fig. 31*

Table 9.

| Strand | Sequence | |
|---|---|---|
| Upstream DNAzyme | ATCACGCCTCCGAGCCGGTCGAAAGTATGTA | SEQ ID NO:57 |
| Upstream inhibitor | AAACATACATACTTTCGACCGGC | SEQ ID NO:58 |
| Input | GGTCGAAAGTATGTATGTTT | SEQ ID NO:59 |
| SCS | CGCCCTAATCTTAGGTCGAAAACTAAGATACATACTrAGGGCGTGATG | SEQ ID NO:60 |
| Downstream fluorophore strand | /FAM/-GCCGGTCGAAAACTAAGA | SEQ ID NO:61 |
| Downstream quencher strand | ATGTATCTTAGTTTTCGACC-/TAM/ | SEQ ID NO:62 |

*Fig. 32*

Table 10.

| Strand | Sequence | |
|---|---|---|
| DEN-1 target | ACCAACAACAAACACCAAA | SEQ ID NO:63 |
| DEN-1 upstream DNAzyme | ACACCAAATCCGAGCCGGTCGAACATCATTC | SEQ ID NO:64 |
| DEN-1 upstream inhibitor | TCTGTGCCTGGAATGATGTTCAACCAGCTAGGATTTGGTGTTTGTTGTTGGT | SEQ ID NO:65 |
| DEN-1 SCS | CAAACTCCTCTTAGGTCGAAAACTAAGAGAATGATGrAGTTTGGTGT | SEQ ID NO:66 |
| DEN-2 target | ACTGCTCTTAACATCCTC | SEQ ID NO:67 |
| DEN-2 upstream DNAzyme | ACATCCTCTCCGAGCCGGTCGAACATCATTC | SEQ ID NO:68 |
| DEN-2 upstream inhibitor | TCTGTGCCTGGAATGATGTTCAACCAGCTAGGAGAGGATGTTAAGAGCAGT | SEQ ID NO:69 |
| DEN-2 SCS | CCTCCTCCTCTTAGGTCGAAAACTAAGAGAATGATGrAGGAGGATGT | SEQ ID NO:70 |
| DEN-3 target | GTGTGCCAGTCTTCAAGC | SEQ ID NO:71 |
| DEN-3 upstream DNAzyme | CTTCAAGCTCCGAGCCGGTCGAACATCATTC | SEQ ID NO:72 |
| DEN-3 upstream inhibitor | TCTGTGCCTGGAATGATGTTCAACCAGCTAGGAGCTTGAAGACTGGCACAC | SEQ ID NO:73 |
| DEN-3 SCS | AAGCCTCCTCTTAGGTCGAAAACTAAGAGAATGATGrAGGCTTGAAG | SEQ ID NO:74 |
| DEN-4 target | TATTGAAGTCAGGCCACT | SEQ ID NO:75 |
| DEN-4 upstream DNAzyme | AGGCCACTTCCGAGCCGGTCGAACATCATTC | SEQ ID NO:76 |
| DEN-4 upstream inhibitor | TCTGTGCCTGGAATGATGTTCAACCAGCTAGGAAGTGGCCTGACTTCAATA | SEQ ID NO:77 |
| DEN-4 SCS | CACTCTCCTCTTAGGTCGAAAACTAAGAGAATGATGrAGAGTGGCCT | SEQ ID NO:78 |
| DengueA target | CATCATTCCAGGCACAGA | SEQ ID NO:79 |
| DengueB target | CATGGGCTACTGGATAGA | SEQ ID NO:80 |
| Downstream DNAzyme | TGGATAGATCCGAGCCGGTCGAAAACTAAGA | SEQ ID NO:81 |
| Downstream inhibitor | CATTCTTAGTTTTCGACCAGCTAGGATCTATCCAGTAGCCCATG | SEQ ID NO:82 |
| Downstream reporter substrate | /FAM/-TCTTAGTTrAGTCTATCCAAT-/TAM/ | SEQ ID NO:83 |

*Fig. 33*

Table 11.

| | | |
|---|---|---|
| O26 target | GATACTTTGAACCTTATATCCCAATATAGT | SEQ ID NO:84 |
| O26 deoxyribozyme | GAACTATC TCCGAGCCGGTCGAA AACTAAGA GATACTTTGAACCTT | SEQ ID NO:85 |
| O26 inhibitor | GGATAT AAGGTTCAAAGTATC CTCCATCTTAGTTTTCGACCGGC | SEQ ID NO:86 |
| O45 target | GCCAAACCAACTATGAACTGTC | SEQ ID NO:87 |
| O45 deoxyribozyme | GAACTATC TCCGAGCCGGTCGAA AACTAAGA GCCAAACCAACTATG | SEQ ID NO:88 |
| O45 inhibitor | GACAGT TCATAGTTGGTTTGGC CTCCATCTTAGTTTTCGACCGGC | SEQ ID NO:89 |
| O103 target | CCTGTTGTTTTATTATAAGTA | SEQ ID NO:90 |
| O103 deoxyribozyme | GAACTATCTCCGAGCCGGTCGAAAACTAAGAATTTTACTGG AAAAA | SEQ ID NO:91 |
| O103 inhibitor | GGTGCTTTTTTCCAGTAAAATCTCCATCTTAGTTTTCGACC GGC | SEQ ID NO:92 |
| O121 target | AGTATAACCTTTTACTTTCATGACAGGA | SEQ ID NO:93 |
| O121 deoxyribozyme | GAACTATC TCCGAGCCGGTCGAA AACTAAGA AGTATAACCTTTTAC | SEQ ID NO:94 |
| O121 inhibitor | ATGAAA GTAAAAGGTTATACT CTCCATCTTAGTTTTCGACCGGC | SEQ ID NO:95 |
| O145 target | CATACACTCCTAAATCTGTTGATGGTA | SEQ ID NO:96 |
| O145 deoxyribozyme | GAACTATC TCCGAGCCGGTCGAA AACTAAGA CATACACTCCTAAAT | SEQ ID NO:97 |
| O145 inhibitor | CAACAG ATTTAGGAGTGTATG CTCCATCTTAGTTTTCGACCGGC | SEQ ID NO:98 |
| O157 target | TGTCATTCGTGACAACCATTC | SEQ ID NO:99 |
| O157 deoxyribozyme | GAACTATC TCCGAGCCGGTCGAA AACTAAGA TGTCATTCGTGACAA | SEQ ID NO:100 |
| O157 inhibitor | GAATGG TTGTCACGAATGACA CTCCATCTTAGTTTTCGACCGGC | SEQ ID NO:101 |
| ATP deoxyribozyme (8nt blocker) | GAACTATCTCCGAGCCGGTCGAAAACTAAGAACCTTCCT | SEQ ID NO:102 |
| ATP deoxyribozyme (11nt blocker) | GAACTATCTCCGAGCCGGTCGAAAACTAAGAACCTTCCTCC G | SEQ ID NO:103 |
| ATP deoxyribozyme (15nt blocker) | GAACTATCTCCGAGCCGGTCGAAAACTAAGAACCTTCCTCC GCACA | SEQ ID NO:104 |
| ATP inhibitor | ACCTGGGGGAGTATGTGCGGAGGAAGGTCTCCATCTTAGTT TTCGACCGGC | SEQ ID NO:105 |
| Common fuel strand (with mismatch) | GGTCGAAAACTAAGATGCAG | SEQ ID NO:106 |
| Common fuel strand (without mismatch) | GGTCGAAAACTAAGATGGAG | SEQ ID NO:107 |
| Common substrate | /FAM/TCTTAGTTrAGGATAGTTCAT/TAM/ | SEQ ID NO:108 |

SEQUENCE LISTING

<160> NUMBER OF SEQ ID NOS: 237

<210> SEQ ID NO 1
<211> LENGTH: 23
<212> TYPE: DNA
<213> ORGANISM: artificial
<220> FEATURE:
<223> OTHER INFORMATION: Synthetic input sequence

<400> SEQUENCE: 1
gccggtcgaa aactaagata cat                                              23

<210> SEQ ID NO 2
<211> LENGTH: 31
<212> TYPE: DNA
<213> ORGANISM: artificial
<220> FEATURE:
<223> OTHER INFORMATION: DNAzyme

<400> SEQUENCE: 2
gaactatctc cgagccggtc gaaaactaag a                                     31

<210> SEQ ID NO 3
<211> LENGTH: 23
<212> TYPE: DNA
<213> ORGANISM: artificial
<220> FEATURE:
<223> OTHER INFORMATION: Synthetic inhibitor sequence

<400> SEQUENCE: 3
atgtatctta gttttcgacc ggc                                              23

<210> SEQ ID NO 4
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 4
tcttagttag gatagttcat                                                  20

<210> SEQ ID NO 5
<211> LENGTH: 23
<212> TYPE: DNA
<213> ORGANISM: artificial
<220> FEATURE:
<223> OTHER INFORMATION: Synthetic input sequence

<400> SEQUENCE: 5
atgtatctta gttttcgacc ggc                                              23

<210> SEQ ID NO 6
<211> LENGTH: 31
<212> TYPE: DNA
<213> ORGANISM: artificial

```
<220> FEATURE:
<223> OTHER INFORMATION: DNAzyme

<400> SEQUENCE: 6
gaactatctc cgagccggtc gaaaactaag a                            31

<210> SEQ ID NO 7
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 7
tcttagttag gatagttcat                                         20

<210> SEQ ID NO 8
<211> LENGTH: 21
<212> TYPE: DNA
<213> ORGANISM: artificial
<220> FEATURE:
<223> OTHER INFORMATION: Synthetic input sequence

<400> SEQUENCE: 8
cggtcgaaaa ctaagatgga g                                       21

<210> SEQ ID NO 9
<211> LENGTH: 20
<212> TYPE: DNA
<213> ORGANISM: artificial
<220> FEATURE:
<223> OTHER INFORMATION: Synthetic input sequence

<400> SEQUENCE: 9
gacctgaact atctccgagc                                         20

<210> SEQ ID NO 10
<211> LENGTH: 31
<212> TYPE: DNA
<213> ORGANISM: artificial
<220> FEATURE:
<223> OTHER INFORMATION: DNAzyme

<400> SEQUENCE: 10
gaactatctc cgagccggtc gaaaactaag a                            31

<210> SEQ ID NO 11
<211> LENGTH: 41
<212> TYPE: DNA
<213> ORGANISM: artificial
<220> FEATURE:
<223> OTHER INFORMATION: Synthetic inhibitor sequence

<400> SEQUENCE: 11
ctccatctta gttttcgacc ggctcggaga tagttcaggt c                 41
```

```
<210> SEQ ID NO 12
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 12
tcttagttag gatagttcat                                               20

<210> SEQ ID NO 13
<211> LENGTH: 18
<212> TYPE: DNA
<213> ORGANISM: artificial
<220> FEATURE:
<223> OTHER INFORMATION: Synthetic input sequence

<400> SEQUENCE: 13
aactaagatg atgtggag                                                 18

<210> SEQ ID NO 14
<211> LENGTH: 18
<212> TYPE: DNA
<213> ORGANISM: artificial
<220> FEATURE:
<223> OTHER INFORMATION: Synthetic input sequence

<400> SEQUENCE: 14
gaggttgatg gaactatc                                                 18

<210> SEQ ID NO 15
<211> LENGTH: 31
<212> TYPE: DNA
<213> ORGANISM: artificial
<220> FEATURE:
<223> OTHER INFORMATION: DNAzyme

<400> SEQUENCE: 15
gaactatctc cgagccggtc gaaaactaag a                                  31

<210> SEQ ID NO 16
<211> LENGTH: 51
<212> TYPE: DNA
<213> ORGANISM: artificial
<220> FEATURE:
<223> OTHER INFORMATION: Synthetic inhibitor sequence

<400> SEQUENCE: 16
ctccacatca tcttagtttt cgaccggctc ggagatagtt ccatcaacct c             51

<210> SEQ ID NO 17
<211> LENGTH: 51
<212> TYPE: DNA
<213> ORGANISM: artificial
<220> FEATURE:
<223> OTHER INFORMATION: Synthetic inhibitor sequence
```

<400> SEQUENCE: 17
ctccacatca tcttagttttt cgaccagctc ggagatagtt ccatcaacct c            51

<210> SEQ ID NO 18
<211> LENGTH: 51
<212> TYPE: DNA
<213> ORGANISM: artificial
<220> FEATURE:
<223> OTHER INFORMATION: Synthetic inhibitor sequence

<400> SEQUENCE: 18
ctccacatca tcttagttttt caaccggcta ggagatagtt ccatcaacct c            51

<210> SEQ ID NO 19
<211> LENGTH: 51
<212> TYPE: DNA
<213> ORGANISM: artificial
<220> FEATURE:
<223> OTHER INFORMATION: Synthetic inhibitor sequence

<400> SEQUENCE: 19
ctccacatca tcttagttttt caaccagcta ggagatagtt ccatcaacct c            51

<210> SEQ ID NO 20
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 20
tcttagttag gatagttcat                                                20

<210> SEQ ID NO 21
<211> LENGTH: 18
<212> TYPE: DNA
<213> ORGANISM: artificial
<220> FEATURE:
<223> OTHER INFORMATION: Synthetic input sequence

<400> SEQUENCE: 21
aactaagatg atgtggag                                                  18

<210> SEQ ID NO 22
<211> LENGTH: 18
<212> TYPE: DNA
<213> ORGANISM: artificial
<220> FEATURE:
<223> OTHER INFORMATION: Synthetic input sequence

<400> SEQUENCE: 22
gaggttgatg gaactatc                                                  18

<210> SEQ ID NO 23

```
<211> LENGTH: 31
<212> TYPE: DNA
<213> ORGANISM: artificial
<220> FEATURE:
<223> OTHER INFORMATION: DNAzyme

<400> SEQUENCE: 23
gaactatctc cgagccggtc gaaaactaag a                                    31

<210> SEQ ID NO 24
<211> LENGTH: 51
<212> TYPE: DNA
<213> ORGANISM: artificial
<220> FEATURE:
<223> OTHER INFORMATION: Synthetic inhibitor sequence

<400> SEQUENCE: 24
ctccacatca tcttagtttt caaccagcta ggagatagtt ccatcaacct c              51

<210> SEQ ID NO 25
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 25
tcttagttag gatagttcat                                                 20

<210> SEQ ID NO 26
<211> LENGTH: 22
<212> TYPE: DNA
<213> ORGANISM: artificial
<220> FEATURE:
<223> OTHER INFORMATION: Synthetic input sequence

<400> SEQUENCE: 26
cggctcggat ctatccacat tc                                              22

<210> SEQ ID NO 27
<211> LENGTH: 31
<212> TYPE: DNA
<213> ORGANISM: artificial
<220> FEATURE:
<223> OTHER INFORMATION: DNAzyme

<400> SEQUENCE: 27
tggatagatc cgagccggtc gaaaactaag a                                    31

<210> SEQ ID NO 28
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
```

```
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 28
tcttagttag tctatccaat                                              20

<210> SEQ ID NO 29
<211> LENGTH: 31
<212> TYPE: DNA
<213> ORGANISM: artificial
<220> FEATURE:
<223> OTHER INFORMATION: DNAzyme

<400> SEQUENCE: 29
gggagccgtc cgagccggtc gaaactgtgg t                                 31

<210> SEQ ID NO 30
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 30
gccgctatac aaaggtcgaa atatttgtac cacagtagcg gctccc                 46

<210> SEQ ID NO 31
<211> LENGTH: 31
<212> TYPE: DNA
<213> ORGANISM: artificial
<220> FEATURE:
<223> OTHER INFORMATION: DNAzyme

<400> SEQUENCE: 31
ggtagcgctc cgagccggtc gaaatatttg t                                 31

<210> SEQ ID NO 32
<211> LENGTH: 23
<212> TYPE: DNA
<213> ORGANISM: artificial
<220> FEATURE:
<223> OTHER INFORMATION: Synthetic inhibitor sequence

<400> SEQUENCE: 32
gtggtacaaa tatttcgacc ggc                                          23

<210> SEQ ID NO 33
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
```

```
<223> OTHER INFORMATION: ribose adenine

<400> SEQUENCE: 33
gcgcctattc cccggtcgaa acagggaac aaatataggc gctacc          46

<210> SEQ ID NO 34
<211> LENGTH: 31
<212> TYPE: DNA
<213> ORGANISM: artificial
<220> FEATURE:
<223> OTHER INFORMATION: DNAzyme

<400> SEQUENCE: 34
acatgccgtc cgagccggtc gaaacagggg a                          31

<210> SEQ ID NO 35
<211> LENGTH: 23
<212> TYPE: DNA
<213> ORGANISM: artificial
<220> FEATURE:
<223> OTHER INFORMATION: Synthetic inhibitor sequence

<400> SEQUENCE: 35
tttgttcccc tgtttcgacc ggc                                   23

<210> SEQ ID NO 36
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 36
gccgctaata catggtcgaa agtatgtatc ccctgtagcg gcatgt          46

<210> SEQ ID NO 37
<211> LENGTH: 31
<212> TYPE: DNA
<213> ORGANISM: artificial
<220> FEATURE:
<223> OTHER INFORMATION: DNAzyme

<400> SEQUENCE: 37
atcacgcctc cgagccggtc gaaagtatgt a                          31

<210> SEQ ID NO 38
<211> LENGTH: 23
<212> TYPE: DNA
<213> ORGANISM: artificial
<220> FEATURE:
<223> OTHER INFORMATION: Synthetic inhibitor sequence

<400> SEQUENCE: 38
ggggatacat actttcgacc ggc                                   23

<210> SEQ ID NO 39
<211> LENGTH: 47
<212> TYPE: DNA
<213> ORGANISM: artificial
<220> FEATURE:
<223> OTHER INFORMATION: Synthetic structured chimeric substrate (SCS)
      sequence
```

```
<220> FEATURE:
<221> NAME/KEY: misc_RNA
<222> LOCATION: (37)..(37)
<223> OTHER INFORMATION: ribose adenine

<400> SEQUENCE: 39
cgccctaatc ttaggtcgaa aactaagata catactaggg cgtgatg                    47

<210> SEQ ID NO 40
<211> LENGTH: 31
<212> TYPE: DNA
<213> ORGANISM: artificial
<220> FEATURE:
<223> OTHER INFORMATION: DNAzyme

<400> SEQUENCE: 40
gaactatctc cgagccggtc gaaaactaag a                                     31

<210> SEQ ID NO 41
<211> LENGTH: 23
<212> TYPE: DNA
<213> ORGANISM: artificial
<220> FEATURE:
<223> OTHER INFORMATION: Synthetic inhibitor sequence

<400> SEQUENCE: 41
atgtatctta gttttcgacc ggc                                              23

<210> SEQ ID NO 42
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 42
tcttagttag gatagttcat                                                  20

<210> SEQ ID NO 43
<211> LENGTH: 31
<212> TYPE: DNA
<213> ORGANISM: artificial
<220> FEATURE:
<223> OTHER INFORMATION: DNAzyme

<400> SEQUENCE: 43
atcacgcctc cgagccggtc gaaagtatgt a                                     31

<210> SEQ ID NO 44
<211> LENGTH: 51
<212> TYPE: DNA
<213> ORGANISM: artificial
<220> FEATURE:
<223> OTHER INFORMATION: Synthetic inhibitor sequence

<400> SEQUENCE: 44
```
ctcctgtgca tacatacttt caaccagcta ggaggcgtga tgatgagttt g        51

<210> SEQ ID NO 45
<211> LENGTH: 18
<212> TYPE: DNA
<213> ORGANISM: artificial
<220> FEATURE:
<223> OTHER INFORMATION: Synthetic input sequence

<400> SEQUENCE: 45
agtatgtatg cacaggag                                              18

<210> SEQ ID NO 46
<211> LENGTH: 18
<212> TYPE: DNA
<213> ORGANISM: artificial
<220> FEATURE:
<223> OTHER INFORMATION: Synthetic input sequence

<400> SEQUENCE: 46
caaactcatc atcacgcc                                              18

<210> SEQ ID NO 47
<211> LENGTH: 47
<212> TYPE: DNA
<213> ORGANISM: artificial
<220> FEATURE:
<223> OTHER INFORMATION: Synthetic structured chimeric substrate (SCS)
      sequence

<400> SEQUENCE: 47
cgccctaatc ttaggtcgaa aactaagata catactaggg cgtgatg               47

<210> SEQ ID NO 48
<211> LENGTH: 31
<212> TYPE: DNA
<213> ORGANISM: artificial
<220> FEATURE:
<223> OTHER INFORMATION: DNAzyme

<400> SEQUENCE: 48
gaactatctc cgagccggtc gaaaactaag a                               31

<210> SEQ ID NO 49
<211> LENGTH: 23
<212> TYPE: DNA
<213> ORGANISM: artificial
<220> FEATURE:
<223> OTHER INFORMATION: Synthetic inhibitor sequence

<400> SEQUENCE: 49
atgtatctta gttttcgacc ggc                                        23

<210> SEQ ID NO 50
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:

```
<221> NAME/KEY: misc_feature
<222> LOCATION: (20)..(20)
<223> OTHER INFORMATION: conjugated to a fluorophore quencher

<400> SEQUENCE: 50
tcttagttag gatagttcat                                                  20

<210> SEQ ID NO 51
<211> LENGTH: 31
<212> TYPE: DNA
<213> ORGANISM: artificial
<220> FEATURE:
<223> OTHER INFORMATION: DNAzyme

<400> SEQUENCE: 51
atcacgcctc cgagccggtc gaaagtatgt a                                     31

<210> SEQ ID NO 52
<211> LENGTH: 23
<212> TYPE: DNA
<213> ORGANISM: artificial
<220> FEATURE:
<223> OTHER INFORMATION: Synthetic inhibitor sequence

<400> SEQUENCE: 52
aaacatacat actttcgacc ggc                                              23

<210> SEQ ID NO 53
<211> LENGTH: 20
<212> TYPE: DNA
<213> ORGANISM: artificial
<220> FEATURE:
<223> OTHER INFORMATION: Synthetic input sequence

<400> SEQUENCE: 53
ggtcgaaagt atgtatgttt                                                  20

<210> SEQ ID NO 54
<211> LENGTH: 47
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 54
cgccctaatc ttaggtcgaa aactaagata catactaggg cgtgatg                    47

<210> SEQ ID NO 55
<211> LENGTH: 71
<212> TYPE: DNA
<213> ORGANISM: artificial
<220> FEATURE:
<223> OTHER INFORMATION: DNAzyme

<400> SEQUENCE: 55
tgatagttca tgtatcttag ttttcggaac tatcagcgat gactgttttc agtccaccca      60
tgtaactaag a                                                           71

<210> SEQ ID NO 56
<211> LENGTH: 20
<212> TYPE: DNA
```

```
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 56
tcttagttag gatagttcat                                               20

<210> SEQ ID NO 57
<211> LENGTH: 31
<212> TYPE: DNA
<213> ORGANISM: artificial
<220> FEATURE:
<223> OTHER INFORMATION: DNAzyme

<400> SEQUENCE: 57
atcacgcctc cgagccggtc gaaagtatgt a                                  31

<210> SEQ ID NO 58
<211> LENGTH: 23
<212> TYPE: DNA
<213> ORGANISM: artificial
<220> FEATURE:
<223> OTHER INFORMATION: Synthetic inhibitor sequence

<400> SEQUENCE: 58
aaacatacat actttcgacc ggc                                           23

<210> SEQ ID NO 59
<211> LENGTH: 20
<212> TYPE: DNA
<213> ORGANISM: artificial
<220> FEATURE:
<223> OTHER INFORMATION: Synthetic input sequence

<400> SEQUENCE: 59
ggtcgaaagt atgtatgttt                                               20

<210> SEQ ID NO 60
<211> LENGTH: 47
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 60
cgccctaatc ttaggtcgaa aactaagata catactaggg cgtgatg                 47

<210> SEQ ID NO 61
<211> LENGTH: 18
<212> TYPE: DNA
<213> ORGANISM: artificial
<220> FEATURE:
```

```
<223> OTHER INFORMATION: Synthetic downstream fluorophore strand
      sequence
<220> FEATURE:
<221> NAME/KEY: misc_feature
<222> LOCATION: (1)..(1)
<223> OTHER INFORMATION: conjugated to a fluorescent label

<400> SEQUENCE: 61
gccggtcgaa aactaaga                                                   18

<210> SEQ ID NO 62
<211> LENGTH: 20
<212> TYPE: DNA
<213> ORGANISM: artificial
<220> FEATURE:
<223> OTHER INFORMATION: Synthetic downstream quencher strand sequence
<220> FEATURE:
<221> NAME/KEY: misc_feature
<222> LOCATION: (20)..(20)
<223> OTHER INFORMATION: conjugated to a fluorophore quencher

<400> SEQUENCE: 62
atgtatctta gttttcgacc                                                 20

<210> SEQ ID NO 63
<211> LENGTH: 19
<212> TYPE: DNA
<213> ORGANISM: artificial
<220> FEATURE:
<223> OTHER INFORMATION: Synthetic target sequence

<400> SEQUENCE: 63
accaacaaca aacaccaaa                                                  19

<210> SEQ ID NO 64
<211> LENGTH: 31
<212> TYPE: DNA
<213> ORGANISM: artificial
<220> FEATURE:
<223> OTHER INFORMATION: DNAzyme

<400> SEQUENCE: 64
acaccaaatc cgagccggtc gaacatcatt c                                    31

<210> SEQ ID NO 65
<211> LENGTH: 52
<212> TYPE: DNA
<213> ORGANISM: artificial
<220> FEATURE:
<223> OTHER INFORMATION: Synthetic inhibitor sequence

<400> SEQUENCE: 65
tctgtgcctg gaatgatgtt caaccagcta ggatttggtg tttgttgttg gt             52

<210> SEQ ID NO 66
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 66
caaactcctc ttaggtcgaa aactaagaga atgatgagtt tggtgt                    46
```

<210> SEQ ID NO 67
<211> LENGTH: 18
<212> TYPE: DNA
<213> ORGANISM: artificial
<220> FEATURE:
<223> OTHER INFORMATION: Synthetic target sequence

<400> SEQUENCE: 67
actgctctta acatcctc                                                     18

<210> SEQ ID NO 68
<211> LENGTH: 31
<212> TYPE: DNA
<213> ORGANISM: artificial
<220> FEATURE:
<223> OTHER INFORMATION: DNAzyme

<400> SEQUENCE: 68
acatcctctc cgagccggtc gaacatcatt c                                       31

<210> SEQ ID NO 69
<211> LENGTH: 51
<212> TYPE: DNA
<213> ORGANISM: artificial
<220> FEATURE:
<223> OTHER INFORMATION: Synthetic inhibitor sequence

<400> SEQUENCE: 69
tctgtgcctg gaatgatgtt caaccagcta ggagaggatg ttaagagcag t                 51

<210> SEQ ID NO 70
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 70
cctcctcctc ttaggtcgaa aactaagaga atgatgagga ggatgt                      46

<210> SEQ ID NO 71
<211> LENGTH: 18
<212> TYPE: DNA
<213> ORGANISM: artificial
<220> FEATURE:
<223> OTHER INFORMATION: Synthetic target sequence

<400> SEQUENCE: 71
gtgtgccagt cttcaagc                                                     18

<210> SEQ ID NO 72
<211> LENGTH: 31
<212> TYPE: DNA
<213> ORGANISM: artificial
<220> FEATURE:
<223> OTHER INFORMATION: DNAzyme

<400> SEQUENCE: 72
cttcaagctc cgagccggtc gaacatcatt c                                       31

```
<210> SEQ ID NO 73
<211> LENGTH: 51
<212> TYPE: DNA
<213> ORGANISM: artificial
<220> FEATURE:
<223> OTHER INFORMATION: Synthetic inhibitor sequence

<400> SEQUENCE: 73
tctgtgcctg gaatgatgtt caaccagcta ggagcttgaa gactggcaca c        51

<210> SEQ ID NO 74
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 74
aagcctcctc ttaggtcgaa aactaagaga atgatgaggc ttgaag             46

<210> SEQ ID NO 75
<211> LENGTH: 18
<212> TYPE: DNA
<213> ORGANISM: artificial
<220> FEATURE:
<223> OTHER INFORMATION: Synthetic target sequence

<400> SEQUENCE: 75
tattgaagtc aggccact                                            18

<210> SEQ ID NO 76
<211> LENGTH: 31
<212> TYPE: DNA
<213> ORGANISM: artificial
<220> FEATURE:
<223> OTHER INFORMATION: DNAzyme

<400> SEQUENCE: 76
aggccacttc cgagccggtc gaacatcatt c                             31

<210> SEQ ID NO 77
<211> LENGTH: 51
<212> TYPE: DNA
<213> ORGANISM: artificial
<220> FEATURE:
<223> OTHER INFORMATION: Synthetic inhibitor sequence

<400> SEQUENCE: 77
tctgtgcctg gaatgatgtt caaccagcta ggaagtggcc tgacttcaat a        51

<210> SEQ ID NO 78
<211> LENGTH: 46
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 78
```
cactctcctc ttaggtcgaa aactaagaga atgatgagag tggcct         46

<210> SEQ ID NO 79
<211> LENGTH: 18
<212> TYPE: DNA
<213> ORGANISM: artificial
<220> FEATURE:
<223> OTHER INFORMATION: Synthetic target sequence

<400> SEQUENCE: 79
catcattcca ggcacaga                                         18

<210> SEQ ID NO 80
<211> LENGTH: 18
<212> TYPE: DNA
<213> ORGANISM: artificial
<220> FEATURE:
<223> OTHER INFORMATION: Synthetic target sequence

<400> SEQUENCE: 80
catgggctac tggataga                                         18

<210> SEQ ID NO 81
<211> LENGTH: 31
<212> TYPE: DNA
<213> ORGANISM: artificial
<220> FEATURE:
<223> OTHER INFORMATION: DNAzyme

<400> SEQUENCE: 81
tggatagatc cgagccggtc gaaaactaag a                          31

<210> SEQ ID NO 82
<211> LENGTH: 46
<212> TYPE: DNA
<213> ORGANISM: artificial
<220> FEATURE:
<223> OTHER INFORMATION: Synthetic inhibitor sequence

<400> SEQUENCE: 82
cattctctta gttttcgacc agctaggatc tatccagtag cccatg          46

<210> SEQ ID NO 83
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 83
tcttagttag tctatccaat                                       20

<210> SEQ ID NO 84
<211> LENGTH: 30
<212> TYPE: DNA
<213> ORGANISM: artificial

```
<220> FEATURE:
<223> OTHER INFORMATION: Synthetic target sequence

<400> SEQUENCE: 84
gatactttga accttatatc ccaatatagt                                      30

<210> SEQ ID NO 85
<211> LENGTH: 46
<212> TYPE: DNA
<213> ORGANISM: artificial
<220> FEATURE:
<223> OTHER INFORMATION: DNAzyme

<400> SEQUENCE: 85
gaactatctc cgagccggtc gaaaactaag agatactttg aacctt                    46

<210> SEQ ID NO 86
<211> LENGTH: 44
<212> TYPE: DNA
<213> ORGANISM: artificial
<220> FEATURE:
<223> OTHER INFORMATION: Synthetic inhibitor sequence

<400> SEQUENCE: 86
ggatataagg ttcaaagtat cctccatctt agttttcgac cggc                      44

<210> SEQ ID NO 87
<211> LENGTH: 22
<212> TYPE: DNA
<213> ORGANISM: artificial
<220> FEATURE:
<223> OTHER INFORMATION: Synthetic target sequence

<400> SEQUENCE: 87
gccaaaccaa ctatgaactg tc                                              22

<210> SEQ ID NO 88
<211> LENGTH: 46
<212> TYPE: DNA
<213> ORGANISM: artificial
<220> FEATURE:
<223> OTHER INFORMATION: DNAzyme

<400> SEQUENCE: 88
gaactatctc cgagccggtc gaaaactaag agccaaacca actatg                    46

<210> SEQ ID NO 89
<211> LENGTH: 45
<212> TYPE: DNA
<213> ORGANISM: artificial
<220> FEATURE:
<223> OTHER INFORMATION: Synthetic inhibitor sequence

<400> SEQUENCE: 89
gacagttcat agttggtttg gcctccatct tagttttcga ccggc                     45

<210> SEQ ID NO 90
<211> LENGTH: 21
<212> TYPE: DNA
<213> ORGANISM: artificial
<220> FEATURE:
<223> OTHER INFORMATION: Synthetic target sequence

<400> SEQUENCE: 90
cctgttgttt tattataagt a                                               21
```

```
<210> SEQ ID NO 91
<211> LENGTH: 46
<212> TYPE: DNA
<213> ORGANISM: artificial
<220> FEATURE:
<223> OTHER INFORMATION: DNAzyme

<400> SEQUENCE: 91
gaactatctc cgagccggtc gaaaactaag aattttactg gaaaaa        46

<210> SEQ ID NO 92
<211> LENGTH: 44
<212> TYPE: DNA
<213> ORGANISM: artificial
<220> FEATURE:
<223> OTHER INFORMATION: Synthetic inhibitor sequence

<400> SEQUENCE: 92
ggtgcttttt tccagtaaaa tctccatctt agttttcgac cggc          44

<210> SEQ ID NO 93
<211> LENGTH: 28
<212> TYPE: DNA
<213> ORGANISM: artificial
<220> FEATURE:
<223> OTHER INFORMATION: Synthetic target sequence

<400> SEQUENCE: 93
agtataacct tttactttca tgacagga                            28

<210> SEQ ID NO 94
<211> LENGTH: 46
<212> TYPE: DNA
<213> ORGANISM: artificial
<220> FEATURE:
<223> OTHER INFORMATION: Synthetic target sequence

<400> SEQUENCE: 94
gaactatctc cgagccggtc gaaaactaag aagtataacc ttttac        46

<210> SEQ ID NO 95
<211> LENGTH: 44
<212> TYPE: DNA
<213> ORGANISM: artificial
<220> FEATURE:
<223> OTHER INFORMATION: Synthetic inhibitor sequence

<400> SEQUENCE: 95
atgaaagtaa aaggttatac tctccatctt agttttcgac cggc          44

<210> SEQ ID NO 96
<211> LENGTH: 27
<212> TYPE: DNA
<213> ORGANISM: artificial
<220> FEATURE:
<223> OTHER INFORMATION: Synthetic target sequence

<400> SEQUENCE: 96
catacactcc taaatctgtt gatggta                             27

<210> SEQ ID NO 97
<211> LENGTH: 46
<212> TYPE: DNA
<213> ORGANISM: artificial
<220> FEATURE:
<223> OTHER INFORMATION: DNAzyme
```

<400> SEQUENCE: 97
gaactatctc cgagccggtc gaaaactaag acatacactc ctaaat                    46

<210> SEQ ID NO 98
<211> LENGTH: 44
<212> TYPE: DNA
<213> ORGANISM: artificial
<220> FEATURE:
<223> OTHER INFORMATION: Synthetic inhibitor sequence

<400> SEQUENCE: 98
caacagattt aggagtgtat gctccatctt agttttcgac cggc                      44

<210> SEQ ID NO 99
<211> LENGTH: 21
<212> TYPE: DNA
<213> ORGANISM: artificial
<220> FEATURE:
<223> OTHER INFORMATION: Synthetic target sequence

<400> SEQUENCE: 99
tgtcattcgt gacaaccatt c                                               21

<210> SEQ ID NO 100
<211> LENGTH: 46
<212> TYPE: DNA
<213> ORGANISM: artificial
<220> FEATURE:
<223> OTHER INFORMATION: DNAzyme

<400> SEQUENCE: 100
gaactatctc cgagccggtc gaaaactaag atgtcattcg tgacaa                    46

<210> SEQ ID NO 101
<211> LENGTH: 44
<212> TYPE: DNA
<213> ORGANISM: artificial
<220> FEATURE:
<223> OTHER INFORMATION: Synthetic inhibitor sequence

<400> SEQUENCE: 101
gaatggttgt cacgaatgac actccatctt agttttcgac cggc                      44

<210> SEQ ID NO 102
<211> LENGTH: 39
<212> TYPE: DNA
<213> ORGANISM: artificial
<220> FEATURE:
<223> OTHER INFORMATION: DNAzyme

<400> SEQUENCE: 102
gaactatctc cgagccggtc gaaaactaag aaccttcct                            39

<210> SEQ ID NO 103
<211> LENGTH: 42
<212> TYPE: DNA
<213> ORGANISM: artificial
<220> FEATURE:
<223> OTHER INFORMATION: DNAzyme

<400> SEQUENCE: 103
gaactatctc cgagccggtc gaaaactaag aaccttcctc cg                        42

<210> SEQ ID NO 104

```
<211> LENGTH: 46
<212> TYPE: DNA
<213> ORGANISM: artificial
<220> FEATURE:
<223> OTHER INFORMATION: DNAzyme

<400> SEQUENCE: 104
gaactatctc cgagccggtc gaaaactaag aaccttcctc cgcaca          46

<210> SEQ ID NO 105
<211> LENGTH: 51
<212> TYPE: DNA
<213> ORGANISM: artificial
<220> FEATURE:
<223> OTHER INFORMATION: Synthetic inhibitor sequence

<400> SEQUENCE: 105
acctggggga gtatgtgcgg aggaaggtct ccatcttagt tttcgaccgg c     51

<210> SEQ ID NO 106
<211> LENGTH: 20
<212> TYPE: DNA
<213> ORGANISM: artificial
<220> FEATURE:
<223> OTHER INFORMATION: Common fuel strand (with mismatch)

<400> SEQUENCE: 106
ggtcgaaaac taagatgcag                                        20

<210> SEQ ID NO 107
<211> LENGTH: 20
<212> TYPE: DNA
<213> ORGANISM: artificial
<220> FEATURE:
<223> OTHER INFORMATION: Common fuel strand (without mismatch)

<400> SEQUENCE: 107
ggtcgaaaac taagatggag                                        20

<210> SEQ ID NO 108
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 108
tcttagttag gatagttcat                                        20

<210> SEQ ID NO 109
<211> LENGTH: 31
<212> TYPE: DNA
<213> ORGANISM: artificial
<220> FEATURE:
<223> OTHER INFORMATION: DNAzyme

<400> SEQUENCE: 109
```

```
gaactatctc cgagccggtc gaaaactaag a                                    31
```

<210> SEQ ID NO 110
<211> LENGTH: 24
<212> TYPE: DNA
<213> ORGANISM: artificial
<220> FEATURE:
<223> OTHER INFORMATION: Synthetic inhibitor sequence

<400> SEQUENCE: 110

```
ctccatctta gttttcgacc ggct                                            24
```

<210> SEQ ID NO 111
<211> LENGTH: 52
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (21)..(21)
<223> OTHER INFORMATION: ribose adenine

<400> SEQUENCE: 111

```
ctccatctta gttgggtatt aggcggacag ccggtcgaaa actaagatgg ag             52
```

<210> SEQ ID NO 112
<211> LENGTH: 28
<212> TYPE: DNA
<213> ORGANISM: artificial
<220> FEATURE:
<223> OTHER INFORMATION: DNAzyme

<400> SEQUENCE: 112

```
gtccgctccg agccggtcga aaataccc                                        28
```

<210> SEQ ID NO 113
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 113

```
tcttagttag gatagttcat                                                 20
```

<210> SEQ ID NO 114
<211> LENGTH: 31
<212> TYPE: DNA
<213> ORGANISM: artificial
<220> FEATURE:
<223> OTHER INFORMATION: DNAzyme

<400> SEQUENCE: 114

```
gaactatctc cgagccggtc gaaaactaag a                                    31
```

```
<210> SEQ ID NO 115
<211> LENGTH: 24
<212> TYPE: DNA
<213> ORGANISM: artificial
<220> FEATURE:
<223> OTHER INFORMATION: Synthetic inhibitor sequence

<400> SEQUENCE: 115
ctccatcttc gttttcgacc ggct                                              24

<210> SEQ ID NO 116
<211> LENGTH: 52
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (21)..(21)
<223> OTHER INFORMATION: ribose adenine

<400> SEQUENCE: 116
ctccatcttc gttgggtatt aggcggacag ccggtcgaaa acgaagatgg ag               52

<210> SEQ ID NO 117
<211> LENGTH: 28
<212> TYPE: DNA
<213> ORGANISM: artificial
<220> FEATURE:
<223> OTHER INFORMATION: DNAzyme

<400> SEQUENCE: 117
gtccgctccg agccggtcga aaataccc                                          28

<210> SEQ ID NO 118
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 118
tcttagttag gatagttcat                                                   20

<210> SEQ ID NO 119
<211> LENGTH: 31
<212> TYPE: DNA
<213> ORGANISM: artificial
<220> FEATURE:
<223> OTHER INFORMATION: DNAzyme

<400> SEQUENCE: 119
gaactatctc cgagccggtc gaaaactaag a                                      31
```

<210> SEQ ID NO 120
<211> LENGTH: 24
<212> TYPE: DNA
<213> ORGANISM: artificial
<220> FEATURE:
<223> OTHER INFORMATION: Synthetic inhibitor sequence

<400> SEQUENCE: 120
ctccatctta gttttcgacc ggct                                            24

<210> SEQ ID NO 121
<211> LENGTH: 53
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (22)..(22)
<223> OTHER INFORMATION: ribose adenine

<400> SEQUENCE: 121
ctccatctta gtttgggtat taggcggaca gccggtcgaa aactaagatg gag           53

<210> SEQ ID NO 122
<211> LENGTH: 28
<212> TYPE: DNA
<213> ORGANISM: artificial
<220> FEATURE:
<223> OTHER INFORMATION: DNAzyme

<400> SEQUENCE: 122
gtccgctccg agccggtcga aaataccc                                        28

<210> SEQ ID NO 123
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 123
tcttagttag gatagttcat                                                 20

<210> SEQ ID NO 124
<211> LENGTH: 31
<212> TYPE: DNA
<213> ORGANISM: artificial
<220> FEATURE:
<223> OTHER INFORMATION: DNAzyme

<400> SEQUENCE: 124
gaactatctc cgagccggtc gaaaactaag a                                    31

<210> SEQ ID NO 125
<211> LENGTH: 24

```
<212> TYPE: DNA
<213> ORGANISM: artificial
<220> FEATURE:
<223> OTHER INFORMATION: Synthetic inhibitor sequence

<400> SEQUENCE: 125
ctccatctta gttttcgacc ggct                                           24

<210> SEQ ID NO 126
<211> LENGTH: 54
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (23)..(23)
<223> OTHER INFORMATION: ribose adenine

<400> SEQUENCE: 126
ctccatctta gttttgggta ttaggcggac agccggtcga aaactaagat ggag          54

<210> SEQ ID NO 127
<211> LENGTH: 28
<212> TYPE: DNA
<213> ORGANISM: artificial
<220> FEATURE:
<223> OTHER INFORMATION: DNAzyme

<400> SEQUENCE: 127
gtccgctccg agccggtcga aaataccc                                       28

<210> SEQ ID NO 128
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 128
tcttagttag gatagttcat                                                20

<210> SEQ ID NO 129
<211> LENGTH: 31
<212> TYPE: DNA
<213> ORGANISM: artificial
<220> FEATURE:
<223> OTHER INFORMATION: DNAzyme

<400> SEQUENCE: 129
gaactatctc cgagccggtc gaaaactaag a                                   31

<210> SEQ ID NO 130
<211> LENGTH: 24
<212> TYPE: DNA
<213> ORGANISM: artificial
```

```
<220> FEATURE:
<223> OTHER INFORMATION: Synthetic inhibitor sequence

<400> SEQUENCE: 130
ctccatctta gttttcgacc ggct                                          24

<210> SEQ ID NO 131
<211> LENGTH: 55
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (24)..(24)
<223> OTHER INFORMATION: ribose adenine

<400> SEQUENCE: 131
ctccatctta gttttcgggt attaggcgga cagccggtcg aaaactaaga tggag        55

<210> SEQ ID NO 132
<211> LENGTH: 28
<212> TYPE: DNA
<213> ORGANISM: artificial
<220> FEATURE:
<223> OTHER INFORMATION: DNAzyme

<400> SEQUENCE: 132
gtccgctccg agccggtcga aaataccc                                      28

<210> SEQ ID NO 133
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 133
tcttagttag gatagttcat                                               20

<210> SEQ ID NO 134
<211> LENGTH: 31
<212> TYPE: DNA
<213> ORGANISM: artificial
<220> FEATURE:
<223> OTHER INFORMATION: DNAzyme

<400> SEQUENCE: 134
gaactatctc cgagccggtc gaaaactaag a                                  31

<210> SEQ ID NO 135
<211> LENGTH: 24
<212> TYPE: DNA
<213> ORGANISM: artificial
<220> FEATURE:
<223> OTHER INFORMATION: Synthetic inhibitor sequence
```

<400> SEQUENCE: 135
ctccatctta gttttcgacc ggct                                           24

<210> SEQ ID NO 136
<211> LENGTH: 55
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (24)..(24)
<223> OTHER INFORMATION: ribose adenine

<400> SEQUENCE: 136
ctccatctaa gttttcgggt attaggcgga cagccggtcg aaaactaaga tggag         55

<210> SEQ ID NO 137
<211> LENGTH: 28
<212> TYPE: DNA
<213> ORGANISM: artificial
<220> FEATURE:
<223> OTHER INFORMATION: DNAzyme

<400> SEQUENCE: 137
gtccgctccg agccggtcga aaataccc                                       28

<210> SEQ ID NO 138
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 138
tcttagttag gatagttcat                                                20

<210> SEQ ID NO 139
<211> LENGTH: 31
<212> TYPE: DNA
<213> ORGANISM: artificial
<220> FEATURE:
<223> OTHER INFORMATION: DNAzyme

<400> SEQUENCE: 139
gaactatctc cgagccggtc gaaaactaag a                                   31

<210> SEQ ID NO 140
<211> LENGTH: 24
<212> TYPE: DNA
<213> ORGANISM: artificial
<220> FEATURE:
<223> OTHER INFORMATION: Synthetic inhibitor sequence

<400> SEQUENCE: 140 ctccatcttag gttttcgacc ggct                                         24

<210> SEQ ID NO 141
<211> LENGTH: 57
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (26)..(26)
<223> OTHER INFORMATION: ribose adenine

<400> SEQUENCE: 141 ctccatcttag gttttcgagg gtattaggcg gacagccggt cgaaaactaa gatggag     57

<210> SEQ ID NO 142
<211> LENGTH: 28
<212> TYPE: DNA
<213> ORGANISM: artificial
<220> FEATURE:
<223> OTHER INFORMATION: DNAzyme

<400> SEQUENCE: 142
gtccgctccg agccggtcga aatacccc                                      28

<210> SEQ ID NO 143
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 143
tcttagttag gatagttcat                                               20

<210> SEQ ID NO 144
<211> LENGTH: 31
<212> TYPE: DNA
<213> ORGANISM: artificial
<220> FEATURE:
<223> OTHER INFORMATION: DNAzyme

<400> SEQUENCE: 144
gaactatctc cgagccggtc gaaaactaag a                                  31

<210> SEQ ID NO 145
<211> LENGTH: 24
<212> TYPE: DNA
<213> ORGANISM: artificial
<220> FEATURE:
<223> OTHER INFORMATION: Synthetic inhibitor sequence

<400> SEQUENCE: 145 ctccatcttag gttttcgacc ggct                                         24

```
<210> SEQ ID NO 146
<211> LENGTH: 57
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (26)..(26)
<223> OTHER INFORMATION: ribose adenine

<400> SEQUENCE: 146
ctccatctaa gttttcgagg gtattaggcg gacagccggt cgaaaactaa gatggag       57

<210> SEQ ID NO 147
<211> LENGTH: 28
<212> TYPE: DNA
<213> ORGANISM: artificial
<220> FEATURE:
<223> OTHER INFORMATION: DNAzyme

<400> SEQUENCE: 147
gtccgctccg agccggtcga aaataccc                                       28

<210> SEQ ID NO 148
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 148
tcttagttag gatagttcat                                                20

<210> SEQ ID NO 149
<211> LENGTH: 31
<212> TYPE: DNA
<213> ORGANISM: artificial
<220> FEATURE:
<223> OTHER INFORMATION: DNAzyme

<400> SEQUENCE: 149
gaactatctc cgagccggtc gaaaactaag a                                   31

<210> SEQ ID NO 150
<211> LENGTH: 24
<212> TYPE: DNA
<213> ORGANISM: artificial
<220> FEATURE:
<223> OTHER INFORMATION: Synthetic inhibitor sequence

<400> SEQUENCE: 150
ctccatctta gttttcgacc ggct                                           24
```

```
<210> SEQ ID NO 151
<211> LENGTH: 55
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (32)..(32)
<223> OTHER INFORMATION: ribose adenine

<400> SEQUENCE: 151
agccggtcga aaactaagat ggaggggtat taggcggact agttttcgac cggct          55

<210> SEQ ID NO 152
<211> LENGTH: 28
<212> TYPE: DNA
<213> ORGANISM: artificial
<220> FEATURE:
<223> OTHER INFORMATION: DNAzyme

<400> SEQUENCE: 152
gtccgctccg agccggtcga aaataccc                                         28

<210> SEQ ID NO 153
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 153
tcttagttag gatagttcat                                                  20

<210> SEQ ID NO 154
<211> LENGTH: 31
<212> TYPE: DNA
<213> ORGANISM: artificial
<220> FEATURE:
<223> OTHER INFORMATION: DNAzyme

<400> SEQUENCE: 154
gaactatctc cgagccggtc gaaaactaag a                                     31

<210> SEQ ID NO 155
<211> LENGTH: 24
<212> TYPE: DNA
<213> ORGANISM: artificial
<220> FEATURE:
<223> OTHER INFORMATION: Synthetic inhibitor sequence

<400> SEQUENCE: 155
ctccatctta gttttcgacc ggct                                             24

<210> SEQ ID NO 156
<211> LENGTH: 44
```

```
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (32)..(32)
<223> OTHER INFORMATION: ribose adenine

<400> SEQUENCE: 156
agccggtcga aaactaagac gtgagggtat taggcggact cacg                    44

<210> SEQ ID NO 157
<211> LENGTH: 31
<212> TYPE: DNA
<213> ORGANISM: artificial
<220> FEATURE:
<223> OTHER INFORMATION: DNAzyme

<400> SEQUENCE: 157
gagtccgctc cgagccggtc gaaaataccc t                                  31

<210> SEQ ID NO 158
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 158
tcttagttag gatagttcat                                               20

<210> SEQ ID NO 159
<211> LENGTH: 31
<212> TYPE: DNA
<213> ORGANISM: artificial
<220> FEATURE:
<223> OTHER INFORMATION: DNAzyme

<400> SEQUENCE: 159
gaactatctc cgagccggtc gaaaactaag a                                  31

<210> SEQ ID NO 160
<211> LENGTH: 24
<212> TYPE: DNA
<213> ORGANISM: artificial
<220> FEATURE:
<223> OTHER INFORMATION: Synthetic inhibitor sequence

<400> SEQUENCE: 160
ctccatctta gttttcgacc ggct                                          24

<210> SEQ ID NO 161
<211> LENGTH: 46
<212> TYPE: DNA
<213> ORGANISM: artificial
```

-continued

```
<220> FEATURE:
<223> OTHER INFORMATION: Synthetic structured chimeric substrate (SCS)
      sequence
<220> FEATURE:
<221> NAME/KEY: misc_RNA
<222> LOCATION: (33)..(33)
<223> OTHER INFORMATION: ribose adenine

<400> SEQUENCE: 161
agccggtcga aaactaagac gcccagggta ttaggcggac tgggcg          46

<210> SEQ ID NO 162
<211> LENGTH: 31
<212> TYPE: DNA
<213> ORGANISM: artificial
<220> FEATURE:
<223> OTHER INFORMATION: DNAzyme

<400> SEQUENCE: 162
cagtccgctc cgagccggtc gaaaataccc t                          31

<210> SEQ ID NO 163
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 163
tcttagttag gatagttcat                                       20

<210> SEQ ID NO 164
<211> LENGTH: 31
<212> TYPE: DNA
<213> ORGANISM: artificial
<220> FEATURE:
<223> OTHER INFORMATION: DNAzyme

<400> SEQUENCE: 164
gaactatctc cgagccggtc gaaaactaag a                          31

<210> SEQ ID NO 165
<211> LENGTH: 20
<212> TYPE: DNA
<213> ORGANISM: artificial
<220> FEATURE:
<223> OTHER INFORMATION: Synthetic inhibitor sequence

<400> SEQUENCE: 165
cgggttctta gttttcgacc                                       20

<210> SEQ ID NO 166
<211> LENGTH: 46
<212> TYPE: DNA
<213> ORGANISM: artificial
<220> FEATURE:
<223> OTHER INFORMATION: Synthetic structured chimeric substrate (SCS)
```

```
             sequence
<220> FEATURE:
<221> NAME/KEY: misc_RNA
<222> LOCATION: (33)..(33)
<223> OTHER INFORMATION: ribose adenine

<400> SEQUENCE: 166
agccggtcga aaactaagac gcccagggta ttaggcggac tgggcg                    46

<210> SEQ ID NO 167
<211> LENGTH: 33
<212> TYPE: DNA
<213> ORGANISM: artificial
<220> FEATURE:
<223> OTHER INFORMATION: DNAzyme

<400> SEQUENCE: 167
gtttatgctc cgagccggtc gaaacccgtt tct                                  33

<210> SEQ ID NO 168
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 168
tcttagttag gatagttcat                                                 20

<210> SEQ ID NO 169
<211> LENGTH: 31
<212> TYPE: DNA
<213> ORGANISM: artificial
<220> FEATURE:
<223> OTHER INFORMATION: DNAzyme

<400> SEQUENCE: 169
gaactatctc cgagccggtc gaaaactaag a                                    31

<210> SEQ ID NO 170
<211> LENGTH: 20
<212> TYPE: DNA
<213> ORGANISM: artificial
<220> FEATURE:
<223> OTHER INFORMATION: Synthetic inhibitor sequence

<400> SEQUENCE: 170
gaagttctta gttttcgacc                                                 20

<210> SEQ ID NO 171
<211> LENGTH: 44
<212> TYPE: DNA
<213> ORGANISM: artificial
<220> FEATURE:
<223> OTHER INFORMATION: Synthetic structured chimeric substrate (SCS)
      sequence
<220> FEATURE:
```

```
<221> NAME/KEY: misc_RNA
<222> LOCATION: (13)..(13)
<223> OTHER INFORMATION: ribose adenine

<400> SEQUENCE: 171
gggatgtgaa gtaggatggg acggtcgaaa actaagaact tcac                    44

<210> SEQ ID NO 172
<211> LENGTH: 35
<212> TYPE: DNA
<213> ORGANISM: artificial
<220> FEATURE:
<223> OTHER INFORMATION: DNAzyme

<400> SEQUENCE: 172
gtcccatctc cgagccggtc gaaacttcac atccc                              35

<210> SEQ ID NO 173
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 173
tcttagttag gatagttcat                                               20

<210> SEQ ID NO 174
<211> LENGTH: 44
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (13)..(13)
<223> OTHER INFORMATION: ribose adenine

<400> SEQUENCE: 174
gggatgtgaa gtaggatggg acaatcgaaa actaagaact tcac                    44

<210> SEQ ID NO 175
<211> LENGTH: 44
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (13)..(13)
<223> OTHER INFORMATION: ribose adenine

<400> SEQUENCE: 175
gggatgtgaa gtaggatggg acggtcgaaa actaaagact tcac                    44
```

```
<210> SEQ ID NO 176
<211> LENGTH: 44
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (13)..(13)
<223> OTHER INFORMATION: ribose adenine

<400> SEQUENCE: 176
gggatgtgaa gtaggatggg acaatcgaaa actaaagact tcac                    44

<210> SEQ ID NO 177
<211> LENGTH: 48
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (15)..(15)
<223> OTHER INFORMATION: ribose adenine

<400> SEQUENCE: 177
gggatgagtg aagtaggatg ggacggtcga aaactaagaa cttcactc                48

<210> SEQ ID NO 178
<211> LENGTH: 44
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (13)..(13)
<223> OTHER INFORMATION: ribose adenine

<400> SEQUENCE: 178
gggatgtgcc gtaggatggg acggtcgaaa actaagaacg gcac                    44

<210> SEQ ID NO 179
<211> LENGTH: 48
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (15)..(15)
<223> OTHER INFORMATION: ribose adenine

<400> SEQUENCE: 179
gggatgagtg ccgtaggatg ggacggtcga aaactaagaa cggcactc                48

<210> SEQ ID NO 180
<211> LENGTH: 31
<212> TYPE: DNA
<213> ORGANISM: artificial
<220> FEATURE:
<223> OTHER INFORMATION: DNAzyme

<400> SEQUENCE: 180
gaactatctc cgagccggtc gaaaactaag a                                  31
```

<210> SEQ ID NO 181
<211> LENGTH: 20
<212> TYPE: DNA
<213> ORGANISM: artificial
<220> FEATURE:
<223> OTHER INFORMATION: Synthetic inhibitor sequence

<400> SEQUENCE: 181
cgtattctta gttttcgacc                                                    20

<210> SEQ ID NO 182
<211> LENGTH: 49
<212> TYPE: DNA
<213> ORGANISM: artificial
<220> FEATURE:
<223> OTHER INFORMATION: Synthetic structured chimeric substrate (SCS)
      sequence

<400> SEQUENCE: 182
ggtcgaaaac taagaatacg ggactacagt tagtagtagc gtatgaggg                   49

<210> SEQ ID NO 183
<211> LENGTH: 36
<212> TYPE: DNA
<213> ORGANISM: artificial
<220> FEATURE:
<223> OTHER INFORMATION: DNAzyme

<400> SEQUENCE: 183
ccctcatacg ctccgagccg gtcgaaacta ctaact                                 36

<210> SEQ ID NO 184
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 184
tcttagttag gatagttcat                                                    20

<210> SEQ ID NO 185
<211> LENGTH: 31
<212> TYPE: DNA
<213> ORGANISM: artificial
<220> FEATURE:
<223> OTHER INFORMATION: DNAzyme

<400> SEQUENCE: 185
gaactatctc cgagccggtc gaaaactaag a                                       31

<210> SEQ ID NO 186
<211> LENGTH: 20
<212> TYPE: DNA
<213> ORGANISM: artificial
<220> FEATURE:

<223> OTHER INFORMATION: Synthetic inhibitor sequence

<400> SEQUENCE: 186
gccactctta gttttcgacc                                              20

<210> SEQ ID NO 187
<211> LENGTH: 42
<212> TYPE: DNA
<213> ORGANISM: artificial
<220> FEATURE:
<223> OTHER INFORMATION: Synthetic structured chimeric substrate (SCS)
      sequence

<400> SEQUENCE: 187
ggtcgaaaac taagagtggc accagactag gccactcata aa                     42

<210> SEQ ID NO 188
<211> LENGTH: 35
<212> TYPE: DNA
<213> ORGANISM: artificial
<220> FEATURE:
<223> OTHER INFORMATION: DNAzyme

<400> SEQUENCE: 188
tttatgagtg gctccgagcc ggtcgaaagt ctggt                             35

<210> SEQ ID NO 189
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 189
tcttagttag gatagttcat                                              20

<210> SEQ ID NO 190
<211> LENGTH: 31
<212> TYPE: DNA
<213> ORGANISM: artificial
<220> FEATURE:
<223> OTHER INFORMATION: DNAzyme

<400> SEQUENCE: 190
gaactatctc cgagccggtc gaaaactaag a                                 31

<210> SEQ ID NO 191
<211> LENGTH: 25
<212> TYPE: DNA
<213> ORGANISM: artificial
<220> FEATURE:
<223> OTHER INFORMATION: Synthetic inhibitor sequence

<400> SEQUENCE: 191
cgacccgtct tagttttcga ccggc                                        25

<210> SEQ ID NO 192
<211> LENGTH: 43
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (34)..(34)
<223> OTHER INFORMATION: ribose adenine

<400> SEQUENCE: 192
ggtcgaaaac taagacgtac tagtactact actagtacgg gaa                        43

<210> SEQ ID NO 193
<211> LENGTH: 34
<212> TYPE: DNA
<213> ORGANISM: artificial
<220> FEATURE:
<223> OTHER INFORMATION: Synthetic structured chimeric substrate
      activator strand (SCS ACT) sequence
<220> FEATURE:
<221> NAME/KEY: misc_RNA
<222> LOCATION: (34)..(34)
<223> OTHER INFORMATION: ribose adenine

<400> SEQUENCE: 193
ggtcgaaaac taagacgtac tagtactact acta                                  34

<210> SEQ ID NO 194
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 194
tcttagttag gatagttcat                                                  20

<210> SEQ ID NO 195
<211> LENGTH: 31
<212> TYPE: DNA
<213> ORGANISM: artificial
<220> FEATURE:
<223> OTHER INFORMATION: DNAzyme

<400> SEQUENCE: 195
gaactatctc cgagccggtc gaaaactaag a                                     31

<210> SEQ ID NO 196
<211> LENGTH: 20
<212> TYPE: DNA
<213> ORGANISM: artificial
<220> FEATURE:
<223> OTHER INFORMATION: Synthetic inhibitor sequence

<400> SEQUENCE: 196

```
gtagctctta gttttcgacc                                           20

<210> SEQ ID NO 197
<211> LENGTH: 43
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (34)..(34)
<223> OTHER INFORMATION: ribose adenine

<400> SEQUENCE: 197
cacgcgtagc ggtcgaaaac taagagctac aataggcgtg agg                 43

<210> SEQ ID NO 198
<211> LENGTH: 31
<212> TYPE: DNA
<213> ORGANISM: artificial
<220> FEATURE:
<223> OTHER INFORMATION: DNAzyme

<400> SEQUENCE: 198
cctcacgctc cgagccggtc gaaattgtag c                              31

<210> SEQ ID NO 199
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 199
tcttagttag gatagttcat                                           20

<210> SEQ ID NO 200
<211> LENGTH: 31
<212> TYPE: DNA
<213> ORGANISM: artificial
<220> FEATURE:
<223> OTHER INFORMATION: DNAzyme

<400> SEQUENCE: 200
gaactatctc cgagccggtc gaaaactaag a                              31

<210> SEQ ID NO 201
<211> LENGTH: 20
<212> TYPE: DNA
<213> ORGANISM: artificial
<220> FEATURE:
<223> OTHER INFORMATION: Synthetic inhibitor sequence

<400> SEQUENCE: 201
tttactctta gttttcgacc                                           20
```

<210> SEQ ID NO 202
<211> LENGTH: 55
<212> TYPE: DNA
<213> ORGANISM: artificial
<220> FEATURE:
<223> OTHER INFORMATION: Synthetic structured chimeric substrate (SCS)
    sequence

<400> SEQUENCE: 202
ccctacgact ttacggtcga aaactaagag taaagtgcaa tagcgtaggg atgaa            55

<210> SEQ ID NO 203
<211> LENGTH: 39
<212> TYPE: DNA
<213> ORGANISM: artificial
<220> FEATURE:
<223> OTHER INFORMATION: DNAzyme

<400> SEQUENCE: 203
ttcatcccta cgtccgagcc ggtcgaaatt gcactttac                             39

<210> SEQ ID NO 204
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 204
tcttagttag gatagttcat                                                  20

<210> SEQ ID NO 205
<211> LENGTH: 31
<212> TYPE: DNA
<213> ORGANISM: artificial
<220> FEATURE:
<223> OTHER INFORMATION: DNAzyme

<400> SEQUENCE: 205
gaactatctc cgagccggtc gaaaactaag a                                     31

<210> SEQ ID NO 206
<211> LENGTH: 20
<212> TYPE: DNA
<213> ORGANISM: artificial
<220> FEATURE:
<223> OTHER INFORMATION: Synthetic inhibitor sequence

<400> SEQUENCE: 206
tctgatctta gttttcgacc                                                  20

<210> SEQ ID NO 207
<211> LENGTH: 49
<212> TYPE: DNA
<213> ORGANISM: artificial

```
<220> FEATURE:
<223> OTHER INFORMATION: Synthetic structured chimeric substrate (SCS)
      sequence
<220> FEATURE:
<221> NAME/KEY: misc_RNA
<222> LOCATION: (38)..(38)
<223> OTHER INFORMATION: ribose adenine

<400> SEQUENCE: 207
aaagccgtga tcggtcgaaa actaagatca gatacatagc ggctttaac                49

<210> SEQ ID NO 208
<211> LENGTH: 35
<212> TYPE: DNA
<213> ORGANISM: artificial
<220> FEATURE:
<223> OTHER INFORMATION: DNAzyme

<400> SEQUENCE: 208
gttaaagccg tccgagccgg tcgaaatgta tctga                               35

<210> SEQ ID NO 209
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 209
tcttagttag gatagttcat                                                20

<210> SEQ ID NO 210
<211> LENGTH: 31
<212> TYPE: DNA
<213> ORGANISM: artificial
<220> FEATURE:
<223> OTHER INFORMATION: DNAzyme

<400> SEQUENCE: 210
gaactatctc cgagccggtc gaaaactaag a                                   31

<210> SEQ ID NO 211
<211> LENGTH: 20
<212> TYPE: DNA
<213> ORGANISM: artificial
<220> FEATURE:
<223> OTHER INFORMATION: Synthetic inhibitor sequence

<400> SEQUENCE: 211
tccaatctta gttttcgacc                                                20

<210> SEQ ID NO 212
<211> LENGTH: 51
<212> TYPE: DNA
<213> ORGANISM: artificial
<220> FEATURE:
<223> OTHER INFORMATION: Synthetic structured chimeric substrate (SCS)
```

```
            sequence
<220> FEATURE:
<221> NAME/KEY: misc_RNA
<222> LOCATION: (39)..(39)
<223> OTHER INFORMATION: ribose adenine

<400> SEQUENCE: 212
caaacgctcc aatcggtcga aaactaagat tggataacta ggcgtttgat g          51

<210> SEQ ID NO 213
<211> LENGTH: 35
<212> TYPE: DNA
<213> ORGANISM: artificial
<220> FEATURE:
<223> OTHER INFORMATION: DNAzyme

<400> SEQUENCE: 213
catcaaacgc tccgagccgg tcgaaagtta tccaa                            35

<210> SEQ ID NO 214
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher

<400> SEQUENCE: 214
tcttagttag gatagttcat                                             20

<210> SEQ ID NO 215
<211> LENGTH: 31
<212> TYPE: DNA
<213> ORGANISM: artificial
<220> FEATURE:
<223> OTHER INFORMATION: DNAzyme

<400> SEQUENCE: 215
gaactatctc cgagccggtc gaaaactaag a                                31

<210> SEQ ID NO 216
<211> LENGTH: 20
<212> TYPE: DNA
<213> ORGANISM: artificial
<220> FEATURE:
<223> OTHER INFORMATION: Synthetic inhibitor sequence

<400> SEQUENCE: 216
atgtatctta gttttcgacc                                             20

<210> SEQ ID NO 217
<211> LENGTH: 51
<212> TYPE: DNA
<213> ORGANISM: artificial
<220> FEATURE:
<223> OTHER INFORMATION: Synthetic structured chimeric substrate (SCS)
      sequence
<220> FEATURE:
```

```
<221> NAME/KEY: misc_RNA
<222> LOCATION: (39)..(39)
<223> OTHER INFORMATION: ribose adenine

<400> SEQUENCE: 217
cacgcctatc ttaggtcgaa aactaagatt catttactag ggcgtgatta g         51

<210> SEQ ID NO 218
<211> LENGTH: 39
<212> TYPE: DNA
<213> ORGANISM: artificial
<220> FEATURE:
<223> OTHER INFORMATION: Synthetic structured chimeric substrate
      activator strand (SCS ACT) sequence
<220> FEATURE:
<221> NAME/KEY: misc_RNA
<222> LOCATION: (39)..(39)
<223> OTHER INFORMATION: ribose adenine

<400> SEQUENCE: 218
cacgcctatc ttaggtcgaa aactaagatt catttacta                        39

<210> SEQ ID NO 219
<211> LENGTH: 36
<212> TYPE: DNA
<213> ORGANISM: artificial
<220> FEATURE:
<223> OTHER INFORMATION: DNAzyme

<400> SEQUENCE: 219
ctaatcacgc ctccgagccg gtcgaaagta aatgaa                           36

<210> SEQ ID NO 220
<211> LENGTH: 34
<212> TYPE: DNA
<213> ORGANISM: artificial
<220> FEATURE:
<223> OTHER INFORMATION: DNAzyme

<400> SEQUENCE: 220
ctaatcacgc ctccgagccg gtcgaaagta aatg                             34

<210> SEQ ID NO 221
<211> LENGTH: 33
<212> TYPE: DNA
<213> ORGANISM: artificial
<220> FEATURE:
<223> OTHER INFORMATION: DNAzyme

<400> SEQUENCE: 221
taatcacgcc tccgagccgg tcgaaagtaa atg                              33

<210> SEQ ID NO 222
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
```

<223> OTHER INFORMATION: conjugated to a fluorophore quencher

<400> SEQUENCE: 222
tcttagttag gatagttcat                                              20

<210> SEQ ID NO 223
<211> LENGTH: 31
<212> TYPE: DNA
<213> ORGANISM: artificial
<220> FEATURE:
<223> OTHER INFORMATION: DNAzyme

<400> SEQUENCE: 223
gaactatctc cgagccggtc gaaaactaag a                                 31

<210> SEQ ID NO 224
<211> LENGTH: 20
<212> TYPE: DNA
<213> ORGANISM: artificial
<220> FEATURE:
<223> OTHER INFORMATION: Synthetic inhibitor sequence

<400> SEQUENCE: 224
tccaatctta gttttcgacc                                              20

<210> SEQ ID NO 225
<211> LENGTH: 51
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (39)..(39)
<223> OTHER INFORMATION: ribose adenine

<400> SEQUENCE: 225
cacgcctgtc ttaggtcgaa aactaagatt catttactag ggcgtgatta g            51

<210> SEQ ID NO 226
<211> LENGTH: 39
<212> TYPE: DNA
<213> ORGANISM: artificial
<220> FEATURE:
<223> OTHER INFORMATION: Synthetic structured chimeric substrate
      activator strand (SCS ACT) sequence
<220> FEATURE:
<221> NAME/KEY: misc_RNA
<222> LOCATION: (39)..(39)
<223> OTHER INFORMATION: ribose adenine

<400> SEQUENCE: 226
cacgcctgtc ttaggtcgaa aactaagatt catttacta                         39

<210> SEQ ID NO 227
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine

```
<220> FEATURE:
<221> NAME/KEY: misc_feature
<222> LOCATION: (20)..(20)
<223> OTHER INFORMATION: conjugated to a fluorophore quencher

<400> SEQUENCE: 227
tcttagttag gatagttcat                                                  20

<210> SEQ ID NO 228
<211> LENGTH: 31
<212> TYPE: DNA
<213> ORGANISM: artificial
<220> FEATURE:
<223> OTHER INFORMATION: Synthetic substrate sequence

<400> SEQUENCE: 228
gaactatctc cgagccggtc gaaaactaag a                                     31

<210> SEQ ID NO 229
<211> LENGTH: 20
<212> TYPE: DNA
<213> ORGANISM: artificial
<220> FEATURE:
<223> OTHER INFORMATION: Synthetic inhibitor sequence

<400> SEQUENCE: 229
atgtatctta gttttcgacc                                                  20

<210> SEQ ID NO 230
<211> LENGTH: 48
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (38)..(38)
<223> OTHER INFORMATION: ribose adenine

<400> SEQUENCE: 230
acgccctatc ttaggtcgaa aactaagatt cattactagg gcgtgatt                   48

<210> SEQ ID NO 231
<211> LENGTH: 34
<212> TYPE: DNA
<213> ORGANISM: artificial
<220> FEATURE:
<223> OTHER INFORMATION: DNAzyme

<400> SEQUENCE: 231
aatcacgccc tccgagccgg tcgaaagtaa tgaa                                  34

<210> SEQ ID NO 232
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
```

```
<222> LOCATION: (20)..(20)
<223> OTHER INFORMATION: conjugated to a fluorophore quencher

<400> SEQUENCE: 232
tcttagttag gatagttcat                                              20

<210> SEQ ID NO 233
<211> LENGTH: 31
<212> TYPE: DNA
<213> ORGANISM: artificial
<220> FEATURE:
<223> OTHER INFORMATION: DNAzyme

<400> SEQUENCE: 233
gaactatctc cgagccggtc gaaaactaag a                                 31

<210> SEQ ID NO 234
<211> LENGTH: 23
<212> TYPE: DNA
<213> ORGANISM: artificial
<220> FEATURE:
<223> OTHER INFORMATION: Synthetic inhibitor sequence

<400> SEQUENCE: 234
atgtatctta gttttcgacc ggc                                          23

<210> SEQ ID NO 235
<211> LENGTH: 47
<212> TYPE: DNA
<213> ORGANISM: artificial
<220> FEATURE:
<223> OTHER INFORMATION: Synthetic structured chimeric substrate (SCS)
      sequence
<220> FEATURE:
<221> NAME/KEY: misc_RNA
<222> LOCATION: (37)..(37)
<223> OTHER INFORMATION: ribose adenine

<400> SEQUENCE: 235
cgccctaatc ttaggtcgaa aactaagata catactaggg cgtgatg                47

<210> SEQ ID NO 236
<211> LENGTH: 31
<212> TYPE: DNA
<213> ORGANISM: artificial
<220> FEATURE:
<223> OTHER INFORMATION: DNAzyme

<400> SEQUENCE: 236
atcacgcctc cgagccggtc gaaagtatgt a                                 31

<210> SEQ ID NO 237
<211> LENGTH: 20
<212> TYPE: DNA
<213> ORGANISM: artificial
<220> FEATURE:
<223> OTHER INFORMATION: Synthetic substrate sequence
<220> FEATURE:
<221> NAME/KEY: misc_feature
<222> LOCATION: (1)..(1)
<223> OTHER INFORMATION: conjugated to a fluorescent label
<220> FEATURE:
<221> NAME/KEY: misc_RNA
<222> LOCATION: (9)..(9)
<223> OTHER INFORMATION: ribose adenine
<220> FEATURE:
<221> NAME/KEY: misc_feature
<222> LOCATION: (20)..(20)
<223> OTHER INFORMATION: conjugated to a fluorophore quencher
```

```
<400> SEQUENCE: 237
tcttagttag gatagttcat                                                    20
```

SIGNAL PROPAGATION BIOMOLECULES, DEVICES AND METHODS

CROSS-REFERENCE TO RELATED APPLICATION

This application is a continuation application of U.S. patent application Ser. No. 14/283,993, filed May 21, 2014, which claims priority to U.S. Provisional Patent Application Ser. No. 61/825,738, filed May 21, 2013, and U.S. Provisional Patent Application Ser. No. 61/861,600, filed Aug. 2, 2013, each of which is incorporated herein by reference.

GOVERNMENT FUNDING

This invention was made with government support under 1027877 and 1028238 awarded by the National Science Foundation. The government has certain rights in the invention.

SUMMARY

This disclosure describes, in one aspect, a structured polynucleotide. Generally, the structured polynucleotide includes five domains. A first domain acts as a toehold for an input DNA logic gate to initiate binding to an SCS biomolecule. A second domain acts as a substrate recognition sequence for an upstream DNA logic gate. A third domain acts as a toehold for a output DNA logic gate to initiate binding of the SCS biomolecule to the gate. A fourth domain acts as an effector sequence to alter the state of the output logic gate. A fifth domain acts as a cage sequence to lock the effector sequence in an inactive state until an input gate binds to the structured polynucleotide.

In some embodiments, the structured polynucleotide can include RNA, DNA, a chimera of RNA and DNA, PNA, or LNA.

In some embodiments, the effector sequence can include at least one detectable label. In some of these embodiments, the detectable label can include a fluorescent label detectable upon release of the effector sequence via a Förster resonance energy transfer (FRET) interaction.

This disclosure describes, in another aspect, a device that includes a structured polynucleotide as summarized above.

In some embodiments, the device can further include a first DNA logic gate and a second DNA logic gate. In such embodiments, the structured polynucleotide can form a signal transmission interface between the first DNA logic gate and the second DNA logic gate. In some embodiments, the first DNA logic gate can include a full deoxyribozyme (hereafter referred to as DNAzyme), a multi-component self-assembling DNAzyme, a strand displacement gate, an aptamer, an aptazyme, or a hairpin assembly gate. In some embodiments, the second DNA logic gate can include, independent of the first DNA logic gate, a full DNAzyme, a multi-component self-assembling DNAzyme, a strand displacement gate, an aptamer, an aptazyme, or a hairpin assembly gate.

In some embodiments of the device, multiple upstream toehold and input-binding domains may be present, such that multiple ordered cleavage events are required to release the effector sequence.

In another aspect, this disclosure describes a nucleic acid-based sensor gate capable of multiplexed, amplified detection of arbitrary target nucleic acid sequences. The nucleic acid strands involved may include DNA, RNA, nucleic acid analogs such as PNA or LNA, or a combination of these. The sensor gate includes two strands: an enzyme strand and an inhibitor strand. The system additionally includes: a fuel strand and a substrate strand. If the sensor gates, fuel strands, and substrate strands are all present in solution, the addition of a particular detection sequence produces an amplified output. The gate structure is such that the section of the gate that detects the input can be varied independently of the part of the gate that cleaves the substrate to produce the output, enabling multiplexed detection of multi-strain pathogen signatures. This can be used to detect target sequences with concentrations in the picomolar range in an isothermal assay. In some embodiments, this device may be used in conjunction with the structured polynucleotide described above.

In some embodiments, the devices described in this disclosure may be used in cells for in situ biodetection, or in conjunction with nucleic acid pre-amplification strategies, target denaturation protocols for detection of targets such as double-stranded DNA, plasmid DNA or viral RNA, or alternative readout technologies such as microsphere-based assays and/or paperfluidic lateral flow devices.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5. Demonstration of a logic computation using DNAzyme displacement gates. A) Diagram of example logic circuit. B) Experimental validation of the corresponding DNAzyme displacement circuit. Responses below the broken line are interpreted as Out=0 and those above are interpreted as Out=1. The circuit responds correctly for each input combination, with a high signal-to-noise ratio. The fluorescence value in the fourth column is higher because both the AND gate and the NOT gate are active simultaneously in this case, resulting in both substrate populations being cleaved to produce a higher overall fluorescence level. D) Oligonucleotide sequences and concentrations for FIG. 5 (Table 5).

FIG. 16. SCS Design 6. (A) This SCS design was a single stem loop design, in which the upstream DNAzyme displaced the stem through hybridization and the activator is located on the 5' side of the SCS. The main difference between this and Design 5 (FIG. 15) is the removal of the 2 bp bubble at the cleavage site, instead ensuring that sequence was also hybridized. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 6, over 30 minutes using DNA only strands. (C) Oligonucleotide sequences and concentrations for SCS Design 6 for DNAzyme cascades (Table 28).

FIG. 22. Multiplexed detection of multiple STEC serotype using OR logic. (A) Scheme of multiplexed modular gate replication. The detector gates for all six STEC target sequence were deployed in the same solution, and since they all share a common reporter module they can all share common fuel and substrate strands. If any of the six STEC target sequences is present, it can activate the corresponding detection gate to produce an output fluorescent signal. This circuit implements OR logic because all detection gates cleave the same substrate, so the output signal is the same for any combination of target sequences. (B) Experimental demonstration of a six-way OR circuit for detecting target sequences indicative of six STEC serotypes: O26, O45, O103, O121, O145 and O157. The entire six-detector system was evaluated to detect each target oligonucleotide in separate experiments, and in the absence of all target sequences. Initially, 100 nM of each detection gate (with 25 nM excess inhibitor), 500 nM of the common fuel strand and 250 nM of the common substrate strand were incubated for 15 minutes. Then, 50 nM of the target sequence of interest was added, and the fluorescence value was observed after a further 30 minutes. We observe high and similar fluorescence values for each of the target sequences, and a low response when no target is present, as required for an OR circuit.

FIG. 28 is Table 6, identifying sequences from multi-layer cascade experiments (FIG. 6B and 6C) and two-layer cascade experiment in DNA background (FIG. 8).

FIG. 29 is Table 7, identifying sequences from demonstration of $1^{st}$ SCS input-output combination (FIG. 7A).

FIG. 30 is Table 8, identifying sequences from demonstration of $2^{nd}$ SCS input-output combination (FIG. 7B).

FIG. 31 is Table 9, identifying sequences from demonstration of $3^{rd}$ SCS inpu-output combination (FIG. 7C).

FIG. 32 is Table 10, identifying sequences from two-layer dengue serotyping circuits (FIG. 9).

FIG. 33 is Table 11, identifying DNA sequences for modular gate experiments. All sequences are listed 5' to 3'. rA=ribose adenine base, /FAM/=fluorescein, /TAM/=TAMRA).

DETAILED DESCRIPTION OF ILLUSTRATIVE EMBODIMENTS

The patent or application file contains at least one drawing executed in color. Copies of this patent or patent application publication with color drawing(s) will be provided by the Office upon request and payment of the necessary fee.

DNA computation holds considerable promise for developing autonomous nanoscale devices for biomedical applications. DNA itself has innate advantages toward this end, in its biocompatibility, ease and cost of production, and available modeling software to enable structural and sequence-based predictions. DNA-based computation can be accomplished in vitro using a number of approaches including, for example, strand displacement cascades (e.g., Qian et al., 2011, *Nature* 475 (7356):368-372), hairpin assembly reactions (e.g., Li et al., 2011, *Nucl. Acids Res.* 39(16):e110), parallel arrays of DNAzyme gates (e.g., Pei et al., 2010, *Nat. Nanotechnol.* 5(11):773-777), and multi-component DNAzymes (e.g., Elbaz et al., 2009, *Nat. Nanotechnol.* 15(14):3411-3418). Each approach has unique strengths such as, for example, circuit breadth and depth, computation time, signal amplification, and/or circuit fidelity. Interoperability between approaches, however, remains limited. As DNA computing applications become more sophisticated, integrating different components into a hybrid circuit can enable greater flexibility in design and function than is currently possible for circuits produced from a single type of component.

In order to combine different DNA computing components in a single system, they must be able to communicate with each other. In integrated electronic circuits, wires serve as the interface that connects all the transistors, capacitors, and other components to each other. This disclosure describes a biomolecular equivalent: interface molecules which enable signal transmission between different kinds of DNA computing circuit components. There are a number of criteria to consider: (1) the design should be modular so that the same structure can be replicated with different nucleotide sequences in order to scale up circuits, (2) the molecules should produce minimal circuit leakage and robust signaling, (3) they should enable interfacing between a variety of different circuit components, and/or (4) there should be a viable route to deploy these molecules in practical bioassays. We characterize, experimentally, a modular molecular interface mechanism for DNA computation based on a structured chimeric substrate (SCS) that addresses these criteria.

Design and Cascading of the SCS

Figure 1:
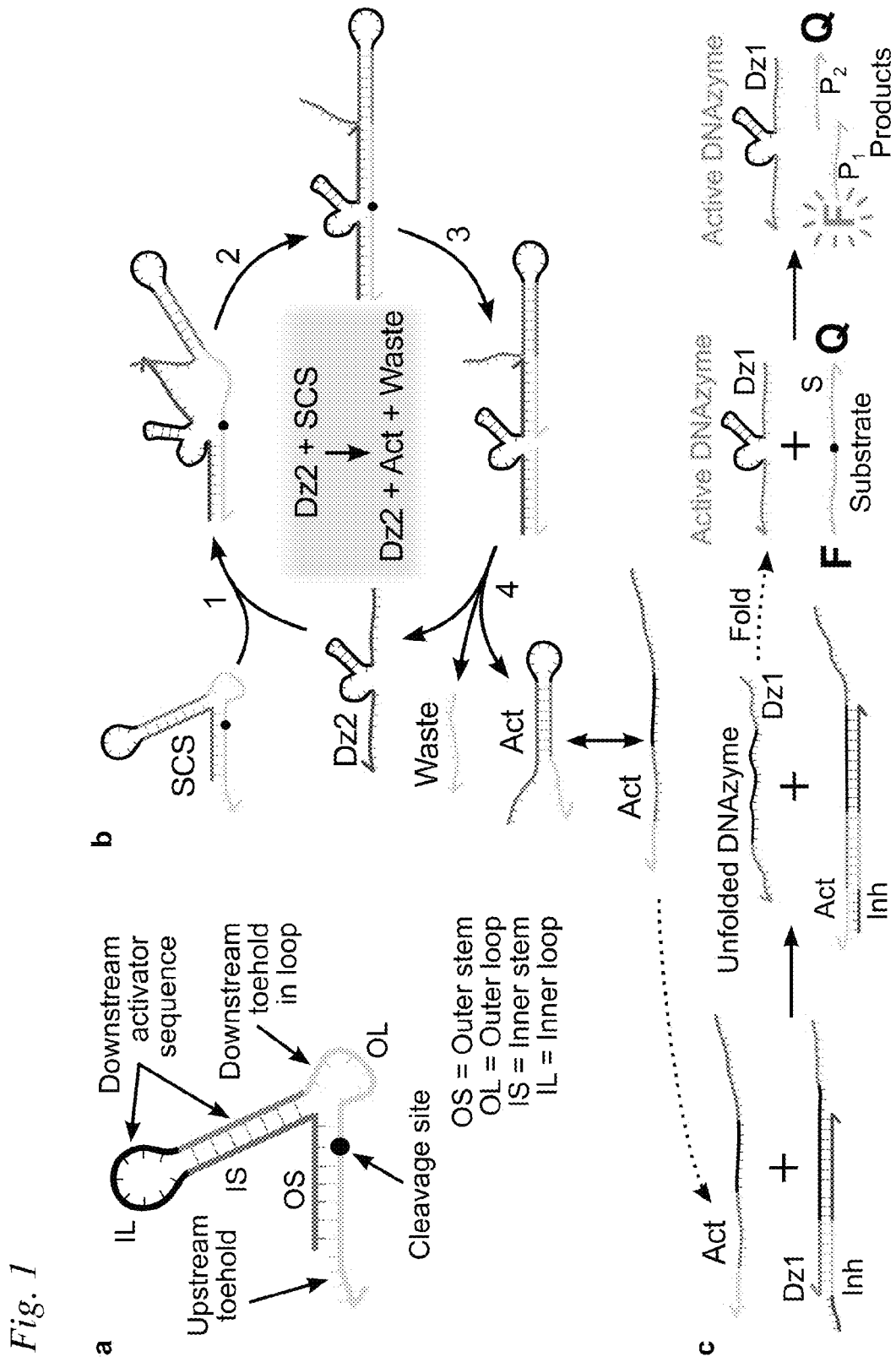
FIG. 1. SCS design and mechanisms for SCS cleavage and DNAzyme displacement. a) Design of a structured chimeric substrate (SCS) to enable signaling between DNAzymes. The SCS consists of an outer stem and loop, which make up the upstream DNAzyme binding domain (red), and an inner stem and loop, which sequester a downstream activator sequence (blue and black). The cleavage site is located towards the inner end of the outer stem. The grey cage sequence is chosen to fold into the desired structure, producing a topological constraint on the downstream reaction kinetics that is undone when the SCS is cleaved by the upstream DNAzyme. b) Mechanism of cleavage of the SCS by an upstream DNAzyme (Dz2). The upstream DNAzyme binds to the outer stem and loop by toehold-mediated strand displacement. The cleavage reaction produces a waste strand and an activator strand (Act). In the activator structure, the outer loop has been released from the topological constraint previously imposed by the outer stem, making the downstream toehold in the outer loop available to bind with a downstream circuit element. c) DNAzyme displacement reaction mechanism. The catalytic activity of the downstream DNAzyme strand (Dz1) is inhibited by hybridization to a partially complementary inhibitor strand (Inh) with a short overhanging toehold. Activation is by a toehold-mediated strand displacement reaction: the input strand (Act) binds to the complex (Dz1-Inh) via the toehold. The input initiates a branch-migration reaction that eventually displaces a catalytically active downstream DNAzyme strand (Dz1), leaving an inert waste complex (Act-Inh). The DNAzyme strand then folds into a catalytically active conformation and proceeds to bind to substrate molecules (S) and cleave them, producing shorter cleavage products (P1 and P2). The cleavage reaction causes separation of the fluorophore-quencher pair attached to the two ends of the substrate, observed as an increase in bulk fluorescence due to loss of FRET.

Our structured chimeric substrate employs a dual stem-loop design, as shown in FIG. 1A. We employ techniques for designing metastable molecules and controlling their reaction pathways. The outer stem and loop domain includes a binding region and cleavage site for a particular upstream DNAzyme, while the inner stem and loop domain includes an effector sequence designed to interact with a downstream circuit component. The downstream effector sequence is thermodynamically sequestered by the metastable structure of the SCS. The upstream DNAzyme binds to the outer stem via a toehold-mediated strand displacement (TMSD) reaction and continues binding through the intermediate loop, producing a DNAzyme-substrate complex that allows the SCS to be cleaved at the RNA base. This frees the intermediate loop from the topological constraint previously imposed by the outer stem and produces a small waste strand. The newly-opened loop becomes a toehold, which enables the effector sequence in the internal stem-loop to interact with downstream circuit components via further TMSD reactions.

The use of TMSD reactions allows us to control the reaction pathways involving the SCS molecule. Binding of the upstream DNAzyme and the outer stem of the SCS is mediated by a free toehold and is therefore fast. In contrast, when the downstream effector sequence is sequestered in the pre-cleavage SCS, its toehold is bound up in the internal loop and therefore cannot easily react with its complement. After cleavage, the toehold of the downstream effector sequence is made available, allowing it to react with downstream circuit components via further TMSD reactions.

Figure 2:
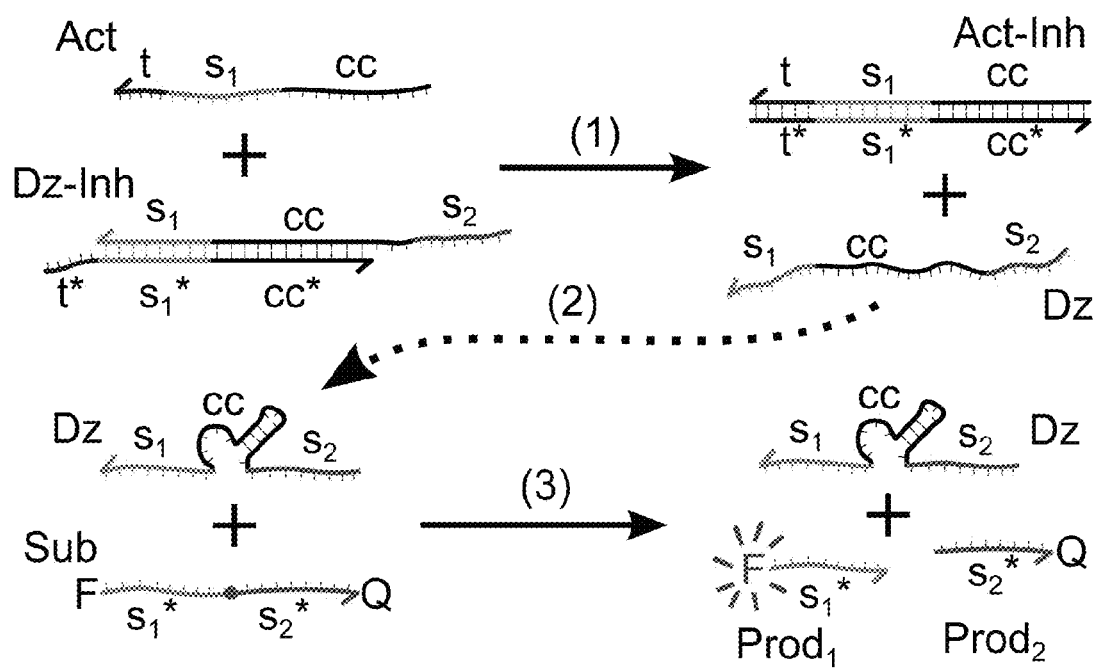
FIG. 2. DNAzyme displacement reaction mechanism. DNAzyme displacement reaction mechanism. The catalytic activity of the DNAzyme strand (Dz) is inhibited by hybridization to a partially complementary inhibitor strand (Inh) with a short overhanging toehold (t*), resulting in an inactive DNAzyme complex (Dz-Inh). The DNAzyme is activated by a toehold-mediated strand displacement reaction: an activator strand (Act) binds to the complex (Dz-Inh) via the t toehold (step 1). The input initiates a branch-migration reaction across the $s_1$ and cc domains that eventually displaces the DNAzyme strand (Dz), leaving an inert waste complex (Act-Inh). The DNAzyme strand then folds into a catalytically active conformation (step 2) and proceeds to bind to substrate molecules (Sub) and cleave them, producing shorter cleavage products (step 3). The cleavage reaction causes separation of the fluorophore-quencher pair attached to the cleavage products ($Prod_1$ and $Prod_2$), which causes an increase in bulk fluorescence due to loss of FRET.
Figure 3:
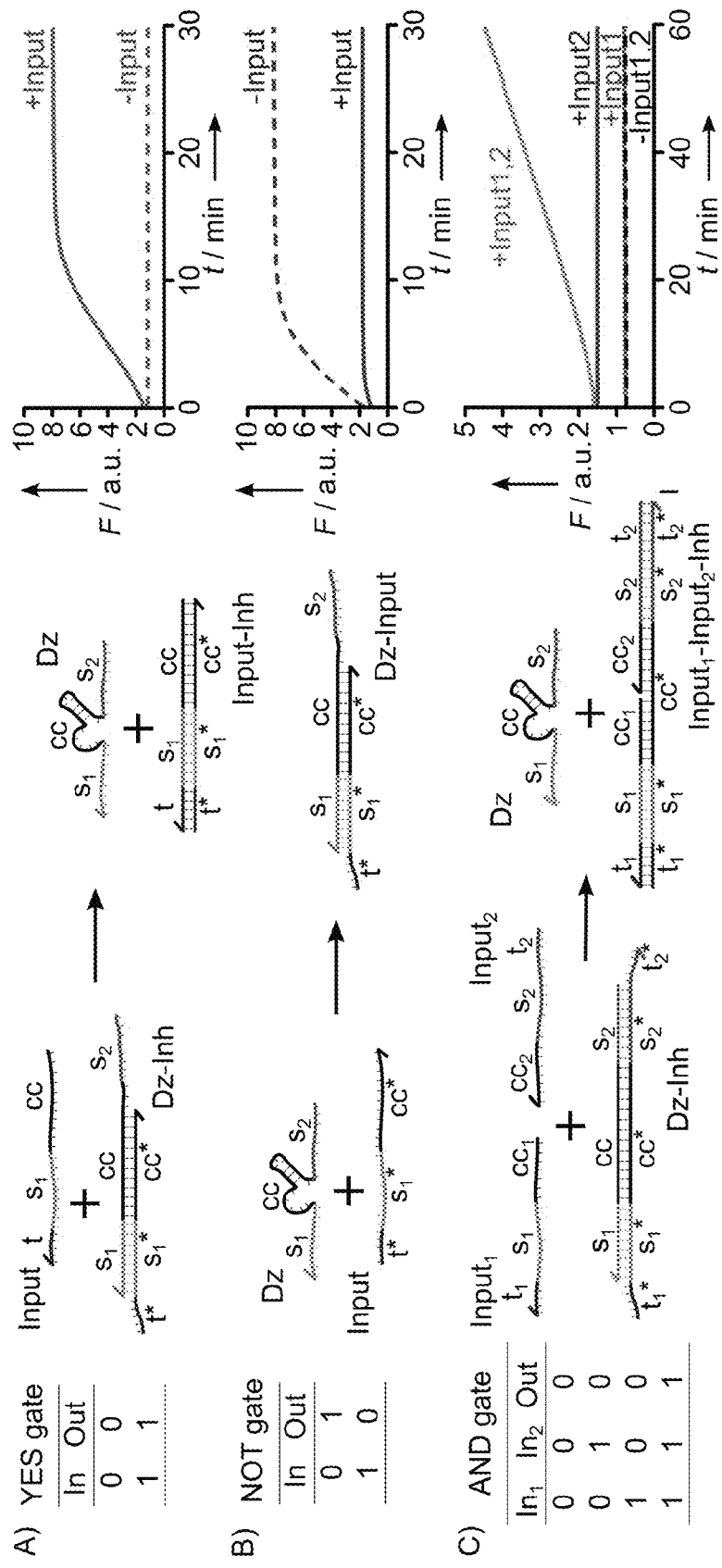
FIG. 3. Logic gates implemented using DNAzyme displacement reactions. A) The YES gate detects its input via the reaction mechanism shown in FIG. 2. B) The NOT gate accepts an inhibitor strand as input, which deactivates a previously active DNAzyme. C) The AND gate has a full-length inhibitor with toeholds ($t_3$ and $t_4$) on each end, and both input strands must be present to release the active DNAzyme via a cooperative strand displacement reaction. D) Oligonucleotide sequences and concentrations for FIG. 3A (Table 1), FIG. 3B (Table 2), and FIG. 3C (Table 3).
Figure 4:
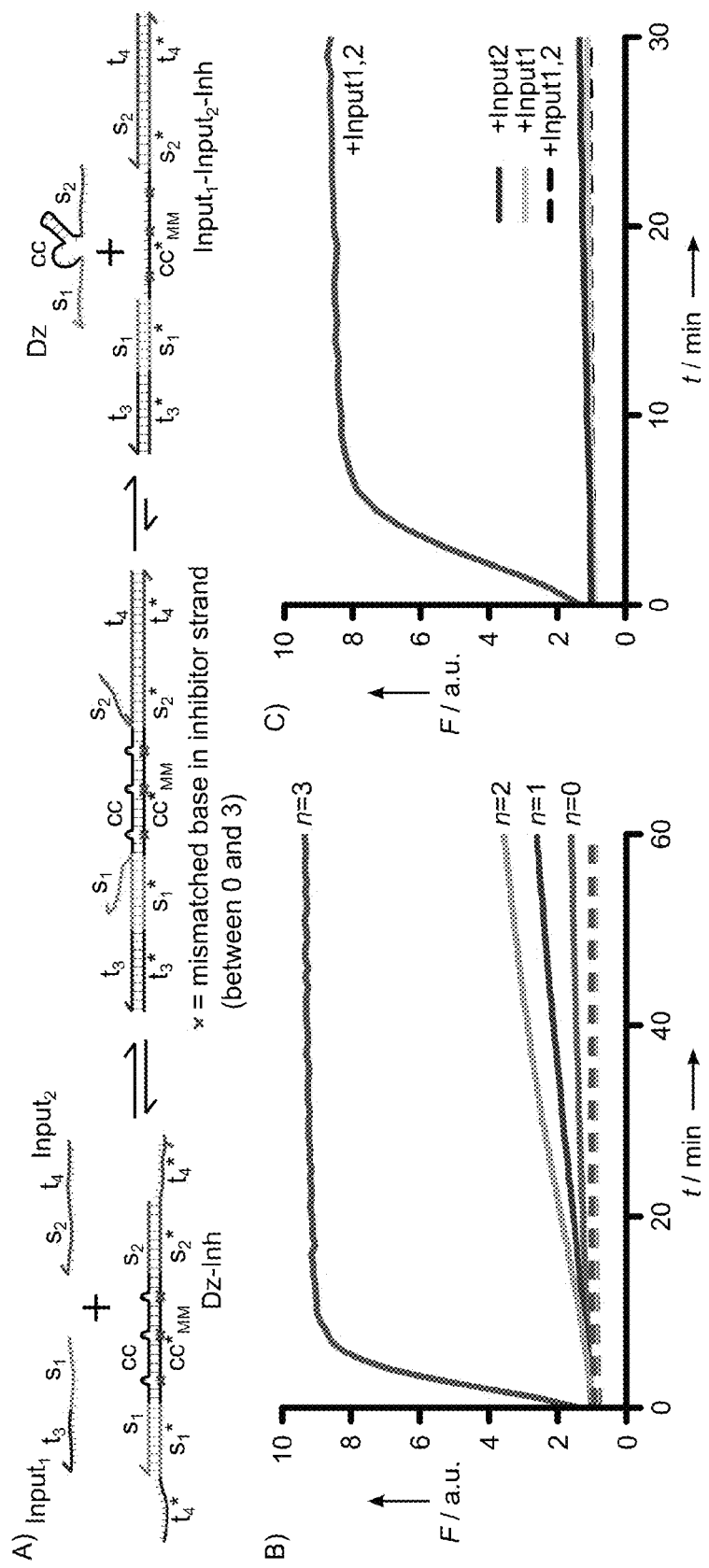
FIG. 4. Detection of arbitrary input sequences using mismatched inhibitors. A) Mechanism for an AND gate that detects two arbitrary input sequences. Since these inputs no longer displace the catalytic core, mismatched bases are added to the part of the inhibitor strand that binds to the core, to encourage unbinding of the DNAzyme strand in the presence of both inputs. B) Kinetic traces for the AND gate design using mismatched inhibitors, for different numbers n=0, 1, 2, 3 of mismatched bases in the $cc^*_{MM}$ domain. For clarity, we only plot the responses with both inputs present (solid lines) and with neither input present (broken lines with corresponding colors). C) Complete characterization of the AND gate with 3 mismatched bases in the $cc^*_{MM}$ domain. We still see very strong inhibition of the AND gate in the presence of a single input, even when 3 mismatches are present in the inhibitor. D) Oligonucleotide sequences and concentrations for FIG. 4 (Table 4).

To demonstrate the combination of TMSD reactions and DNAzyme cleavage, we inhibited an 8-17 DNAzyme (e.g., Bonaccio et al., 2004, *Nucl. Acids Res.* 32(3):916-925) by pre-complexing it with a partially complementary inhibitor strand. As used herein, "inhibit" and variations thereof refer to any measurable decrease in activity. An "inhibitor strand," therefore, refers to a polynucleotide strand that decreases the catalytic activity of an enzymatic polynucleotide such as, for example, a DNAzyme or ribozyme. Pre-complexing the 8-17 DNAzyme with the inhibitor strand blocks one of the substrate binding arms and binds partway into the catalytic core to disrupt its secondary structure, as shown in FIG. 2. The inhibitor strand has a free toehold so that it can be easily removed by a complementary activator strand via a TMSD reaction. We refer to such reactions as DNAzyme displacement (DzD) reactions because this setup allows an incoming activator strand to displace a catalytically active DNAzyme from the complex, which may now cleave its substrate molecules. We have demonstrated DNAzyme displacement gates to implement a range of logic functions, as shown in FIG. 3. However, as can be seen in FIG. 3, the input strands in these reactions share some sequence constraints in common with the conserved catalytic core sequence (specifically, the black domain). Thus these gate designs cannot be used directly to detect strands with arbitrary input sequences, because such strands could not displace the catalytic core of the DNAzyme from the DNAzyme-inhibitor complex. Therefore, we developed DNAzyme displacement logic gates with rationally introduced mismatched bases in the portion of the inhibitor strand that binds to the catalytic core, such as the AND gate shown in FIG. 4A. Here, the two input strands share no sequence commonality with the catalytic core of the DNAzyme and therefore cannot completely displace the DNAzyme strand from the inhibitor. As shown in FIG. 4B, introducing more mismatches produces a faster response in the presence of both input strands, with three mismatches producing very strong activation. FIG. 4C illustrates a complete characterization of the AND gate with three mismatches for all four possible input patterns, demonstrating that both inputs are required for activation, which corresponds to a correct implementation of AND logic. Furthermore, using multiple substrate molecules with the same fluorophore-quencher pair to provide an implicit OR function, we were able to implement a simple logic circuit using DNAzyme displacement, as shown in FIG. 5.

The DNAzyme displacement mechanism generalizes one described in Eckhoff et al., 2010, *J. Syst. Chem.* 1:13, in which an active peroxidase DNAzyme was released via invader strands. Peroxidase active DNA strands provide signal amplification but do not easily propagate logic in a circuit. Here we extend this concept by releasing a DNAzyme that can propagate logic through the circuit. This is accomplished by designing an appropriate SCS molecule to sequester the activator strand for a downstream inhibited DNAzyme. In this way, we can engineer a signaling interaction between the DNAzymes. Since DNAzymes are capable of multiple turnover, we have a built-in means for signal amplification.

Moreover, the function of the SCS is influenced by the dual stem-loop structure, so it may be possible to change the sequence while retaining the structure and function. This allows one to scale up the circuit size by replicating the SCS design with different sequences. Each n layer of the circuit is defined by the position of the DNAzyme. Thus, additional layers can be added to the reaction at either the n−1 or the n+1 position by altering the SCS sequence (FIG. 1C). This principle allowed one to construct a five-layer DNAzyme-based signaling cascade based on the scheme of DzD reactions described above (FIG. 6A). To our knowledge, this is the longest DNAzyme signaling cascade demonstrated to date. Addition of an input DNAzyme initiates the cascade. This active DNAzyme cleaves the top layer SCS, whose effector sequence activates the inhibited DNAzyme in the next layer down, and so on. The readout is provided by a linear substrate labeled with a fluorophore-quencher pair, which is cleaved by the activated bottom-layer DNAzyme at the end of the cascade. FIG. 6B shows that the rate of the cascade varies in a concentration dependent manner. Development of extended catalytic signalling cascades with a high signal-to-noise ratio is challenging because unwanted signal generated in the absence of input (leakage) is also amplified by downstream circuit elements. Kinetic traces of multi-layer cascades (FIG. 6B) show that the time taken for cascade execution increase with the number of layers. In particular, using lower concentrations in the upstream layers of the cascade with increasing concentrations in each downstream layer can reduce leakage without affecting the maximum output level or a significant sacrifice in speed (FIG. 6C). We ran additional controls using uncleavable SCS molecules demonstrate that cleavage is necessary for signal propagation. Thus, chemical modification of a structured substrate by a DNAzyme can be used to propagate information in a signalling cascade.

Interfacing Between DNA Logic Architectures

Figure 7:
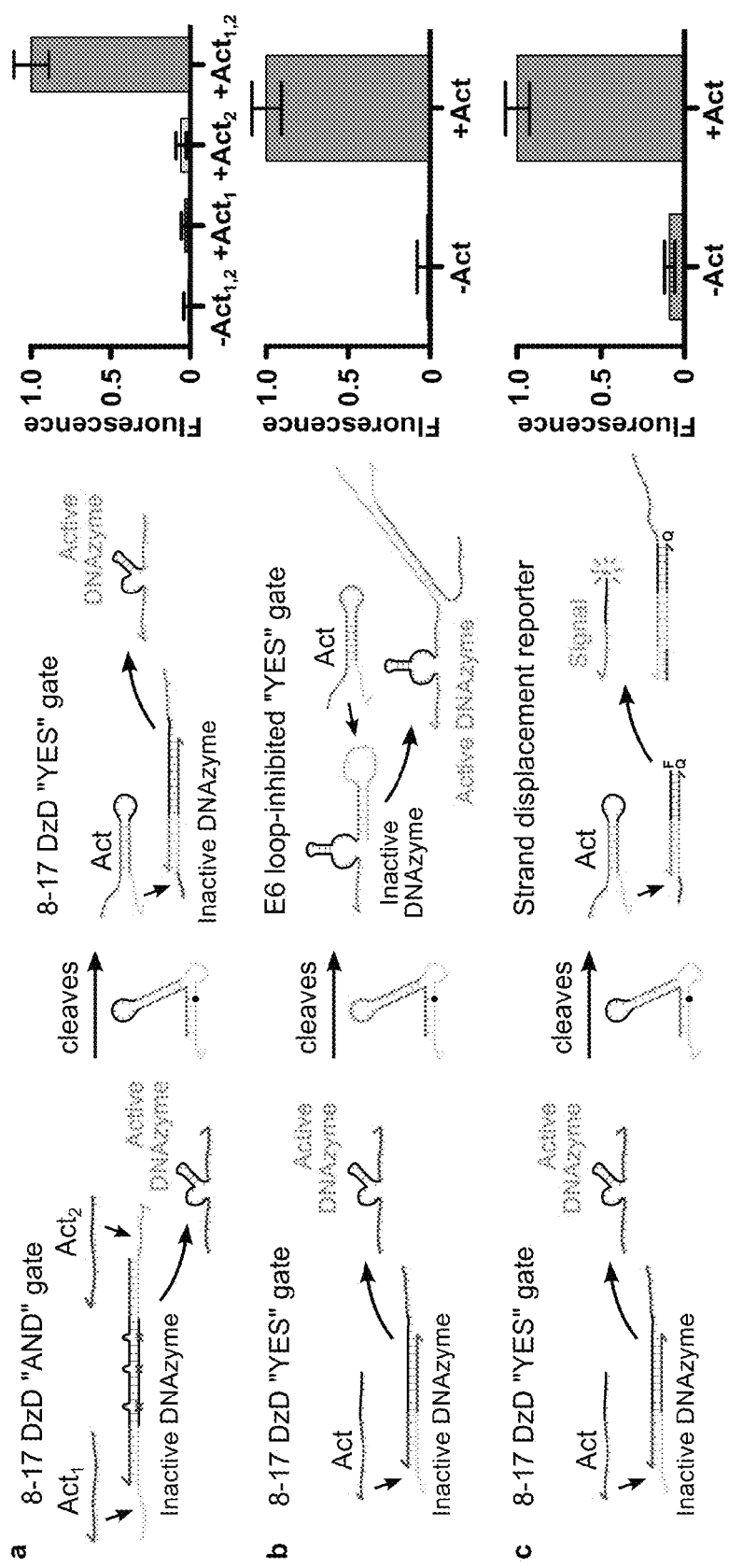
FIG. 7. Application of the SCS as a generic interface molecule. An active DNAzyme from the input module cleaves the SCS, releasing an activator for the output module. This shows that our SCS design enables interoperability between different architectures, which is an important goal for future development of DNA logic circuits. Error bars on bar charts show the 95% confidence interval from triplicate runs of each experiment. a) Input module is a previously reported 8-17 DNAzyme displacement (DzD) "AND" gate with mismatched bases in the catalytic core portion of the inhibitor, which is activated by two inputs in a cooperative strand displacement reaction. Output module is an 8-17 DzD "YES" gate. b) Input module is an 8-17 DzD "YES" gate, output module is a loop-inhibited "YES" gate based on the E6 catalytic motif. Since the E6 DNAzyme cleaves the same dinucleotide junction as the 8-17 DNAzyme, we can use the same fluorescent reporter substrate in this case. c) Input module is an 8-17 DzD "YES" gate, output module is a DNA strand displacement reporter gate in which the activator released by cleavage of the SCS simply displaces a fluorescently-labeled strand from the reporter complex. The advantage of using a strand displacement gate as the reporter is that it does not amplify leakage, which might be preferable for certain applications. More generally, this reaction demonstrates that the SCS design could be used to interface DNAzymes with arbitrary strand displacement circuits and alternative DNAzyme catalytic motifs such as the 10-23 RNA-cleaving DNAzyme and DNA-cleaving DNAzymes.

FIG. 7 illustrates the versatility of our SCS molecule by showing that multiple upstream signal sources can be fed to a variety of downstream circuit components. By designing these input modules based on DNAzymes with the same substrate binding arms and cleavage site, our modular approach allows any of these inputs to be easily exchanged for the other. In conjunction with a downstream output DNAzyme gate activated by a strand displacement reaction, we have demonstrated signal transmission from a variety of input sources. We implemented several logical functions in the input gate, including both AND and YES functions via an 8-17 DNAzyme activated by DNAzyme displacement reactions. The DNAzyme displacement AND gate can operate via a cooperative strand displacement reaction in which two activator strands jointly displace the catalytically active DNAzyme strand (Zhang, D. Y., 2011, *J. Am. Chem. Soc.* 133(4):1077-1086).

FIG. 7 further demonstrates that the signal generated by the SCS can be transmitted to a variety of downstream circuit components including, for example, loop-inhibited DNAzymes, DNAzymes activated by DzD reactions, and TMSD-based reporter complexes. While the multiple turnover activity of downstream enzymatic reactions significantly reduces the response time compared to the TMSD gate, the TMSD gate does not amplify leakage and thus may be preferred for certain applications.

Interchangeable circuit elements, such as the SCS described above, have the potential to serve as an intermediary between existing DNA computational architectures. Our SCS approach provides a general means for propagating signals from different upstream DNAzymes to downstream circuit components of various architectures. Moreover, the multiple turnover activity of the upstream DNAzyme can amplify the propagated signal. Given the utility and diversity of DNAzyme behavior, this is a much-needed addition to the DNA computation toolbox.

The modularity of the SCS gives circuits a great deal of design flexibility. In addition to connecting various combinations of various DNA architectures, its structure can be replicated using different input and output sequences to expand circuit breadth and depth. Importantly, its design allows for logic to be implemented at the upstream position, downstream position, or both. This holds considerable promise for future iterations for the expansion of circuit configurations and behaviors.

The sequence design process for SCS molecules can involve using software tools such as NUPACK and ISO (Zadeh et al., 2011, *J. Comput. Chem.* 32(1):170-173; Fanning et al., 2011, *Proceedings of the 2nd ACM Conference on Bioinformatics, Computational Biology and Biomedicine.* ACM). We used these to design suitable sequences that adopt the desired SCS secondary structure, retain sufficient stability to display low leakage rates before cleavage, and display a reasonable degree of downstream activation after cleavage. In other cases, tools that permit modeling the kinetics of complex DNA interactions such as, for example, coarse-grained modeling approaches (e.g., Romano et al., 2013, *J. Chem. Phys.* 138(8):085101) may be used.

Continued design of additional interoperable circuit elements is possible. We have exemplified SCS involved in a wide variety of uses for signal propagation. One can, however, design alternative SCS elements with different behaviors that may, for example, broaden DNA computational power and/or response profiles. Standardizing various independent circuit architectures may advance the overall capabilities of DNA computation and/or their potential use in bioassay development.

Thus, in one aspect, this disclosure describes a structured polynucleotide. Generally, the structured polynucleotide includes a first domain that acts as a toehold for an input DNA logic gate to initiate binding to an SCS biomolecule, a second domain that acts as a substrate recognition sequence for an upstream DNA logic gate, a third domain that acts as a toehold for a output DNA logic gate to initiate binding of the SCS biomolecule to the gate, a fourth domain that acts as an effector sequence to alter the state of the output logic gate, and, a fifth domain that acts as a cage sequence to lock the effector sequence in an inactive state until an input gate binds to the structured polynucleotide.

The structured polynucleotide may be, for example, RNA, DNA, a chimera of RNA and DNA, or any feasible non-natural base substitute that could be used to construct the biomolecular structure while retaining function. Exemplary non-natural base substitutes include, for example, PNA or LNA.

In some embodiments, the effector sequence can include at least one detectable label. Suitable detectable labels include, for example, a fluorescent label detectable upon release of the effector sequence via a fluorescence resonance energy transfer (FRET) interaction, or using quantum dots or fluorescent microspheres.

In another aspect, this disclosure describes a device that includes a structured polynucleotide as described above configured to form a signal transmission interface between a first DNA logic gate and a second DNA logic gate. The first DNA logic gate and the second DNA logic gate can, independently, include a full DNAzyme, a multi-component self-assembling DNAzyme, strand displacement gate, an aptazyme, or a hairpin assembly gate. In certain embodiments, each of the first DNA logic gate and the second DNA logic gate can include a DNAzyme.

Application of DNAzyme Cascades to Bioassay Design

DNA computing has great potential for practical applications in biocompatible sensing, detection, and decision-making, and a first step towards this goal is to develop DNA computing circuits that can operate robustly in non-ideal conditions. Our SCS design is particularly suited to performing logic in the presence of a random DNA background, as its single-stranded nature means that any unwanted interactions with the background can be rapidly reversed by intramolecular reactions.

Figure 8:
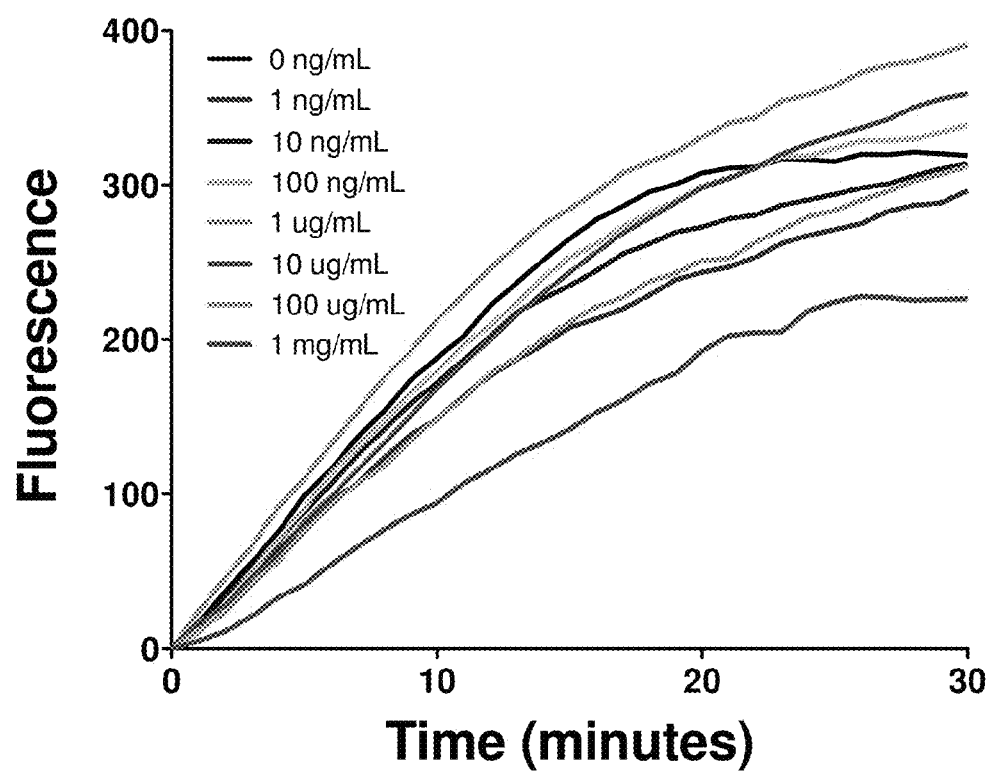
FIG. 8. Operation of DNAzyme signaling cascades in the presence of background DNA. The two-layer DNAzyme displacement cascade experiment was repeated in the presence of various concentrations of herring sperm DNA, covering six orders of magnitude. We observe little systematic difference in the response based on the concentration of background DNA, which suggests that the design of our cascades is robust to interference. The reported fluorescence values have been baseline subtracted with respect to the responses in the absence of the cascade input signal, all of which showed almost no increase in fluorescence.

FIG. 8 demonstrates that DNAzyme signaling systems using our SCS molecule limit interference by random DNA sequences present in, for example, herring sperm DNA, performing equally well in the presence of the background DNA as in its absence. The background DNA may be reducing unwanted cross-reactive sequence interactions in solution, which may improve circuit performance. Furthermore, adsorption of the background DNA to the well surface may reduce ionic interactions that may otherwise sequester computational strands. These results indicate that SCS performance in background makes it an attractive candidate for signal propagation in bioassay development, where interference caused by background DNA sequences can be a major concern.

Figure 6:
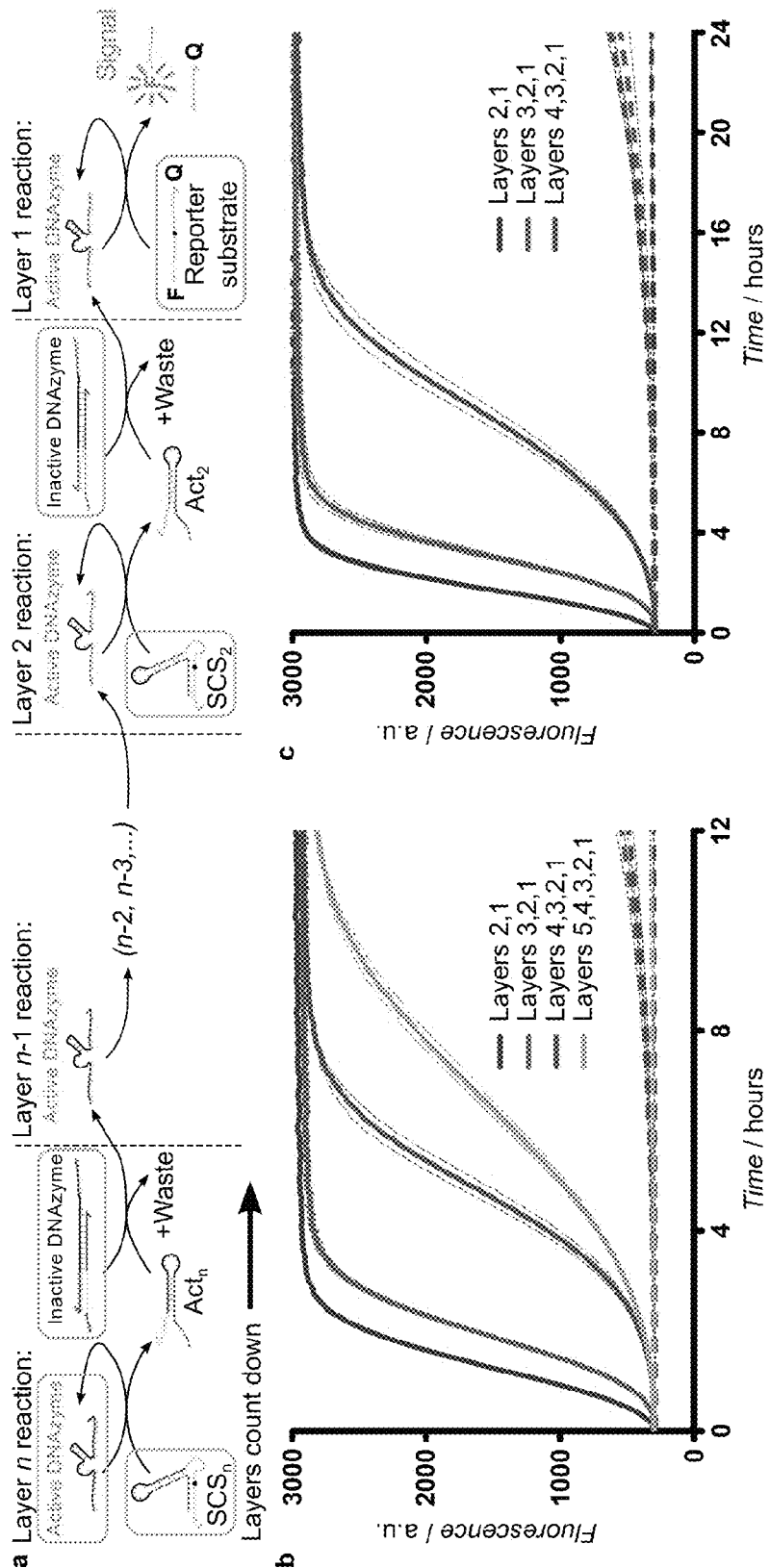
FIG. 6. Demonstration of DNAzyme signaling cascades. a) Schematic of multi-layer DNAzyme signaling cascades using DNAzyme displacement reactions. Initial species for each layer of the cascade are highlighted in grey boxes. In each layer, an active DNAzyme cleaves the corresponding SCS, producing an activator that releases the downstream DNAzyme from its catalytically inactive enzyme-inhibitor complex via a DNAzyme displacement reaction, thereby propagating the activating signal to the next layer of the cascade. b) Mean fluorescence values of two-layer (blue), three-layer (red), four-layer (green) and five-layer (orange) linear DNAzyme signaling cascades with equimolar (100 nM) DNAzyme concentrations in each layer, in the presence (solid line) and absence (dashed line) of the top-layer active DNAzyme. c) Kinetic traces for multi-layer linear DNAzyme signaling cascades with increasing DNAzyme concentrations in each layer (25 nM in fourth layer, 50 nM in third, 75 nM in second, and 100 nM in first) to demonstrate signal amplification. In both plots, dotted lines represent the 95% confidence interval from three replicate experiments.

DNAzyme logic gates can be cascaded to produce larger circuits. The structured chimeric substrate (SCS) molecules illustrated in FIG. 6 can enable signal transmission between DNAzyme logic gates. Cleavage of the SCS by an upstream DNAzyme causes signal propagation by releasing a sequestered downstream activator from the metastable secondary structure of the SCS. This enables the construction of multi-layer signaling cascades and logic circuits capable of more sophisticated decision making, providing a rationally designed, synthetic analog to signaling cascades in cellular regulatory networks (FIGS. 6A and 6B). Detection of flaviviruses, an in particular dengue (DENV), provides a diagnostically important typing problem because of the existence of four DENV serotypes. Some dengue infections develop into potentially life-threatening dengue hemorrhagic fever or dengue shock syndrome, and if an individual is infected by one of the four dengue serotypes and subsequently re-infected by a different serotype, the secondary infection is more likely to progress to the severe disease.

Thus, it is clinically important not only to diagnose dengue infections but also to identify which serotype is responsible. FIGS. 9A and 9B provide data that demonstrates multi-layer logic circuits for DENV detection and serotyping, which require the presence of DNA oligomers corresponding to a serotype-specific target and two conserved targets from the dengue genome to generate an output signal. FIG. 9C shows that none of the serotyping circuits activate in the presence of off-target serotype-specific oligonucleotide inputs, proving that they are in fact serotype specific. These results apply molecular decision making to flavivirus detection and serotyping in a mock assay scenario, which when implemented into an assay can reduce false positives.

For example, the logic-based assay frameworks described above may be used for sequence-specific detection of, for example, viral RNA, which is generally applicable to virus detection. Such methods may be useful for detecting and/or typing of viruses in clinical samples. The methods also may provide for rapid, straightforward tests for viruses for field use by minimally-trained health care workers.

Viral infections are a significant global healthcare burden. Coronaviruses have been associated with recent deadly outbreaks of severe acute respiratory syndrome (SARS) and Middle East respiratory syndrome (MERS). Similarly, highly virulent strains of influenza, such as H5N1 avian influenza, have emerged in recent years. Flaviviruses such as dengue, West Nile virus and St. Louis encephalitis virus are endemic in the tropics and subtropics. As the ranges of the host vectors such as, for example, mosquitos, expand, so too do the human populations at risk for infection by these viral pathogens. For example, West Nile virus has spread throughout the United States since the first cases were reported in 1999. Therefore, rapid and accurate detection of viral pathogens, including, for example, flaviviruses is an important public health concern.

Conventional tests for direct detection of viral RNA (vRNA) typically involve RT-PCR reactions. These are not easily automated and require considerable expertise and expensive laboratory equipment. Indirect tests, such as those based on detection of particular immunoglobulins, are typically cheaper and easier to administer than PCR tests, but are less sensitive and less strain-specific. A need exists, therefore, for a straightforward, accurate, and rapid test that can be routinely administered by clinicians at the point of care. To have an impact in underserved communities, the protocols should be isothermal, single tube assays that require minimal equipment and limited technical expertise. The widespread availability of such tests would improve healthcare outcomes for patients, and the resulting data from increased testing would provide improved surveillance of global virus outbreaks, enabling more effective allocation of resources to combat these diseases.

Molecular logic-based assays for the amplified detection of viral RNA provide a flexible assay framework for virus detection in clinical samples. The advantages of this framework include, for example, the ability to sense multiple targets and combine the information in a single readout to reduce false positives, the ability to isothermally amplify low target concentrations into a detectable signal, straightforward operation for application in the field, and a simple design to enable rapid retargeting against emerging pathogen strains.

Pathogenic viral strains are continually evolving, making it essential that assay frameworks can be rapidly retargeted against new human-adapted strains. The need for practical, accurate virus detection assays in the United States is further driven by increased incidence of tropical viruses such as, for example, Flaviviridae.

The logic-based virus detection assays described herein can include integrated catalytic molecular logic circuits with isothermal RNA amplification. The assay platform can involve techniques such as rolling circle amplification to sense multiple targets at medically relevant viral titers and feed the amplified signals into multi-input molecular logic circuits, e.g., those described above, to produce an integrated response, which one can detect using, for example, fluorescence measurements. The assays can provide low background responses and high signal-to-noise ratios that resist degradation in biological fluids.

The logic-based assay frameworks described herein can provide sequence-specific detection of single-stranded RNA viruses. The assays couple catalytic DNA logic circuits with isothermal pre-amplification technologies to detect vRNA in clinical samples by direct hybridization. The use of DNA logic circuits as a readout technology allow one to combine detection results from multiple targets in a single-tube assay, to reduce false positives.

Using DNA-based logic circuits for virus detection is innovative in at least three respects. First, the approach enables direct, sequence-specific detection of different viral strains based on recognition of signature RNA sequences in conjunction with isothermal pre-amplification, enabling similar sensitivities to RT-PCR but without the need for repeated thermal cycling. Second, the ability to combine multiple DNA logic elements into circuits will enables one to integrate signals from multiple targets, enabling more sophisticated information processing and decision making than would otherwise be possible (see, e.g., FIG. 9). This capability could be used to sense multiple different parts of a viral genome before returning a single binary response using "AND" logic, which could reduce false positives due to cross-reactivity with other pathogens or due to unwanted signal generation from spurious circuit activation. Alternatively, "OR" logic could provide additional targets, to detect viruses despite sequence variation. Third, since DNA-based devices can be redesigned with similar structures and functions but different nucleotide sequences, a modular DNA sensing device can be rapidly redesigned to detect a different target, enabling rapid development of sensor systems to detect emerging pathogens. Thus, the DNA-based logic circuits described above can provide simple, sequence-specific tests that are suited for rapid development cycles. The circuits also can be suitable for use in field assays because the circuit components are predominantly made of DNA, which can tolerate a wide range of temperatures and can be stored for extended periods without degradation.

For example, the circuits described herein can be integrated into a device for amplified isothermal detection of vRNA in clinical samples. The device would not necessarily compete with the most sensitive PCR-based tests, but rather provide a strain-specific assay based on direct hybridization that is simple and sensitive enough to be deployed as, for example, a field test kit—e.g., as an alternative to serologic tests based on immunoglobulin detection—and that can be easily redesigned to detect emerging strains.

Design of Structured Chimeric Substrate (SCS) Molecules

The considerations for SCS design are mechanistic: an upstream DNAzyme must cleave the SCS and this cleavage product must activate a downstream DNAzyme. Additional considerations include the kinetic rates of the mechanistic objectives. Specifically with respect to interactions with the downstream gate, the pre-cleaved SCS should bind at a low kinetic rate (leakage), while the post-cleaved SCS product should bind at a high kinetic rate (activation). These rates are determined by the relative thermodynamic stability of the hybridization interactions and by kinetic factors, e.g., availability of toeholds, toehold lengths, etc. Pre-cleavage, retention of the secondary structure of the SCS via intramolecular interactions should be thermodynamically favorable. Post-cleavage, the interaction of the SCS product and the downstream inhibitor should be thermodynamically favorable. The SCS structure, therefore, was designed to balance the thermodynamic stability of the pre-cleaved state to minimize leakage and the post-cleaved state to maximize activation.

These rates are not symmetrical, however. Activation is a complex, multi-step process. This begins with a binding step between the upstream DNAzyme and the SCS. After the DNAzyme is stably bound, it then hydrolyzes the RNA base. This is the rate of cleavage by the DNAzyme, which can be affected by many factors such as, for example, the type of DNAzyme used, buffer conditions, and/or orientation of the DNAzyme-substrate complex. The DNAzyme then dissociates from the cleaved products, a rate dependent on the length of the DNAzyme binding arms. Stable rebinding of these sequences after dissociation is highly unlikely, due to the short product hybridization lengths and relatively low initial concentrations in solution. Finally, the activator is now available to hybridize to the toehold of the downstream inhibitor and undergo strand displacement, although there may be some weak secondary structure in the activator strand which will affect the rate of the downstream activation reaction. After the downstream DNAzyme is released, there is a subsequent binding, cleavage, and product dissociation step of the corresponding substrate, which may be another SCS or may be a linear FRET substrate for readout of the final system state. The rate of substrate cleavage of the activation pathway reflects the combined rate from all of these steps and can be treated as a single rate of activation.

Opposing the rate of activation is the rate of gate leakage, defined in part by the relative thermodynamic stability of the SCS secondary structure and its ability to bind to the downstream inhibitor toehold. If fluctuations or imperfections in the SCS structure were to expose the toehold, the activator sequence would be able to displace the downstream inhibitor (Dz/INH), leading to the productive release of the downstream DNAzyme (Dz). Although the individual rates of each of these steps correspond to the same steps in activation, the lack of SCS cleavage means the entire sequence remains intact during this process. As the additional sequence and structure likely ensures a different rate constant than with the cleavage product, this interaction may not occur in exactly the same manner. Although binding to the toehold remains the most likely mechanism for inhibitor displacement, invasion through the core sequence from DNA breathing may also occur. The rational design process to obtain the structure that best satisfies these constraints is detailed below.

Figure 10:
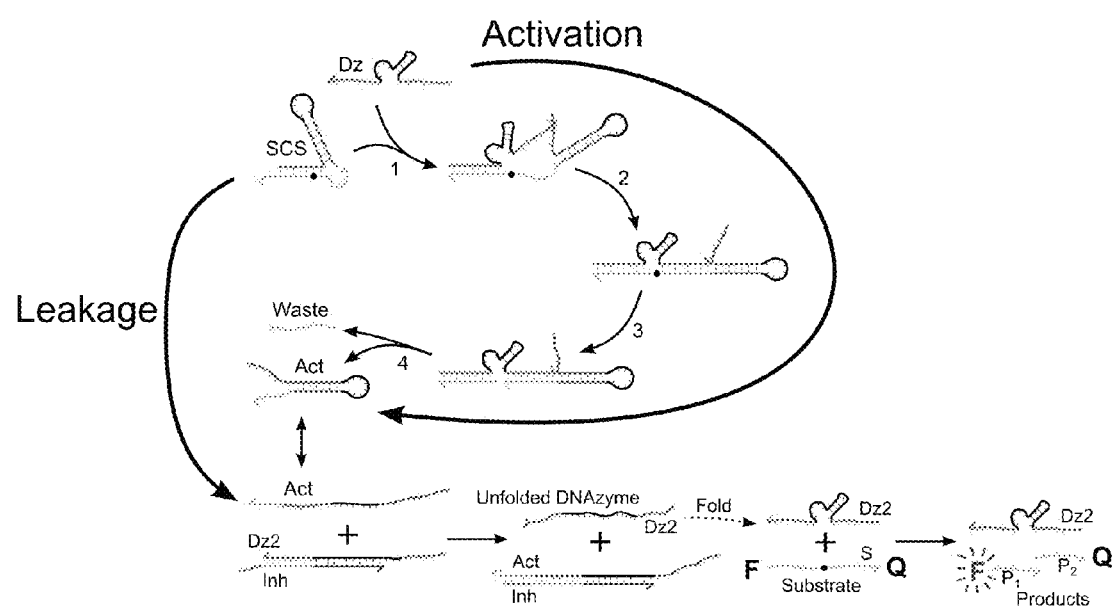
FIG. 10. A schematic mechanism depicting the physical processes associated with both activation (right side) and leakage (left side) rates derived from the SCS structure.

FIG. 10 illustrates a schematic mechanism depicting the physical processes associated with both activation (right side) and leakage (left side) mechanisms illustrated. Although the structure is drawn as a stem loop in this figure, the actual structure varies according to each specific design. The activation rate is defined as the kinetic rate of signal activation, beginning from the addition of the upstream DNAzyme (red). The leakage rate is defined as the kinetic rate of spurious activation of the downstream gate by the SCS in the absence of the upstream DNAzyme. In both cases, the activator is sequestered in the SCS and can hybridize to the downstream inhibitor in the Inactivate DNAzyme complex (bottom strand), which releases the downstream DNAzyme. This DNAzyme can now hybridize and cleave the reporter substrate, leading to a loss of FRET and an increase in fluorescence.

The rational design process of the SCS structure involved determining the most efficient way to sequester the activator sequence, while also enabling cleavage to release the activator. Initially, the activator sequence was 24 bases long, made up of a 5 bp toehold, an 8 bp substrate binding arm, and an 11 bp core sequence. The first two major design iterations used this activator sequence. Subsequent optimization of DNAzyme displacement gates reduced the length of the activator to 20 bases, removing 4 bases from the core displacement sequence. As the DNAzyme displacement gates are regulated by toehold-mediated strand displacement, the availability of the activator toehold was identified as the most likely method for designing the SCS structure that satisfied all prior objectives.

Figure 11:
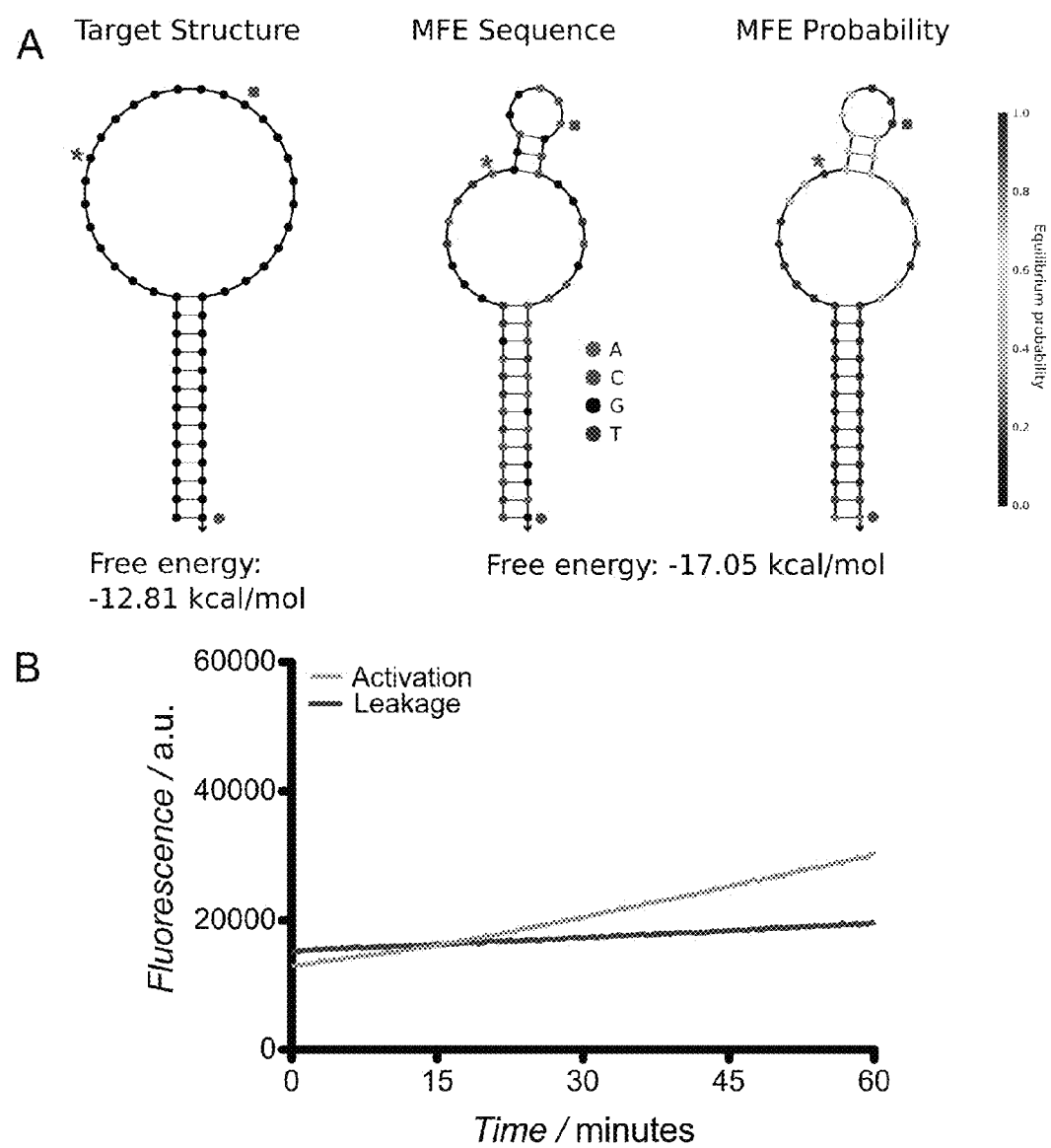
FIG. 11. SCS Design 1. (A) This SCS design was a stem loop design, in which the upstream DNAzyme bound to the loop of the SCS. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 1, over 60 minutes. (C) Oligonucleotide sequences and concentrations for each variant of SCS Design 1 for DNAzyme cascades (Tables 12-20).

The first attempt to design an SCS for communication between two DNAzyme gates used a stem loop structure, with a 26 bp loop and a 13 bp stem (Design 1). Using the 24 bp activator, the toehold and a significant portion of the activator was sequestered in the stem. The remainder of the activator continued into the loop. The loop also contained the RNA cleavage site and substrate binding arms of the upstream DNAzyme (FIG. 11A). The postulated mechanism for this SCS structure was for the upstream DNAzyme to bind to the loop and cleave the RNA base in the loop. This would split the stem loop into two strands, which could then dissociate and diffuse away from each other. Once the strands unbound, the toehold of the activator was free to hybridize to the downstream Dz-Inh complex and displace the inhibitor, releasing an active DNAzyme.

Figure 12:
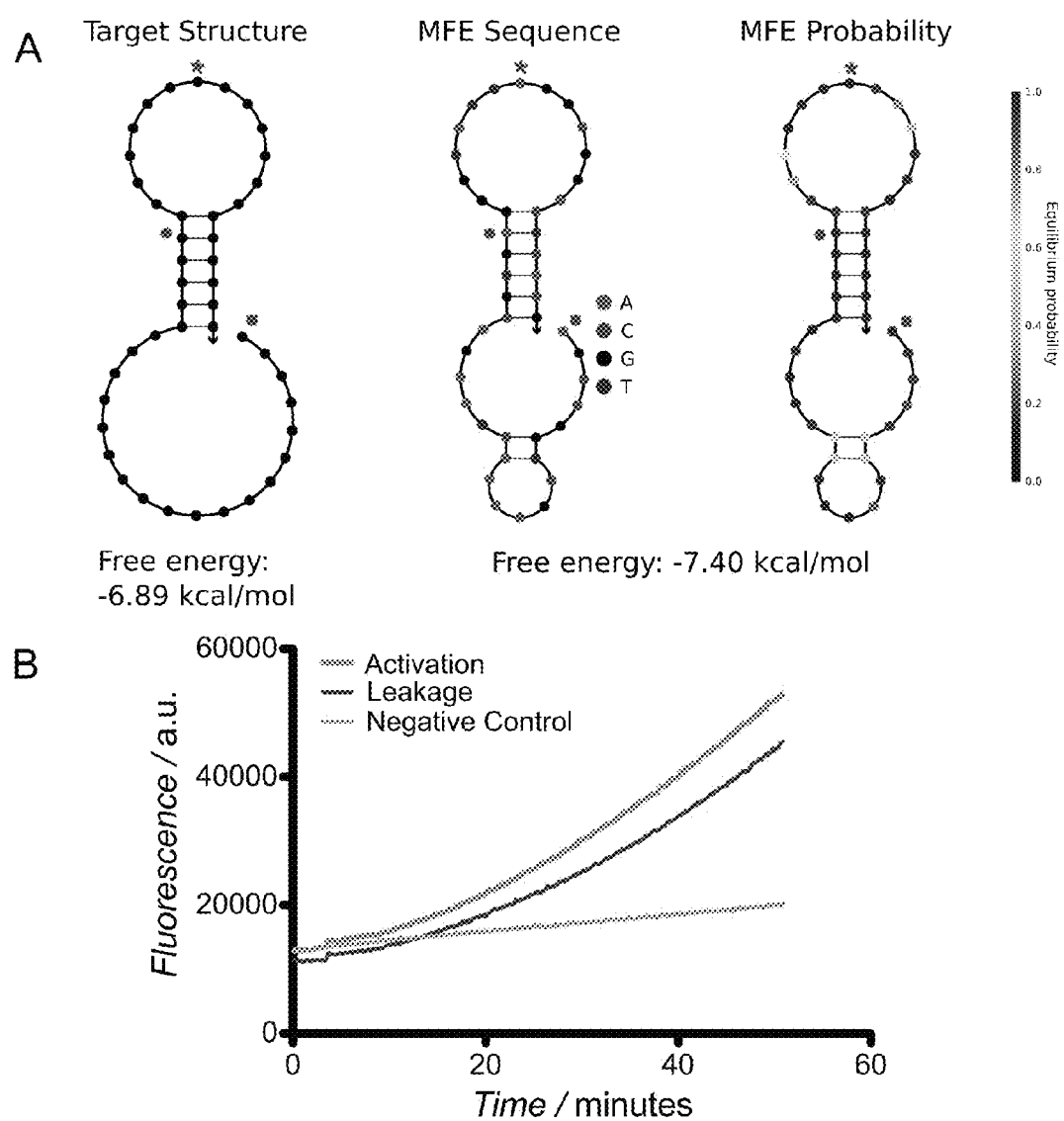
FIG. 12. SCS Design 2. (A) This SCS design was a stem loop design, in which the upstream DNAzyme bound to the loop of the SCS. The main difference between this and Design 1 (FIG. 11) is the orientation of the activation sequence, which is now at the 5' end of the SCS. The target structure (left) was implemented with the given sequence (center) producing the MFE structure (right). The circle denotes the beginning of the activator toehold; the end of the activator sequence is denoted by the square. The star marks the cleavage site. (B) The SCS design in (A), Design 2, over 50 minutes. (C) Oligonucleotide sequences and concentrations for each variant of SCS Design 2 for DNAzyme cascades (Tables 21-22).

Although this design did result in successful cascading (FIG. 11B), the rate of activation was slow for many practical applications and modifications yielded no appreciable improvement on cascade response. This may have been due, at least in part, to the slow rate of product dissociation due to the high stability of the long SCS stem length. Although the SCS structure was likely being cleaved, evidenced by the positive results, the protected toehold may not have been available to bind to the downstream inhibitor, as the complementary stem sequence remained bound even after cleavage. In the next design, the stem loop was shortened to 5 base pairs. The activator was tested in a reverse orientation in SCS structure; the enzyme binding arm and core sequence of the activator was left single-stranded, extending from the 5' side of the SCS while the toehold remained bound in the stem (Design 2, FIG. 12A). Since the complementary sequence on the inhibitor is normally complexed with the downstream DNAzyme, having the activator single stranded for these domains may not result in significant activation, as the toehold binding may still be required to initiate the reaction. This did not significantly improve the cascade signal (FIG. 12B). Although activation was achieved, the rate is slow, perhaps due, at least in part, to the inefficiency of stem loop cleavage. The shorter stem decreased SCS stability, resulting in the increase in gate leakage over time.

Design 1 and Design 2 placed the cleavage site in the middle of the loop, which required the DNAzyme to bind to a structured substrate, as opposed to the typical unstructured FRET substrate. The efficacy of the DNAzyme-catalyzed RNA hydrolysis reaction depends on the DNAzyme holding the RNA base in a specific conformation to rapidly facilitate the base catalysis. The torsional strain of the loop may alter this natural conformation and interaction of the RNA base.

Figure 13:
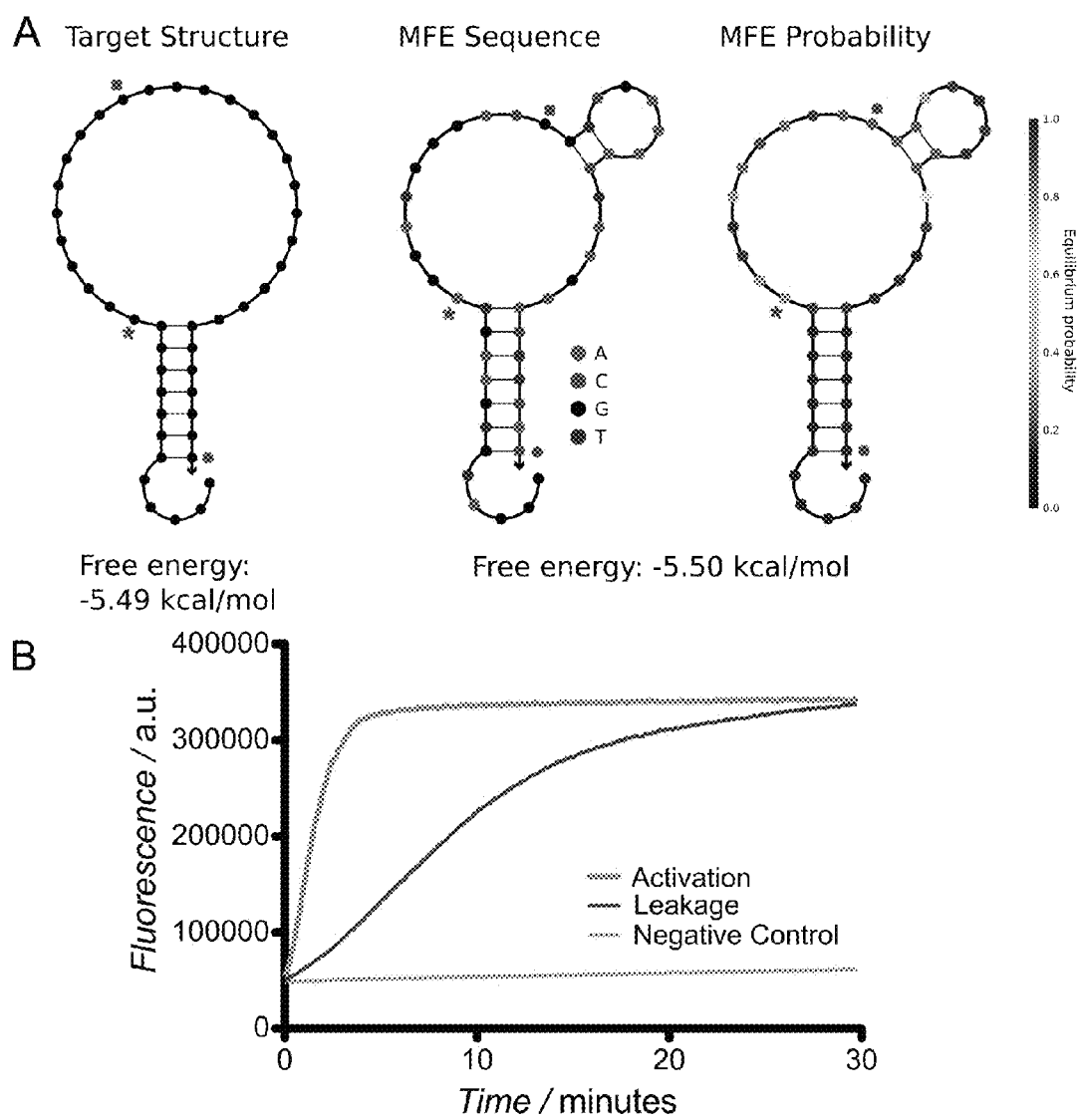
FIG. 13. SCS Design 3. (A) This SCS design was a stem loop design, in which the upstream DNAzyme displaced the stem through hybridization and the activator is located on the 3' side of the SCS. The main difference between this and Design 2 (FIG. 12) is the use of strand displacement for binding of the upstream DNAzyme to its complementary substrate sequence. The target structure (left) was implemented with the given sequence (center) producing the MFE structure (right). The circle denotes the beginning of the activator toehold; the end of the activator sequence is denoted by the square; the star marks the cleavage site. (B) Response of the SCS design in (A), Design 3, over 25 minutes. (C) Oligonucleotide sequences and concentrations for SCS Design 3 for DNAzyme cascades (Table 23).

Binding of the DNAzyme directly to the loop also may alter the ability of the DNAzyme ability to properly orient the RNA base. Thus, we redesigned the SCS structure to use the principle of strand displacement to release the activator (Design 3, FIG. 13A). Here, the 3' binding arm of the upstream DNAzyme hybridizes to a 5' toehold extending from the SCS stem. The substrate binding arm now acts as an invasion strand, displacing the stem loop. The loop then opens and the second binding arm is able to bind to its complementary sequence in the loop, creating a linear substrate properly oriented for RNA cleavage. The cleavage site, now much closer to the stem, can now be efficiently cleaved. Although rapid activation was achieved, the rate of leakage also increased over previous designs, indicating the protection of the toehold was insufficient. (FIG. 13B). This may be due, at least in part, to the short stem and large loop.

Design 3, however, now introduces some sequence constraints into the system, through overlap between the upstream and downstream gates. The stem sequence in Design serves two functions: protection of the downstream toehold and the binding arm displacement sequence for the upstream enzyme. Thus, these two domains must contain the same sequence, which puts a small restriction on the design of this SCS structure. As the downstream toehold and substrate binding arms are normally free to vary, this was determined to be an acceptable constraint as such sequences pose little restriction on the system as a whole.

Design 3 also resulted in successful cascading. The response of this system was, however, completely different from the original designs (FIG. 13B). The system activated extremely quickly compared to Design 1 and the leakage of the system was higher than observed in Design 1. (FIG. 11B). Thus, Design 3 reflects a step toward the kinetic objectives of the system by obtaining a rapid activation rate. The kinetics were influenced, at least in part, by the length of the stem and the size of the loop. A 5 bp stem may be affected by DNA breathing and a large stem (25 bp for Design 3) may make it difficult for SCS to maintain its structure through intramolecular binding by increasing the spacing between hybridization sequences, thus reducing the probability of the ends binding and interacting. Taken together, the activator may be easily deprotected even in the absence of upstream cleavage.

Figure 14:
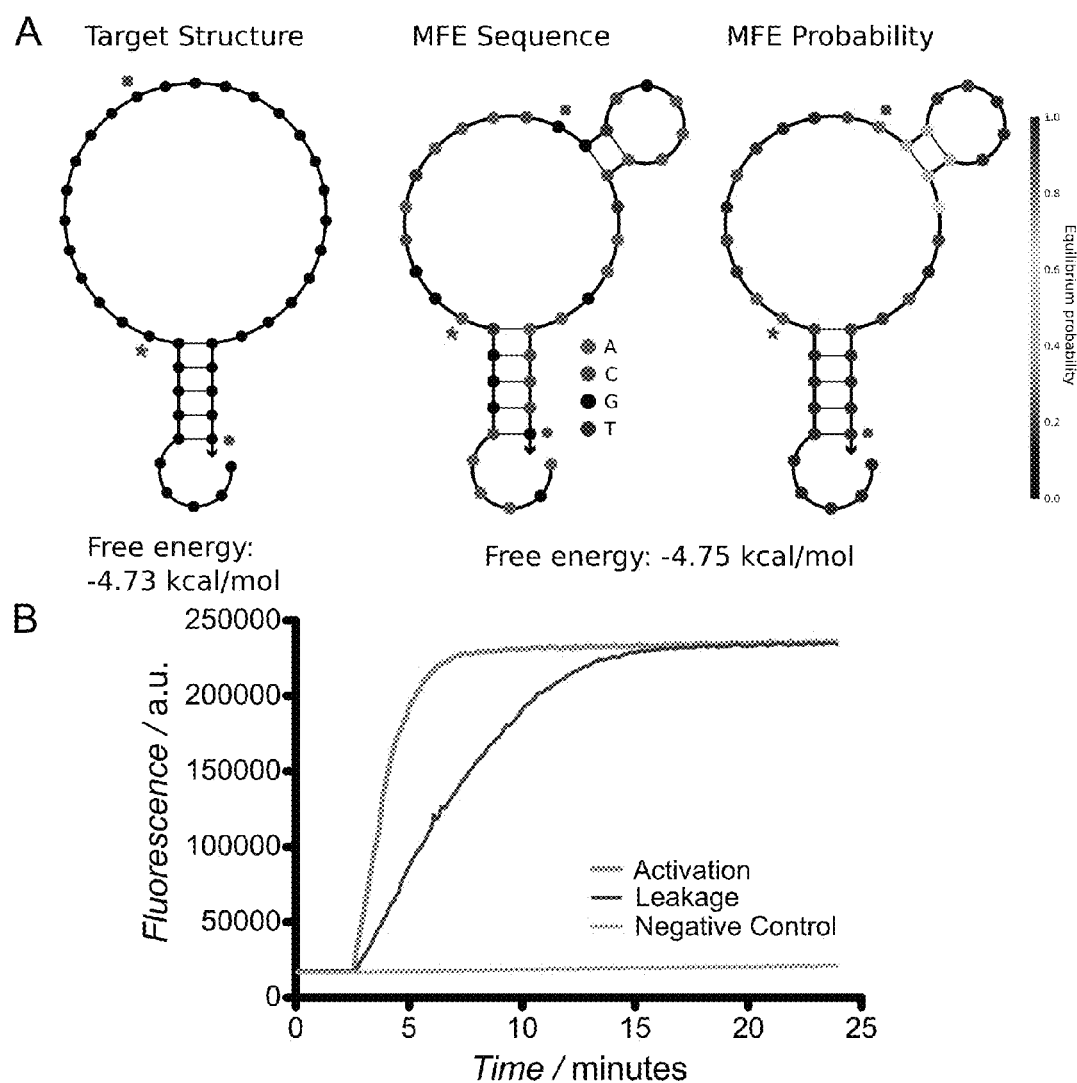
FIG. 14. SCS Design 4. (A) This SCS design was a stem loop design, in which the upstream DNAzyme displaced the stem through hybridization and the activator is located on the 3' side of the SCS. The main difference between this and Design 3 (FIG. 13) is the elongation of the stem and subsequent extension of the upstream DNAzyme binding arms. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 4, over 30 minutes. (C) Oligonucleotide sequences and concentrations for SCS Design 4 for DNAzyme cascades (Table 24) and proposed variants of the SCS Design 4 (Table 25).

Increasing the stem size to 7 bp appeared to slow leakage while maintaining rapid activation (Design 4, FIG. 14), but the use of longer stems can be incompatible with the upstream enzyme strand displacement mechanism desired for achieving a linear substrate. The effects of DNAzyme binding arm length on enzyme activity is well characterized, and the optimal length for rapid product dissociation is 8 bp, which imposed an additional constraint on stem loop design. Had the DNAzyme arms been allowed to extend further, we could have potentially extended the stem to stabilize the structure, which would have been easily displaced by the extended binding arms. However, an 8 bp arm limit ensures that binding, cleavage, and product dissociation can occur at optimal rates, which is promotes multiple turnover. The ability to obtain multiple turnover is one advantage of using DNAzymes for such reactions.

Figure 15:
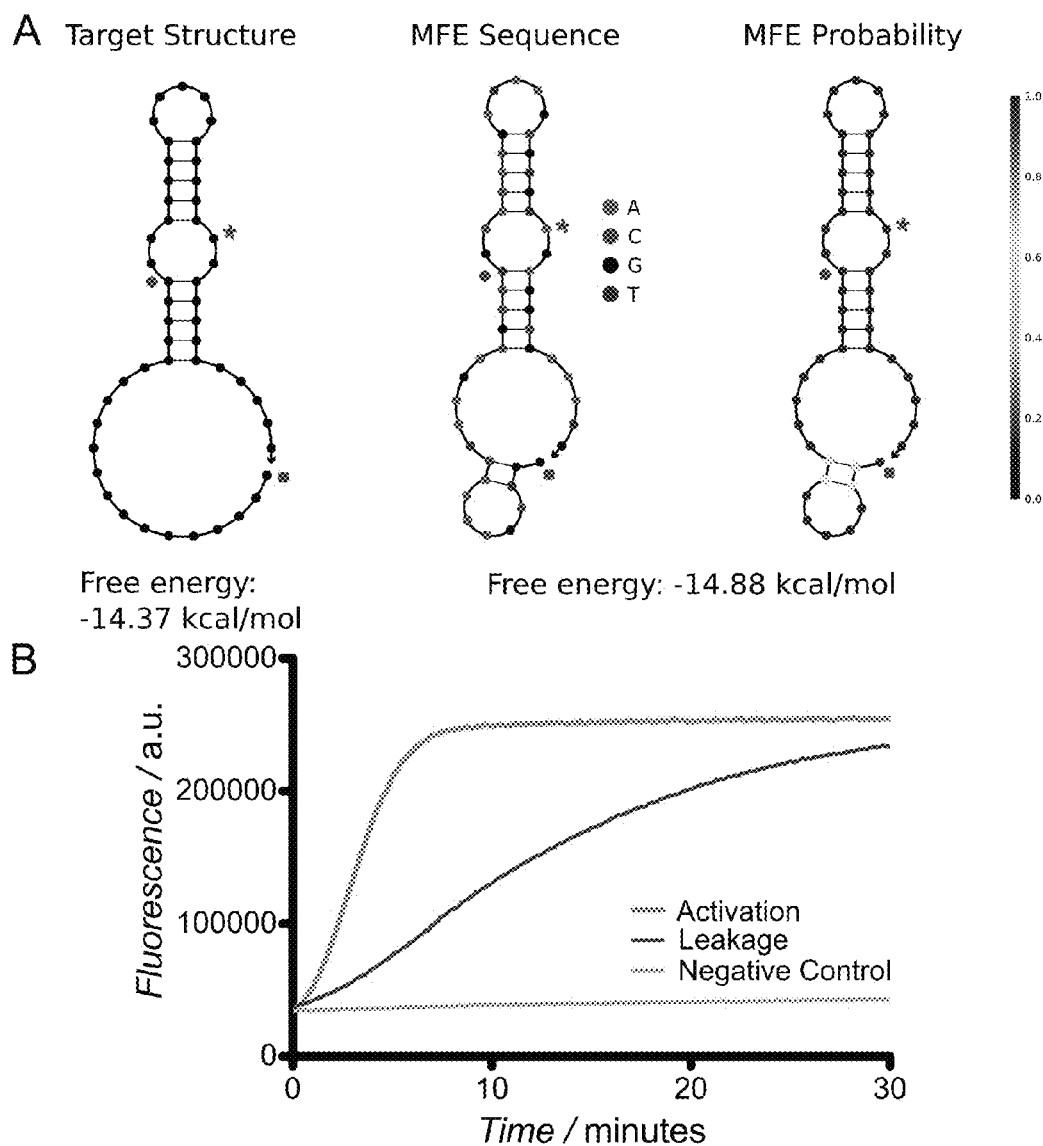
FIG. 15. SCS Design 5. (A) This SCS design was a dual stem loop design, in which the upstream DNAzyme displaced the stem through hybridization and the activator is located on the 5' side of the SCS. The main difference between this and Design 4 (FIG. 14) is the protection of the inner loop with a second stem. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 5, over 30 minutes. (C) Oligonucleotide sequences and concentrations for each variant of SCS Design 5 for DNAzyme cascades (Tables 26-27).

Design 1 and Design 2 provided desirable activator sequestration, while Design 4 and Design 5 provided desirable activator release via cleavage. Thus, each desired activity was achievable, but further design was a matter of determining the right structure to balance each of the complex rates making up the reaction. Design 5 (FIG. 15) reflects a hybrid structure that combines the strand displacement and linear substrate alignment mechanism of Design 3 with the reversed activator orientation of Design 2. An earlier variant of this structure (SCS-D5v2) was unsuccessful (Table 27), as it did not adequately limit leakage. This stem length may be insufficient to properly retain the SCS structure for an extended period of time. With such little overall structure, any isoforms would likely result in incomplete sequestration of the toehold, and therefore would result in activation of the downstream gate, accounting for the leakage.

Positioning the activator as a single-stranded overhang enabled the size of the loop to be reduced. This increases the probability for stem rehybridization after spontaneous dissociation due to DNA breathing and other thermodynamic effects. As short stems were insufficient to properly sequester the activator, Design 5 increased the overall stability of the structure by using additional hybridization to reduce loop size and increase free energy. The cleavage site was left unhybridized, creating a 2 bp bubble, resulting in a dual stem and loop structure. This ensured the retention of 5 bp stems, beneficial for rapid activation, while augmenting the structure with a second short stem to increase overall structure rigidity. The separation into two stems may keep the structure intact through avidity interactions, as the degradation of the structure would only occur after two separate stem dissociation events: the first initiated at the toehold and the second initiated in the inner loop. After cleavage, only the first stem dissociates, which releases the toehold domain, while the second one can refold on itself. As this stem does not participate in the downstream interactions, this is a desirable result. However, the DNA breathing of each stem also may result in a faster displacement, as well as the increase of the loop. In this design, the 5' arm of upstream DNAzyme binds to the 3' toehold of the SCS, initiating displacement of the outer stem. The 3' arm binds to the inner loop, and displaces the inner stem (FIG. 15B). Although significantly more stable than previously designs, this design only moderately improved upon gate leakage.

To further increase the stability of the structure to suppress gate leakage, we removed the 2 bp bubble when creating Design 6, so the cleavage site was also hybridized. The loop size was decreased to a minimal 4 bp, creating a single long stem with a very short loop (FIG. 16A). After binding to the toehold and partially displacing the stem, the second arm is able to bind to the loop of the SCS and displace the rest of the stem, with the cleavage site in the middle of the stem. Although this design performed well (FIG. 16B), it was limited in that it required the use of 10 bp upstream DNAzyme binding arms. This design would present difficulties for scaling up circuit complexity, and 10 bp binding arms also may slow the rate of product release and, therefore, enzyme turnover.

Figure 17:
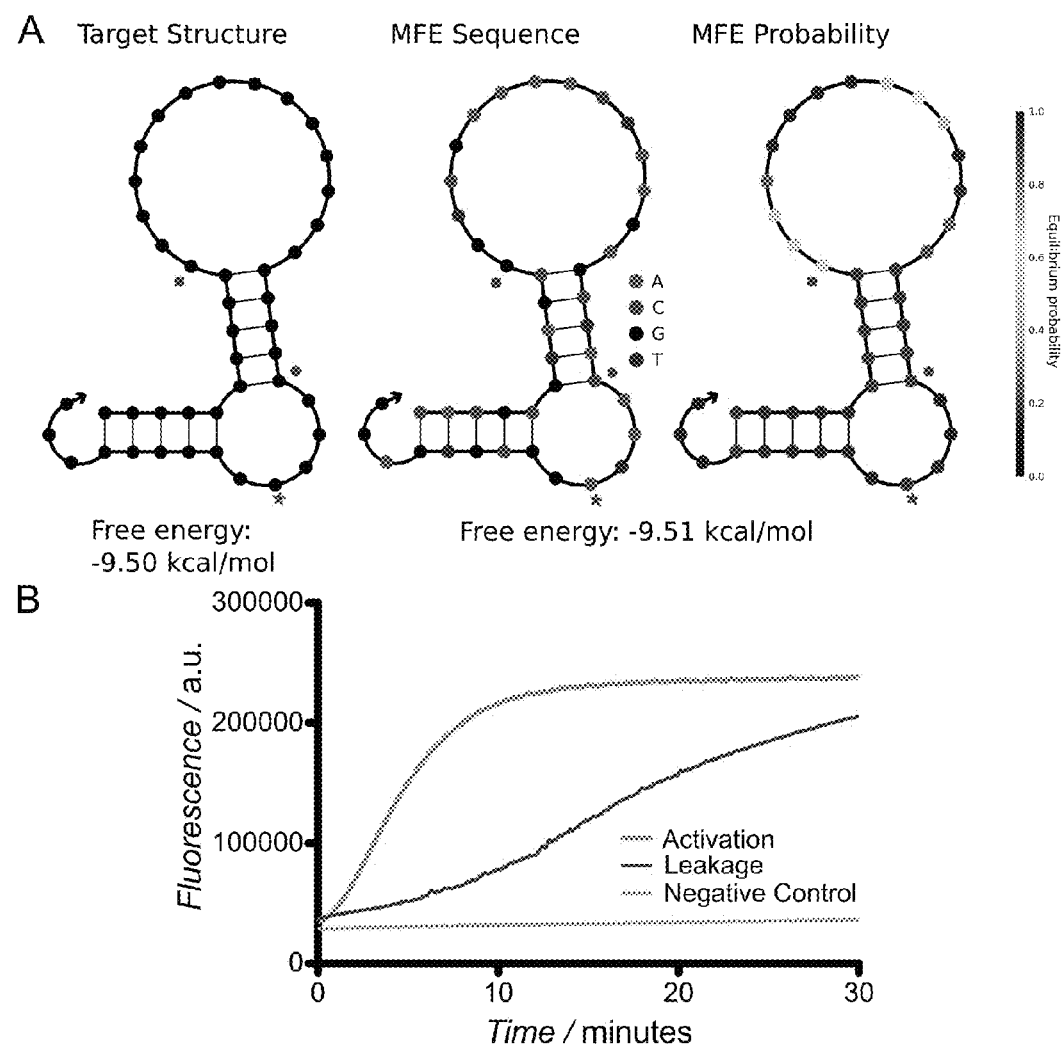
FIG. 17. SCS Design 7. (A) This SCS design was a dual stem loop design, in which the upstream DNAzyme displaced the stem through hybridization and the activator is located on the 3' side of the SCS. The main difference between this and Design 6 (FIG. 16) was the orientation of the activator, which reinstated the dual stem and loop design. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 7, over 30 minutes. (C) Oligonucleotide sequences and concentrations for each variant of SCS Design 7 for DNAzyme cascades (Tables 29-32).

Design 7 moved the activator sequence back to the 3' side of the SCS, ensuring the activator sequence was now bound back up into a loop. In this design, each of the stems were 5 bp, which formed two loops, an inner loop that contained the activator sequence and an outer loop that separated the two stems (FIG. 17A). The cleavage site was placed in the middle of the outer stem. Here, the upstream substrate binding arm hybridizes to the toehold on the 3' side of the stem loop and initiates strand displacement of the outer stem. The other substrate arm binds the outer loop and displaces through the inner still. Cleavage renders the outer stem as a waste product, while the inner stem containing the toehold remains intact. This design relies on the relative instability of the inner stem and loop, so that after the cleavage and dissociation of the outer stem, the inner stem will still activate the downstream gate, despite the toehold theoretically being protected in the stem loop.

Figure 18:
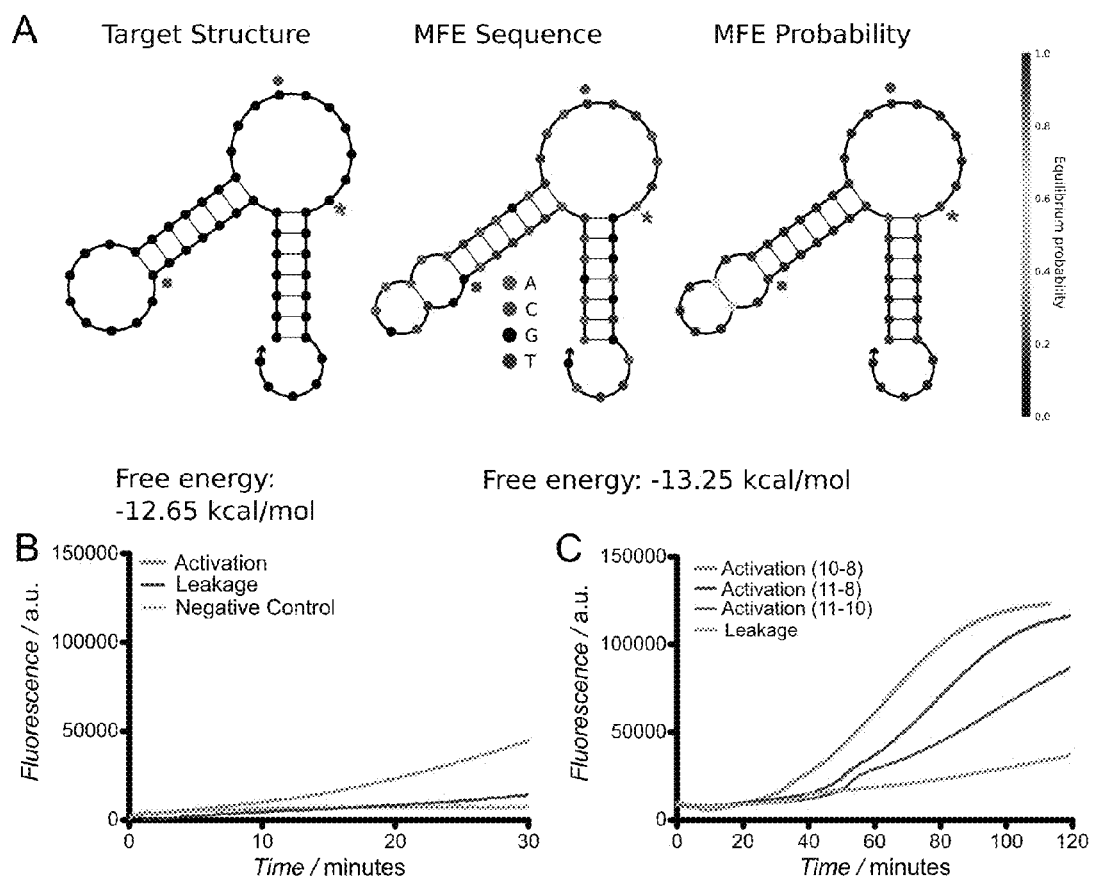
FIG. 18. SCS Design 8v1. (A) This SCS design was a dual stem loop design, an optimized version of the previous design. The main difference between this and Design 7 (FIG. 17) was the length of each stem, which also resulted in longer DNAzyme substrate binding arms. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 8v1, over 30 minutes using DNA only strands. (C) Two-layer cascade responses when the SCS is cleaved by various upstream DNAzymes with different length substrate binding arms. (C) Oligonucleotide sequences and concentrations for each variant of SCS Design 8 for DNAzyme cascades (Table 33-36).

Design 7 provided moderate improvement of leakage (FIG. 17B). Design 8 is a further derivative of Design 7, designed to increase kinetics of the activation mechanism illustrated in FIG. 10. One iteration, Design 8v1 (FIG. 18A), was tested as in its DNA form as well as its RNA form (FIG. 18B). Although the rate of activation was somewhat slow after 30 minutes, it retained good signal-to-background over 120 minutes when cleaved by various upstream DNAzymes with different length substrate binding arms (FIG. 18C).

Figure 19:
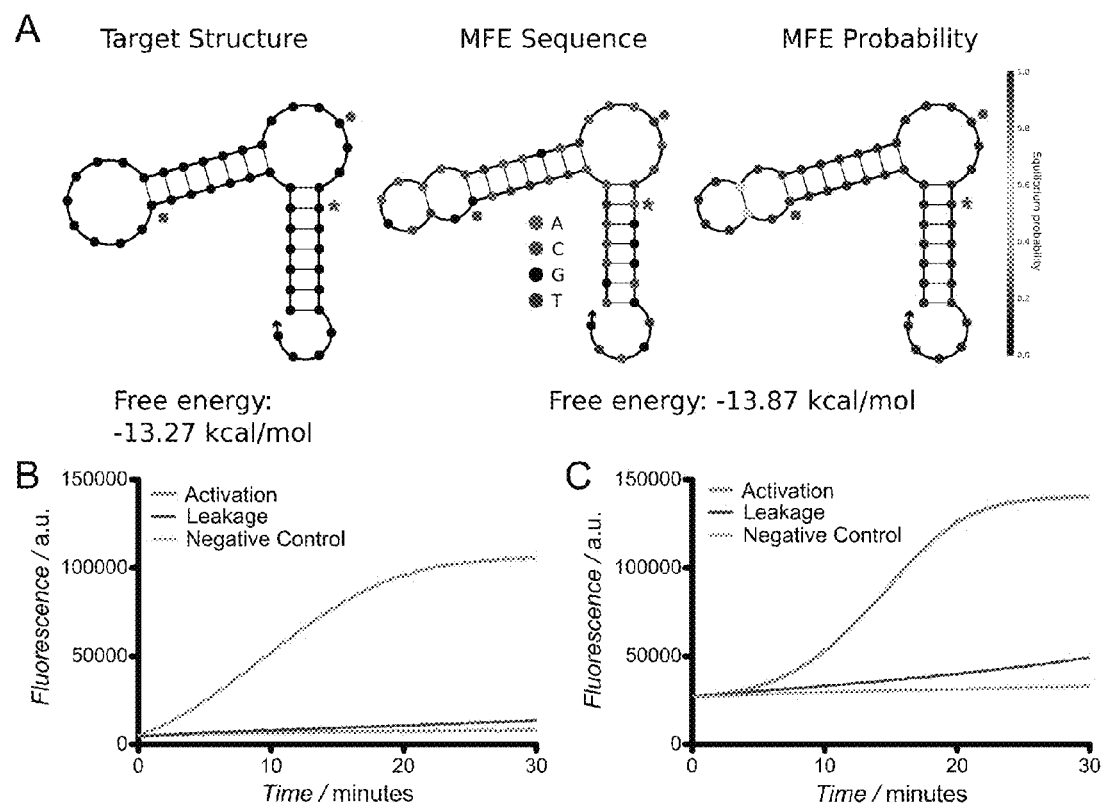
FIG. 19. SCS Design 8. (A) This SCS design was a dual stem loop design, an optimized version of the previous design, and the final design and sequence of the two layer DNAzyme cascade. The main difference between this and Design 8v1 (FIG. 18) was the length of each stem, which was optimized by moving the RNA cleavage site into the outer stem. The target structure (left) was implemented with the given sequence (center) producing the MFE structure (right). The circle denotes the beginning of the activator toehold; the end of the activator sequence is denoted by the square. The star marks the cleavage site. (B) Response of the SCS design in (A), Design 8, over 30 minutes using DNA only strands. This design showed a marked improvement in activation rate while retaining a low rate of leakage. (C) Implementation of the DNA analysis using the RNA form and upstream DNAzyme to active the SCS. Although the shape of the curves are slightly different, the lag time of the RNA form likely corresponding to the rate of UE binding and cleavage, while the DNA form provides activator directly to the system. The similarity between the two graphs demonstrates the cost-effectiveness of this approach; approximation of RNA cleavage by a "pre-cleaved" DNA form provides a reliable qualitative assessment of the performance of the circuit.

Design 8 is illustrated in FIG. 19A, and has several modifications from the other variants. For example, Design 8 possesses the placement of the cleavage site into the outer stem similar to Design 6. This had several effects. First, the position of the cleavage site fixed the DNAzyme binding arms at 8 bp each, which promotes rapid product dissociation, as previously discussed. Second, this enabled the size of the outer loop to be minimized, ensuring a high structural stability to reduce leakage. Third, this also enabled the use of the longer 7 bp stems, which stabilize the structure to ensure low leakage. Lastly, the hybridization of the cleavage site in the outer stem also served to protect the RNA base from degradation, which may have also been a contributing factor to gate leakage. Using a DNA form of a pre- and post-cleaved SCS molecules offered a good approximation of the performance of the RNA form and upstream DNAzyme cleavage, as seen in FIG. 19B and FIG. 19C. Although the shapes of the curves are slightly different, the lag time of the RNA form may correspond to the rate of UE binding and cleavage, while the DNA form provides activator directly to the system. The similarity between the two graphs demonstrates the cost-effectiveness of this approach; approximation of RNA cleavage by a "pre-cleaved" DNA form provides a reliable qualitative assessment of the performance of the circuit. Thus, the design of an SCS structure to facilitate DNAzyme communication through a two layer cascade was achieved, producing a robust activation response in the presence of an upstream DNAzyme and minimal gate activation (leakage) in the absence.

This design also benefitted from a 3 bp extension of the inhibitor further into the core while retaining the length of the sequestered activator. This extension acts as a clamp, which had been shown to reduce gate leakage by preventing blunt end stacking of the activator and inhibitor in the core region. By not fully displacing the inhibitor, we achieved a much improved circuit response.

The design process of the SCS structure for DNAzyme-based signaling cascades therefore balanced the complex kinetic rates that constitute the activation and leakage processes. Due to the minimal gate structure and toehold availability of the DNAzyme displacement gates, the desired kinetic rates were optimized through the thermodynamic favorability between the pre- and post-cleavage secondary structure of the SCS molecule. This approach is in contrast to the SCS design for the modular gate cascades, in which the structure is built into the gate itself, which relieved many of the design constraints on the SCS.

The design process revealed that many potential design variants are available. The range of response profiles exhibited by each design demonstrates that there is a highly diverse structure-space that even short sequences can adopt, resulting in a wide variety of behaviors. While the exemplary design described above was performed with a desired target of activities, designs that were deemed incompletely adequate for the exemplified design parameters may be perfectly suitable for other applications. Furthermore, despite several designs having large structural differences, their performance was quite comparable, indicating that desired thermodynamic interactions can be achieved through many different pathways. This also emphasized the necessity of granularity in the design process—small alterations often resulted in large changes to the structural stability and therefore the kinetic rates of subsequent reactions. Here again, however, the various stabilities and/or kinetic rates may be perfectly suitable for certain applications. Finally, developing a five layer cascade demonstrated the success of the rational design approach for the dynamic modification of DNA nanostructures. By focusing on the structure itself to execute the thermodynamic pathways, one can successively iterate the design to rapidly scale up the size and complexity of DNAzyme cascading interactions.

The success of the rational design for SCS structure, both with the DNAzyme displacement gates and the modular gates, provides a platform for designing logic-based DNAzyme signaling cascades. For example, DNAzyme cascades may serve as a platform for constructing synthetic enzymatic cascades and/or more complex computational architectures. Thus, catalytic molecular logic devices can now implement serial interaction of logic gates rather than solely parallel arrays in a reliable, predictable, and reproducible manner. This enables the integration of many input signatures into a single DNA circuit, which can provide advantages over, for example, existing biomedical diagnostic devices.

Modular DNAzyme Gates for Biosensing Applications

In another aspect, this disclosure describes a modular nucleic acid-based sensor gate capable of multiplexed, amplified detection of arbitrary target nucleic acid sequences. The nucleic acid strands involved may include DNA, RNA, nucleic acid analogs such as PNA or LNA, or any combination of these. The sensor gate includes two strands: an enzyme strand and an inhibitor strand. The system additionally includes: a fuel strand and a substrate strand. If the sensor gates, fuel strands, and substrate strands are all present in solution, the addition of a particular detection sequence produces an amplified output. This can be used to detect target sequences with concentrations in the picomolar range in an isothermal assay.

In some embodiments, the enzyme strand includes a catalytically active nucleic acid enzyme (for example a DNAzyme or ribozyme) that cleaves a substrate molecule, together with an adjoining input detection domain. The inhibitor strand contains domains that are complementary to the input detection domain and at least part of the nucleic acid enzyme sequence from the enzyme strand. In addition, the inhibitor strand has an overhanging primary toehold adjacent to the complementary input detection domain, and between the two domains complementary to parts of the enzyme strand there is a secondary toehold domain sequestered in a small bulge, typically 5-8 nucleotides in size, although other lengths may also be used. The bulge can impose a topological constraint, restricting access to the secondary toehold while the input detection domains on the enzyme strand and the inhibitor strand are still bound together. The input detection domain and the overhanging single-stranded toehold domain are chosen to be complementary to a target nucleic acid sequence of interest. The enzyme-inhibitor strands are bound together to produce an enzyme-inhibitor complex. The enzyme-inhibitor complex inhibits the catalytic activity of the enzyme strand while it is bound to the inhibitor strand.

According to some embodiments, the fuel strand is partly complementary to the looped toehold on the inhibitor strand (for example, one or more bases may be mismatched in this part of the fuel strand, in order to reduce unwanted activation) and is partly complementary to the domain from the inhibitor strand which is complementary to part of the nucleic acid enzyme sequence (for example, one or more bases may be mismatched in this part of the fuel strand, typically at the initiation point for the branch migration reaction, again to reduce unwanted activation).

According to some embodiments, the substrate strand contains two domains which are complementary to the substrate recognition domains of the nucleic acid enzyme, with an appropriate cleavage site sequence in between. The substrate strand may be any appropriate single-stranded oligonucleotide, for example, but not limited to, RNA, DNA, nucleic acid analogs such as PNA or LNA, or any combination of these. The substrate strand may be functionalized so that the cleavage reaction may be observed, for example using one or more fluorescent labels or a radioisotope.

According to some embodiments, the detection reaction begins with the target nucleic acid molecule binding to the complementary primary toehold on the inhibitor strand. This initiates a strand displacement reaction which causes the input detection domain of the enzyme strand to be displaced from the enzyme-inhibitor complex. This reaction releases the secondary toehold domain on the inhibitor strand from the looped configuration in the bulge, which makes it possible for the fuel strand to easily bind to the secondary toehold. Once the fuel strand is bound to the unlooped secondary toehold, it can initiate a strand displacement reaction that displaces the remainder of the enzyme strand from the enzyme-inhibitor complex. The enzyme strand can then fold into a catalytically active conformation and proceed to cleave substrate strands at the cleavage site. A single nucleic acid enzyme may cleave multiple substrate strands in a multiple-turnover reaction, enabling isothermal signal amplification. If the substrate has been functionalized, the output from the system can be observed by monitoring these cleavage reactions, for example using loss of FRET or by gel electrophoresis.

According to some embodiments, the sequences of the input detection domains and the nucleic acid enzyme sequence are unrelated, which allows one of these sequences to be modified independently of each other. For example, this feature may be used to produce a collection of sensor gates which detect different target sequences but all cleave the same substrate strands, so that the system produces an output signal if any of the target sequences are present, thereby implementing a logical OR function. As another example, a collection of sensor gates which detect different target sequences and cleave different substrate strands, could be used to provide multiplexed readout of all of the target sequences in a single assay, if all of the substrate strands are functionalized such that the cleavage of all of the different kinds of substrate strand may be monitored simultaneously, for example using different colored fluorophores or using flow cytometry to detect loss of fluorescence from populations of microparticles stained with different fluorescent dyes.

It will be appreciated that the disclosed techniques and assays are directly applicable to multiplexed, isothermal detection of low concentrations of arbitrary nucleic acid sequences, for example in pathogen detection assays, such as the multiplexed isothermal detection of multiple strains of Shiga toxin-bearing *E. coli*.

DNA-based sensors and logic circuits show great promise for implementing bioassays for direct detection of pathogenic DNA and RNA. Computational devices made of DNA are inherently biocompatible, and the predictable nature of Watson-Crick complementarity allows the design of probes that can detect particular target sequences by direct hybridization, with high specificity. Furthermore, the low and decreasing cost of DNA synthesis makes it an attractive candidate for the development of low-cost bioassays.

Application of Modular DNAzyme Displacement Gates for Bacterial Signature Detection According to various embodiments, the present disclosure describes the development of a modular library of DNA-based sensor gates for biosensing applications. Specific embodiments are disclosed below. One such embodiment enables allosteric control via rationally designed modularization, resulting in gates that are directly applicable to bioassay development. Our gate design separates target detection and signal reporting into orthogonal modules, which allows the detection module to be modified while keeping the reporter module fixed. This enables multiplexed, sequence-specific detection of many target strands with a single fluorescent readout. The detection module uses toehold-mediated strand displacement reactions for sequence-specific detection and the reporter module uses DNAzyme-catalyzed cleavage of fluorogenic substrates to produce an amplified fluorescent output in isothermal conditions. We demonstrate this by developing a multiplexed assay to detect target sequences from the genomes of a number of Shiga Toxin-producing *Escherichia coli* (STEC) strains.

Figure 20:
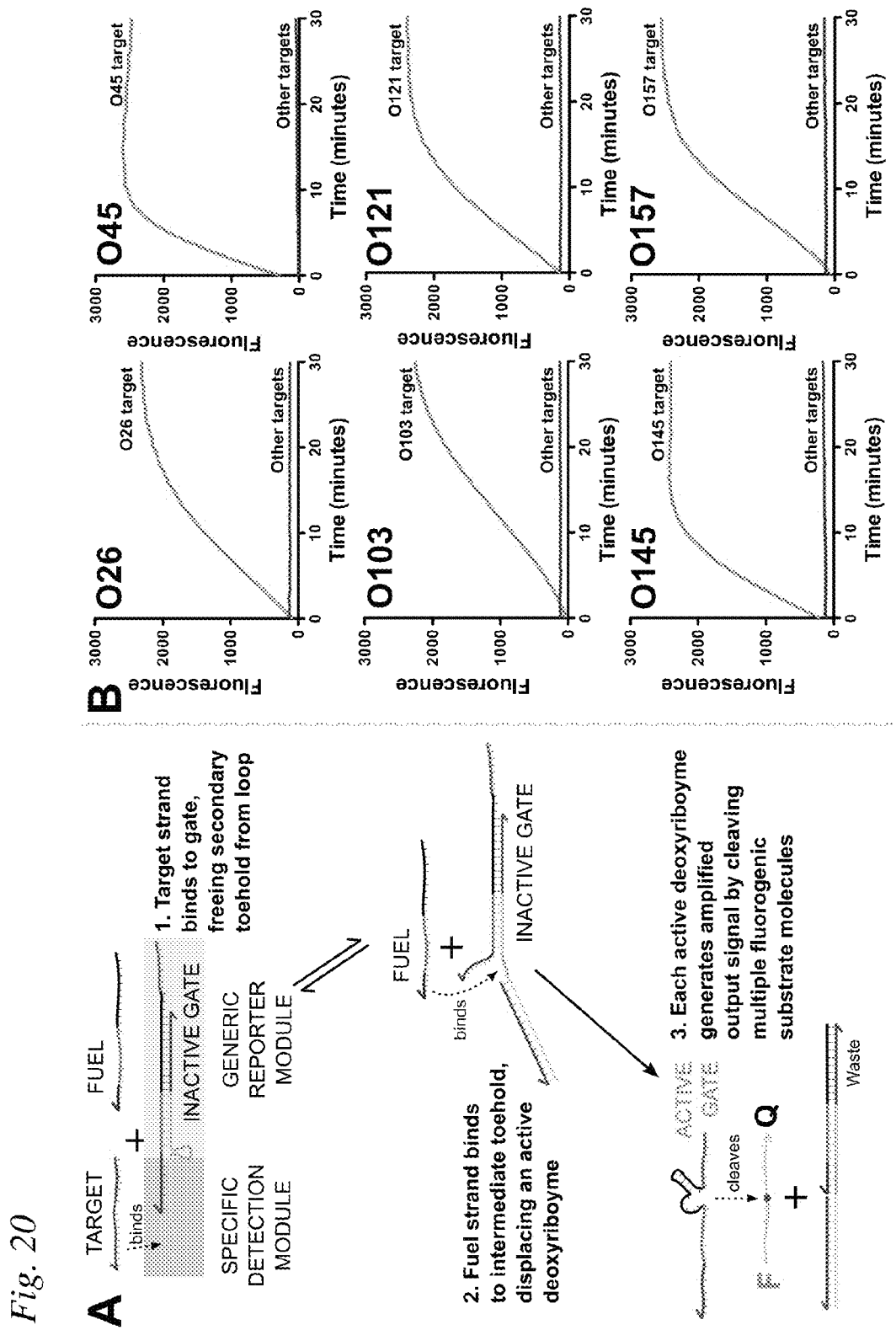
FIG. 20. Modular DNAzyme sensors and their application to detection of STEC target sequences. (A) Basic mechanism of detection and DNAzyme activation by modular DNAzyme displacement reactions. Initially, the DNAzyme is inhibited by partial hybridization to a complementary inhibitor strand. The detector gate consists of a target-specific detection module (green toehold and duplex) and a generic reporter module (secondary looped toehold and inhibited DNAzyme gate). The target strand binds to the detection module via a toehold-mediated strand displacement reaction, which partially displaces the DNAzyme strand from the complex. This reaction removes the topological constraint on the secondary toehold by freeing it from the loop, which in turn enables the fuel strand to bind to the detector gate. This initiates another strand displacement reaction, which fully displaces the active DNAzyme from the inhibitor. The free DNAzyme can then fold into a catalytically active conformation and generate a fluorescent output by cleaving substrate molecules labeled with a FRET pair. If substrate is present in excess relative to active DNAzyme, each DNAzyme may catalyze the cleavage of many substrate molecules in a multiple-turnover regime. This fact enables isothermal signal amplification. The fuel strands are provided along with the gate complexes in solution, and it is vital that the fuel strand cannot easily bind to the secondary toehold while the secondary toehold is sequestered in the bulge (see Supporting Information for discussion of this point). Therefore, activation of the DNAzyme is dependent on the presence of the correct target strand in solution. (B) Detection of target sequences taken from the genomes of various STEC serotypes. Detection gates for six STEC serotypes (O26, O45, O103, O121, O145 and O157) were constructed by fixing a sequence for the reporter module and varying the target-specific detection module, following the scheme outlined in (A). Each gate was characterized separately, with initial concentrations of 100 nM DNAzyme-inhibitor complex, 25 nM additional inhibitor free in solution, 500 nM fuel and 250 nM substrate. For each gate, the positive response was obtained by adding 50 nM of the correct target sequence. The negative controls plotted above are the response obtained by a particular gate in the presence of 50 nM of each of the other five target sequences. This demonstrates that the response of the individual detector gates is highly sequence-specific. In the graphs presented here, the baseline response that occurs when the fuel is present in solution without the target strands was subtracted out from each trace.

Each sensor gate includes two domains: a target-specific detection module (DM) and a generic reporter module (RM), which contains the inhibited DNAzyme (FIG. 20A). The detection module uses a traditional toehold-mediated strand displacement mechanism to partially displace the DNAzyme from the catalytically inactive enzyme-inhibitor complex, and the reporter module is functionally equivalent to our previously demonstrated DNAzyme displacement logic gates. When the correct target sequence is present, it binds to the detection module toehold and branch migration occurs up to the beginning of the reporter module. The toehold necessary to disinhibit the reporter module is sequestered in a 5 nucleotide bulge between the two modules, and the binding of the target strand frees this toehold from the topological constraint imposed by the bulge, allowing it to become single-stranded. The fuel strand is then able to bind the free toehold in the reporter module and displace the remainder of the DNAzyme strand. The free, catalytically active DNAzyme is then able to bind and cleave its substrate, producing a fluorescent readout. For these experiments we used the 8-17 DNAzyme, because of its small size and high catalytic efficiency.

We demonstrated the practical applicability of our modular sensor gates by designing a collection of sensors based on the same output module, each of which recognizes a target sequence specific to one of the following STEC serotypes: O26, O45, O103, O121, O145 and O157. These target sequences are based on PCR primers previously used for STEC detection (Paddock et al., 2012, *Vet. Microbiol.* 156: 381-388). These sequences are suitable for our purposes because PCR primer sequences are typically chosen to minimize secondary structure, which is also beneficial for TMSD reactions. In our experiments, inputs were single-stranded synthetic DNA oligonucleotides with the same sequences as the target sequences of interest. Since the input and output modules of our gates do not overlap, we can modify the sequence in the input detection module while keeping the output module fixed. This will allow us to multiplex detection of the different STEC target sequences in a parallel gate array with a single fluorescent readout via a common fluorogenic substrate molecule.

We initially characterized each of the STEC serotype-specific gates individually, as shown in FIG. 20B. For each experiment, the detection gate was prepared by annealing 100 nM of the DNAzyme strand with 125 nM of the corresponding inhibitor, producing 100 nM of the enzyme-inhibitor gate complex and 25 nM free inhibitor in solution. Each experiment also used 500 nM of the fuel strand and 250 nM of the fluorogenic substrate. For the positive traces shown in FIG. 20B, 50 nM of the target sequence of the particular serotype gate in question was added, and for the negative traces, 50 nM of all five serotype target sequences except for the correct target was added. In each gate, we observed a significant response in the presence of the correct serotype target sequence, and a very low background in the absence of the other serotypes. This demonstrates that the gates are highly sequence-specific. Variations in the activation rates between the detection gates for different STEC serotypes may be attributed to differences in the stability of the enzyme-inhibitor complex caused by the different target sequences in the detection modules, or by different levels of secondary structure in the target strands, which would impede the binding of the target to the toehold of the detection module.

Additional controls showed that the enzyme-inhibitor complex is highly stable in the absence of the fuel strand, even in the presence of the target sequence. The presence of the fuel strand contributes to a small increase in background signal that varies in a concentration dependent manner. This is to be expected, as imperfections in the enzyme/inhibitor complex and breathing of the duplexes near to the secondary toehold bulge may allow strand invasion via the secondary toehold in the absence of the target sequence, allowing the fuel strand to activate the DNAzyme even though the target sequence inhibition remains intact. We use fuel strands with one or more rationally introduced mismatched bases in the toehold domain, which considerably reduces the rate of spurious activation due to the fuel strand binding to the toehold in the bulge. However, this leak rate is insignificant compared to the dramatic increase in reaction rate when the target strand is added to the solution and the complete reaction mechanism outlined in FIG. 20A can occur. Specific assay conditions may demand either a faster response time or a high fidelity signal, and fuel concentrations can easily be tailored to meet these criteria.

Figure 21:
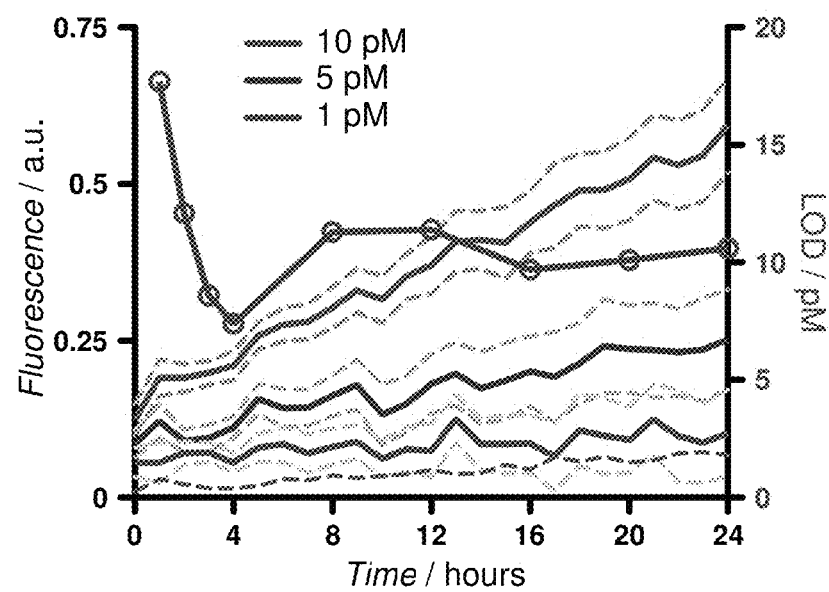
FIG. 21. Investigating the limit of detection of the O45 sensor gate. Colored line traces (left axis) show the response of the O45 detection circuit with various input concentrations: 10 pM, 5 pM and 1 pM. For these experiments the system was diluted to 100 pM gate concentration with 10 pM excess inhibitor, 100 pM fuel and 250 nM substrate. The background signal in the absence of input has been subtracted from all traces. Solid lines are average fluorescence values from 5 replicates, and dashed lines are one standard error above and below the mean in each case. Red data points (right axis) are detection limits at 3σ above the standard error of the background at various time points, calculated using the standard IUPAC definition.

We lowered the concentration of target strands in solution to investigate the limit of detection for our gates. FIG. 21 shows the detection of target sequences in the low picomolar range. In order to suppress leakage, the gate concentrations were reduced to 1 nM, which had the side effect of extending the timescale of the reactions, while remaining well within a reasonable timeframe for assay development. Using the fluorescence over background, statistical analysis gave a detection limit of <8 pM at three standard deviations over background after 4 hours. Thus our sensor gates are more sensitive than existing approaches based on antibody detection.

Excess inhibitor helps to inhibit the DNAzymes more efficiently. However, the excess inhibitor concentrations hinder achieving even lower limits of detection by a two-fold effect. First, free inhibitor can bind the target strands, preventing it from binding productively to gate complexes. Second, free inhibitor may be able to rebind activated DNAzyme strands and deactivate them. However, while lower detection limits can likely be achieved using increased purification methods such as PAGE purification of gate complexes, this may be less desirable in the development of bioassays, where cost and ease of use are important factors.

Figure 23:
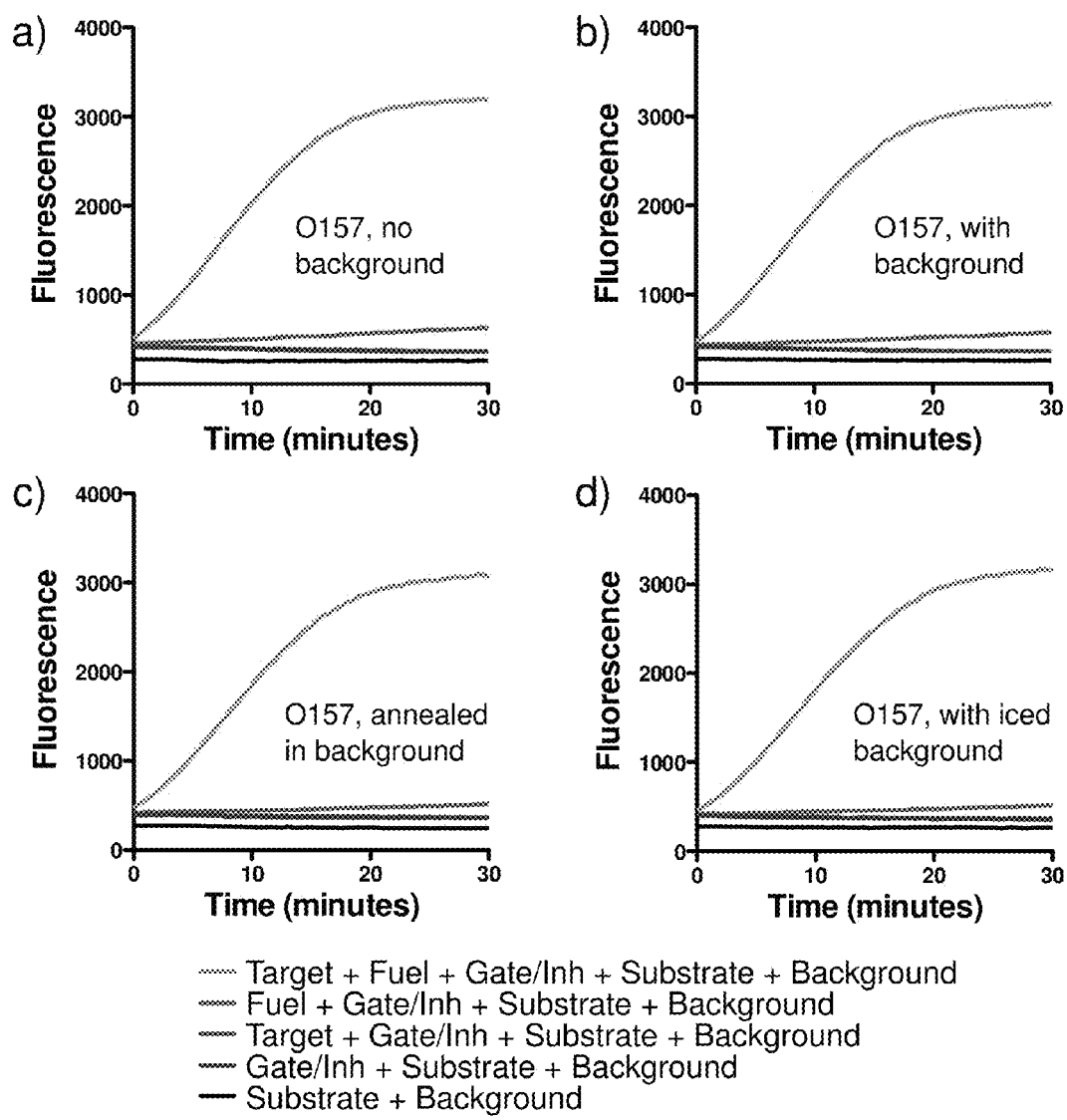
FIG. 23. Performance of O157 sensor gate in a random DNA background. A) Control experiment with no background. B) Characterization in presence of background DNA. C) Here the deoxyribozyme-inhibitor complexes were annealed in the presence of herring sperm DNA, allowing the possibility of gate misfolding due to interactions with the background. D) Here the deoxyribozyme-inhibitor gate complexes and the background DNA were heated separately, and the background was quenched on ice before adding to the solution, to prevent rebinding of the background DNA. All experiments used 100 nM O157 gate, 25 nM excess inhibitor, 50 nM target strand, 500 nM fuel with 1 mismatch, 250 nM substrate. Experiments in background also contained 1 µM herring sperm DNA (Promega, Madison, Wis.).

Since all of our STEC detection gates use the same reporter module, they are all able to cleave the same fluorogenic substrate molecule. Therefore, if multiple STEC gates are present in solution simultaneously, as shown in FIG. 22A, a fluorescent signal is observed if any of the target sequences are present, giving a multiplexed detection circuit that implements OR logic. We demonstrated the multiplexed detection capabilities of our modular DNAzyme displacement gates by performing a six-way assay for the detection of any of the aforementioned six STEC serotype target sequences. The multiplexed detection circuit consisted of 100 nM of each annealed enzyme-inhibitor gate complex, 25 nM excess inhibitor and 500 nM of the common fuel strand. This system was replicated in seven wells, and to each well we added one of the STEC target sequences at 50 nM, with one well containing no target sequences as the control. The wells were incubated for 15 minutes, after which 250 nM of the common fluorogenic substrate strand was added to each well. The endpoint fluorescence values shown in FIG. 22B were measured after a further 30 minutes. We observed a high signal to noise ratio in all cases, with the relative heights of the bars for the positive traces corresponding roughly to the activation rates observed in the individual characterizations (FIG. 20B). The background was slightly higher in this experiment, most likely due to the higher overall concentration of detector gates causing an increase in the leak rate. Furthermore, we demonstrated that the O157 modular DNAzyme gate functions correctly in the presence of a random DNA background in the form of herring sperm DNA, as shown in FIG. 23. These data demonstrate that our system can simultaneously detect the STEC-specific sequences of interest in a mock bioassay scenario and is resistant to background interference.

In summary, our disclosure enables detection of multiple arbitrary target sequences by separation of the target and reporter modules. Using unpurified strands and gate complexes, we calculated a limit of detection of ~8 pM after 4 hours. Multi-strain detection capability was demonstrated via an assay detection using sequences analogous to six different STEC strains, and the gates were shown to be resistant to a random DNA background. These gates should serve as a basis for the continued development and application of multiplexable, isothermal nucleic acid detection assays.

Thanks to our modular design, it should be equally straightforward to modify the reporter module while just as easily, producing a different readout channel for each detected strain. If substrates are conjugated to fluorescently dyed beads, we anticipate that flow cytometry will allow a large number of different strains to be detected in a single assay. Our previous research on development of miniaturized flow cytometers shows promise for taking this more sophisticated assay into the field.

Additional Biosensing Applications of Modular DNAzyme Displacement Gates

Modular DNAzyme sensor gates enable multiplexed detection of multiple pathogen strains at low concentrations. The illustrated exemplary modular sensor gate includes a target detection module where target strands bind to the gate, and an orthogonal reporter module that, when activated, cleaves a complementary substrate to generate an amplified output signal. In this illustrative example, an additional fuel strand activates the reporter module following binding of a target strand to the detection module.

Figure 24:
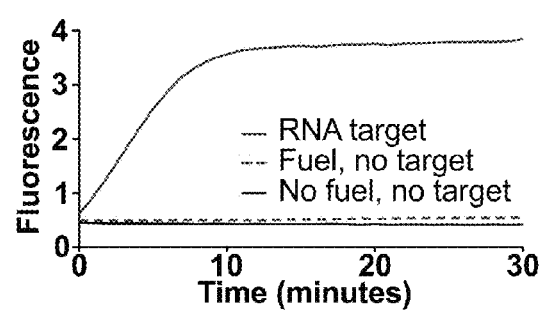
FIG. 24. Experimental results demonstrating detection of an RNA oligomer by a modular DNAzyme biosensor gate. A strong fluorescent response was observed in the presence of the RNA target strand, with no increase in fluorescence observed in the absence of the RNA target. This demonstrates that our modular DNAzyme gates can be used to detect short RNA strands such as microRNAs. This is an important capability for practical diagnostic applications.

Modular sensor gates can be easily redesigned to detect different targets, and a number of sensor gates can be deployed in parallel to simultaneously detect a range of different targets in a multiplexed assay. FIG. 24 provides data demonstrating the ability to detect single-stranded RNA oligomers. FIG. 25A provides a schematic example of a protocol for detecting denatured plasmid DNA using modular DNAzyme gates, which could be generalized to other dsDNA detection targets of interest, such as genomic DNA. FIG. 25B provides data demonstrating the ability to detect plasmid DNA that has been denatured, either thermally or chemically. FIG. 21 shows data demonstrating a limit of detection below 10 pM when detecting DNA oligomers in a randomized DNA background. This is relevant because modular DNAzyme sensors allow a generic sensor framework for virus detection.

Figure 26:
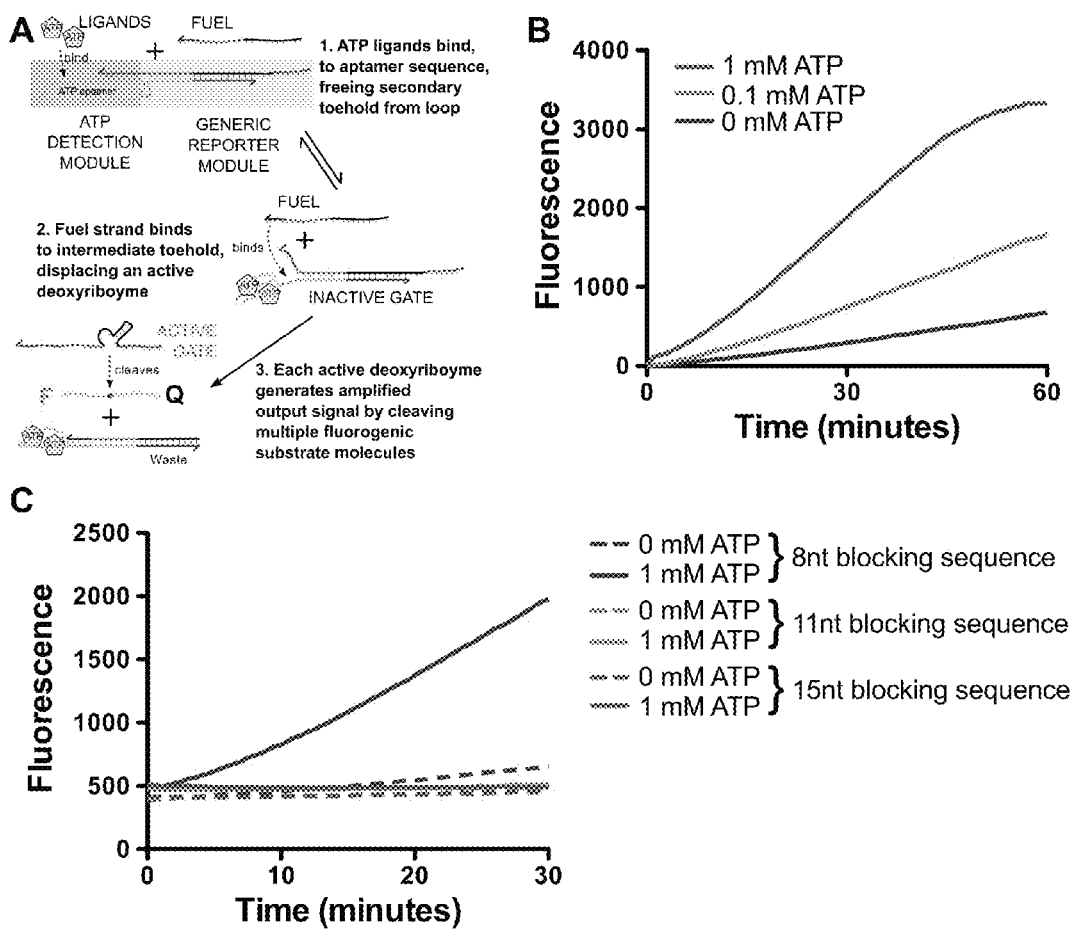
FIG. 26. Aptamer sensing using modular deoxyribozyme gates. A) Replacement of the target detection module with a partially blocked aptamer sequence allows the gate to be triggered by the binding of small molecules, in this case ATP. B) Kinetic traces showing gate response to various ATP concentrations. C) Effects of length of blocking sequence for ATP aptamer. Sensor gates with 11 and 15 nt blocking sequences show no activation with 1 mM ATP, where the sensor gate with an 8 nt blocking sequence shows a positive response with 1 mM ATP. Concentrations were 100 nM aptazyme gate, 25 nM excess inhibitor, 250 nM fuel, 250 nM substrate.

This assay technology may be applied to a range of biodetection targets, including, but not limited to, nucleic acids and small molecules. FIG. 26 demonstrates that modular DNAzyme sensor gates can be used to detect small molecule ligands by replacing the target detection module with a partially blocked aptamer sequence. FIG. 26A illustrates the reaction mechanism for the case of an ATP aptamer, in which binding of two ATP molecules to the aptamer causes a conformational shift, displacing the target detection module from the double-stranded conformation and opening up the secondary toehold that was previously sequestered in the loop. Subsequent binding of the fuel strand can complete displacement of a catalytically active DNAzyme to produce an amplified output. FIG. 26B demonstrates successful demonstration of sub-millimolar concentrations of ATP using this method. FIG. 26C shows that the availability of the DNAzyme gate for ATP binding is critically dependent on the length of the blocking sequence: if the blocking strand consists of 11 nt or more, the duplex in the target binding module is too stable for ATP to bind and disrupt the duplex. Blocking strands of 8nt were found to produce a satisfactory response to ATP binding.

Figure 27:
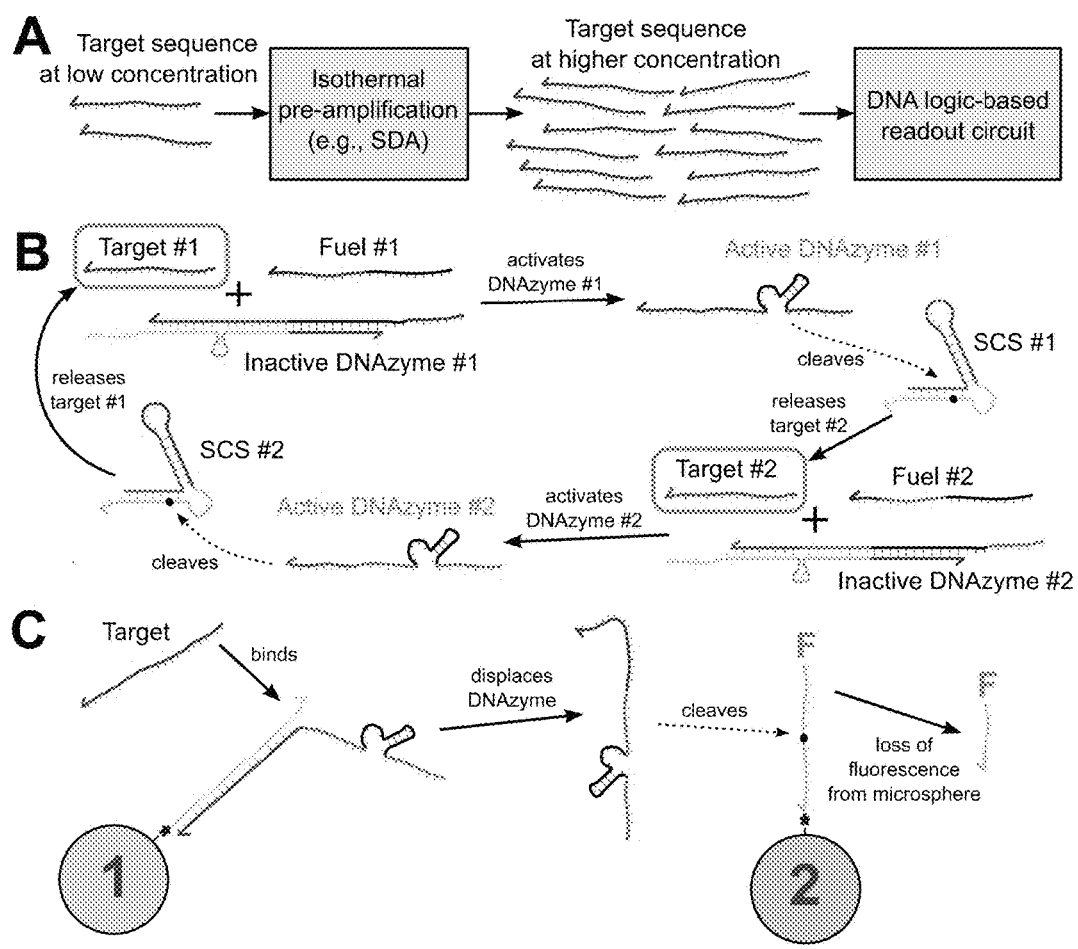
FIG. 27. DNAzyme cascade designs for increased sensitivity and robustness. (A) Schematic of detection framework with isothermal pre-amplification of targets coupled to a DNA logic-based readout circuit. (B) Cross-catalytic circuit with two detection targets (highlighted), which could be two signatures from different parts of a viral genome. (C) Schematic example of a simple DNAzyme cascade between distinct populations of microspheres. Cleavage in the absence of the target may be minimized by attachment geometry.

FIG. 27A is a schematic representation of how one might integrate our logic circuit designs with isothermal pre-amplification strategies to achieve the limits of detection that allow one to detect RNA concentrations in practical applications. For example, the viral load at the onset of febrile illness is typically around $10^6$-$10^8$ copies/mL, dropping to around $10^3$ copies/mL over the next few days. These values correspond to concentrations of approximately 1-100 fM and ~$10^{-3}$ fM, respectively. Thus, detecting RNA at, for example, 1 fM in a straightforward, single tube assay allows one to achieve diagnostically relevant detection limits in clinical samples.

One can use conventional sequence alignment software to isolate subsequences of viral genomes as potential detection targets. Having isolated detection targets, one can use, for example, nucleic acid structural prediction software (as described in, e.g., Dirks et al., 2007, *SIAM Rev.* 49(1):65-88; Zadeh et al., 2011, *J. Comput. Chem.* 32(1):170-173; Zadeh et al., 2011, *J. Comput. Chem.* 32(3):439-452) to design sensor gates to detect targets with these sequences. The sequence-specific approach provided by the logic circuits described above enable one to distinguish between serotypes—and to distinguish dengue from other flaviviruses such as WNV and SLEV. This is currently not possible with conventional serologic assays.

FIG. 27A presents a schematic for the assay protocols. One can use existing isothermal nucleic acid amplification technologies, such as rolling circle amplification (RCA, Fire et al. 1995, *PNAS* 92(10):4641-4645; Zhao et al., 2008, *Angew. Chem. Int. Ed. Engl.* 47(34):6330-6337), self-sustained sequence replication (3SR, Guatelli et al., 1990, *PNAS* 87(19):7797), or strand displacement amplification (SDA, Walker et al., 1992, *Nucl. Acids Res.* 20(7):1691-1696) to provide initial pre-amplification of target concentrations, which can then be fed into a DNA logic-based readout circuits. RCA can be used to amplify RNA targets to produce a corresponding DNA output using the Phi29 polymerase, for example using ligated RNA padlock probes as splint oligonucleotides, or using RNA detection to initiate amplification via three-way junction formation. 3SR generates both RNA and cDNA copies of an RNA template in an isothermal process that mimics certain aspects of retroviral replication. Both of these pre-amplification strategies can isothermally directly generate suitable DNA or RNA inputs for the logic-based readout circuits given an RNA detection target. SDA, on the other hand, involves an initial reverse transcription step to translate the RNA target into a DNA primer to initiate amplification.

These systems can be used to pre-amplify RNA target concentrations to produce either DNA or RNA oligomers to feed into multi-target DNA logic circuits. To reduce the amount of pre-amplification that is required to generate a detectable signal in the readout circuit, the DNAzyme logic circuits may be designed with reduced limits of detection. This may be accomplished in at least three ways.

First, one can extend the DNAzyme cascade designs to incorporate cross-catalytic feedback cycles, by combining a modular DNAzyme sensor gate (FIG. 20) with DNAzyme signaling cascades based on the SCS design (FIGS. 6 and 7). This can enable the logic circuits to generate additional target strands when activated, thereby providing further signal amplification. Cross-catalytic DNAzyme systems can achieve exponential signal growth by cleaving circularized DNAzymes to activate them. A logic-gated approach, illustrated in FIG. 27B, involves two target binding reactions that form a cross-catalytic cycle. This design can reduce unwanted signal generated by, for example, spurious DNAzyme activation. Decreasing unwanted signal generation lowers the achievable limit of detection.

Second, different circuit components may be physically isolated, for example by attaching them to different populations of micro- or nanoparticles, as shown in FIG. 27C. This design can reduce collisions between inactive circuit components to reduce unwanted DNAzyme activation. This also may allow one to simplify circuit designs because attachment geometry can prevent components from interacting with each other until they are released from their microspheres. This design may have particular utility in the context of using nanoparticles as an in vivo circuit delivery strategy.

Third, one can use enhanced purification techniques such as, for example, column-based purification of DNAzyme-inhibitor complexes, or purification based on binding of unwanted strands to biotinylated complementary capture strands immobilized on streptavidin-coated paramagnetic microspheres, which can be easily removed from solution by applying an external magnetic field, to reduce our limit of detection even further. Purification of components can reduce leakage in catalytic DNA circuits.

DNAzyme-catalyzed cleavage of substrate molecules labeled with a fluorescent donor molecule at one end and an acceptor at the other can be observed in real time by observing an increase in bulk fluorescence due to loss of FRET. To monitor multiple DNAzymes simultaneously, one can use different fluorophore-quencher pairs on each substrate. In the case of microsphere-based assays, one can observe loss of fluorescence from microspheres using flow cytometry.

DNAzymes (Dass et al., 2002, *Antisense Nucleic Acid Drug Dev.* 12(5):289-299; Kahan-Hanum et al., 2013, *Scientific Reports* 3:1535) and DNA nanomachines (Modi et al., 2013, *Nature Nanotechnol.* 8(6):459-467; Surana et al., 2011, *Nat. Commun.* 2:340) can function in living cells and in cell lysates. Thus, the components of the DNA logic circuits function in biological fluids and have potential applications in autonomous theranostic (diagnostic and therapeutic) nucleic acid logic devices.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1—Initial Characterization of DNAzyme Displacement Reactions

Oligonucleotide Sequences and Sequence Design

Conserved sequences for the catalytic core of the 8-17 DNAzyme were obtained from the literature. Sequences for the remaining domains were analyzed using the NUPACK web server and manually optimized to limit the formation of unwanted secondary structure. All oligonucleotides were purchased from Integrated DNA Technologies (Coralville, Iowa). DNAzymes, inhibitors, and input strands were ordered purified with standard desalting. DNA/RNA chimeric FRET reporter substrates were ordered purified using RNase-free HPLC. All sequences are listed in the Supporting Information (Section S1), along with their respective concentrations in each experiment. Oligonucleotides were resuspended in RNase-free $H_2O$ (Sigma-Aldrich) in accordance with the manufacturer-provided specifications at a stock concentration (50 µM). Working stocks were made by adding the resuspended oligonucleotide solution (50 µL) into buffer (950 µL). All reactions were run in a buffer of NaCl (1 m), HEPES (50 mm), and $ZnCl_2$ (1 mm), at pH 7.0. All oligonucleotide sequences are listed 5' to 3'. Functional domains have been color-coded to match the corresponding domains in the figures, domain junctions are indicated by a space, and strand names have been annotated with the corresponding labels from the figures. The dinucleotide junctions that are cleaved in the substrate strands have been highlighted using a yellow background, and mismatched bases in AND gate inhibitors are shown as single red letters. The RNA base at the cleavage site in each substrate strand is represented as rA, and the fluorophore (fluorescein) and quencher (TAMRA) are represented as FAM and TAM respectively.

FIGS. 3A-3D show logic gates implemented using DNAzyme displacement reactions. In FIG. 3A, the YES gate detects its input via the reaction mechanism shown in FIG. 2. In FIG. 3B, the NOT gate accepts an inhibitor strand as input, which deactivates a previously active DNAzyme. In FIG. 3C, the AND gate has a full-length inhibitor with toeholds ($t_3$ and $t_4$) on each end, and both input strands must be present to release the active DNAzyme via a cooperative strand displacement reaction. FIG. 3D shows Tables 1-3, wherein Table 1 provides the oligonucleotide sequences and concentrations for FIG. 3A, Table 2 provides oligonucleotide sequences and concentrations for FIG. 3B, and Table 3 provides oligonucleotide sequences and concentrations for FIG. 3C.

FIG. 4A-D show detection of arbitrary input sequences using mismatched inhibitors, FIG. 4A depicts a mechanism for an AND gate that detects two arbitrary input sequences. Since these inputs no longer displace the catalytic core, mismatched bases are added to the part of the inhibitor strand that binds to the core, to encourage unbinding of the DNAzyme strand in the presence of both inputs. FIG. 4B depicts kinetic traces for the AND gate design using mismatched inhibitors, for different numbers n=0,1,2,3 of mismatched bases in the $cc^*_{MM}$ domain. For clarity, we only plot the responses with both inputs present (solid lines) and with neither input present (broken lines with corresponding colors). FIG. 4C depicts complete characterization of the AND gate with 3 mismatched bases in the $cc^*_{MM}$ domain. We still see very strong inhibition of the AND gate in the presence of a single input, even when 3 mismatches are present in the inhibitor. FIG. 4D shows Table 4, which provides oligonucleotide sequences and concentrations for FIG. 4A.

FIGS. 5A-C are demonstration of a logic computation using DNAzyme displacement gates. FIG. 5A is a diagram of example logic circuit. FIG. 5B shows experimental validation of the corresponding DNAzyme displacement circuit. Responses below the broken line are interpreted as Out=0 and those above are interpreted as Out=1. The circuit responds correctly for each input combination, with a high signal-to-noise ratio. The fluorescence value in the fourth column is higher because both the AND gate and the NOT gate are active simultaneously in this case, resulting in both substrate populations being cleaved to produce a higher overall fluorescence level. FIG. 5C shows Table 5, which provides oligonucleotide sequences and concentrations for FIG. 5A.

Logic Gate Preparation

DNAzyme-inhibitor complexes were prepared by annealing the DNAzyme and inhibitor strands at 95° C. for three minutes on a heat block and cooled to room temperature over a minimum of 90 minutes to anneal.

Logic Gate Characterization Assays

Characterization of logic gate behavior was monitored as a time-based kinetic loss of FRET assay using a chimeric DNA substrate with an RNA base at the cleavage site. Dequenching of a 5' FAM group by the 3' TAMRA group indicated cleavage. Reagents were added in the order of logic gate, input, and subsequent addition of substrate to initiate the reaction. Characterization of individual logic gates (FIG. 3) was performed on a PTI (Birmingham, N.J.) Quantamaster-40 fluorimeter at an excitation wavelength of 492 nm and an emission wavelength of 518 nm. Characterization of the AND gate for detection of arbitrary sequences (FIG. 4), and the logic circuit demonstration (FIG. 5) were taken on a Spectramax M2e plate reader (Molecular Devices, Sunnyvale, Calif.).

Logic Circuit Demonstration

The circuit was set up in a manner similar to the logic gate characterization experiments. Gates were added first, followed by input, in the concentrations denoted in Table 5. To assess the final state of the circuit, inputs were allowed to react with gate complexes in the absence of reporter for 15 minutes. Upon addition of substrate, an endpoint fluorescent value was taken after 15 minutes. The t=0 fluorescence value for the case where $In_1=0$, $In_2=0$ and $IN_3=1$ was used as a baseline (since in this case we would expect minimal DNAzyme activity) and this value was subtracted from all of the endpoint fluorescence values.

Example 2—DNAzyme Signaling Reactions Using SCS Molecules

Materials

All oligonucleotides were purchased from Integrated DNA Technologies (Coralville, Iowa). Oligonucleotide sequences are listed in Tables 6-10. DNAzymes and inhibitors were purchased with standard desalting whenever possible, with the exception of oligonucleotides that exceeded 60 base pairs in length (which were PAGE purified by the manufacturer, in accordance with the manufacturer's recommended procedures). All DNA/RNA chimeric substrates (SCS molecules and fluorescent reporter substrates) were purified by RNase-free HPLC by the manufacturer. The fluorescent reporter substrates were labeled with a 5' FAM quenched by a 3' TAMRA fluorophore. Oligonucleotides were resuspended in RNase-free $H_2O$ (Sigma-Aldrich) in accordance with the manufacturer-provided specifications at a stock concentration of 50 µM. Working stocks were made by adding 50 µL of the resuspended oligonucleotide solution into 950 µL buffer.

Preparation of DNAzyme-Inhibitor Complexes and SCS Molecules

DNAzyme strands and inhibitor strands were pre-complexed by heating the DNAzyme and inhibitor strands together at 95° C. for three minutes on a heat block, and subsequently annealing by cooling to room temperature over a minimum of 90 minutes. In many cases, an excess of inhibitor relative to DNAzyme was used, to ensure complete inhibition of the DNAzymes—in these cases, the resulting solution of DNAzyme-inhibitor complexes and excess free inhibitor strands was used without further purification. Single-stranded SCS molecules (and loop-inhibited DNAzymes) were prepared using the same heating and annealing protocol.

Assay Conditions and Instrumentation

All assays were performed at room temperature (23° C.) in a buffer of 1M NaCl, 50 mM HEPES, 1 mM $ZnCl_2$, pH 7.0. Fluorescence was read either on a Quantamaster 40 fluorimeter (PTI, Binghamton, N.J.) in a 300 µL reaction volume or Spectramax M2e fluorescent plate reader (Molecular Devices, Sunnyvale, Calif.) in a 200 µL reaction volume. In all cases, fluorescein emission was monitored at 492 nm excitation and 518 nm emission wavelengths. Error bars indicate two standard deviations from the mean of three replicates, representing the 95% confidence interval.

DNA Sequence Design

The high-level structures of the strands and complexes were designed based on biophysical expectations of the stability of the complexes and their dynamic interactions with the other components of the system. The conserved sequences of the catalytic cores of the 8-17 and E6 DNAzymes were obtained from the literature (Breaker, R. R. and G. F. Joyce, 1995, *Chem Biol*, 2(10), 655-60; Santoro, S. W. and G. F. Joyce, 1997, *Proc Natl Acad Sci USA*, 94(9), 4262-6). Sequence design for SCS molecules was performed using a custom Python script that uses the NUPACK secondary structure prediction algorithm and the ISO numeric representation of nucleic acid secondary structure to find suitable domain assignments for the SCS sequence. Randomly generated sequences were tested using NUPACK to assess their equilibrium binding to the downstream DNAzyme and inhibitor strands in both the pre-cleavage state (to estimate leak rates) and the post-cleavage state (to estimate activation rates). Sequences that passed these tests were assessed for unwanted secondary structure using NUPACK and ISO (Dirks, R. M., et al., 2007, *SIAM Rev*, 49(1), 65-88; Fanning, M. L., J. Macdonald, and D. Stefanovic, 2011, *ACM-BCB*, ACM), and candidate sequences were manually checked and optimized. Sequences for loop-inhibited DNAzyme logic gates were derived from the sequences of the DNAzyme displacement logic gates in the two-layer cascade via ensemble defect optimization using the NUPACK design tool (Zadeh, J. N., B. R. Wolfe, and N. A. Pierce, 2011, *J Comput Chem*, 32(3), 439-52). For the dengue serotyping bioassays, we first performed a ClustalW sequence alignment on the genomes of all four dengue serotypes. Conserved and unconserved regions were identified manually and candidate target sequences were selected from these regions. These were then tested for secondary structure using NUPACK and optimized by hand as necessary. It is worth noting that NUPACK only models systems at thermodynamic equilibrium, and because the SCS participates in highly dynamic, transient interactions we can only draw limited conclusions about the behavior of our circuits from NUPACK predictions. We were forced to approximate the ribose base at the cleavage site by a deoxyribose base, because the available thermodynamic tables (SantaLucia, J., Jr., 1998, *Proc Natl Acad Sci USA*, 95(4), 1460-5) that serve as the basis of the NUPACK structure prediction algorithm do not include parameters for DNA-RNA hybrids. Furthermore, the thermodynamic tables are only strictly valid within a certain range of salt concentrations. In particular, our reactions require $Zn^{2+}$ ions in the buffer to serve as cofactors for the DNAzyme cleavage reaction, and the effects of these ions on DNA folding and on the relative stability of the various DNA structures are subjects of ongoing research (Kim, H.-K., et al., 2007, *Nat Chem Biol*, 3(12), 763-768; Mazumdar, D., et al., 2009, *J Am Chem Soc*, 131(15), 5506-5515; Kim, H. K., et al., 2008, *Chem Eur J*, 14(28), 8696-8703; Okumoto, Y. and N. Sugimoto, 2000, *J Inorg Biochem*, 82(1-4), 189-95; Faulhammer, D. and M. Famulok, 1997, *J Mol Biol*, 269(2), 188-202).

Oligonucleotide Sequences

Oligonucleotide sequences are presented in Tables 6-10 (FIGS. 28-32). All sequences are listed 5' to 3'. Substrates are cleaved at the dinucleotide junction between the two bases highlighted in red, and the catalytic cores of DNAzymes are highlighted in boldface. The RNA base at the cleavage site in each substrate (including SCS) strand is represented as rA. Fluorescein fluorophores and TAMRA quenchers are represented as /FAM/ and /TAM/ respectively.

Protocol for Multi-Layer Cascade Experiments (FIGS. 6B and 6C)

Sequences are listed in Table 6 (FIG. 28). Concentrations for FIG. 6B: 100 nM DNAzyme per layer, 125 nM inhibitor per layer (except the top layer), 100 nM SCS per layer, 250 nM fluorescent reporter substrate. Concentrations for FIG. 6C: 100 nM layer 1 DNAzyme, 75 nM layer 2 DNAzyme, 50 nM layer 3 DNAzyme, 25 nM layer 4 DNAzyme, 25% excess inhibitor and equimolar SCS per layer relative to DNAzyme concentration, 250 nM fluorescent reporter substrate. Pre-annealed DNAzyme-inhibitor complexes were added to buffer first, then pre-annealed SCS molecules, then fluorescent reporter substrate. Input (active DNAzyme in the top layer) was added last to initiate the reaction. Loss of FRET was observed over two hours. Each trace was baseline-corrected by subtracting the initial value for that trace from each time point in that trace, ensuring that each trace was plotting starting from zero fluorescence.

Protocol for Demonstrations of SCS Input-Output Combinations (FIG. 7A-C)

Sequences are listed in Tables 7-9 (FIGS. 29-31). Concentrations: (a) 100 nM DNAzymes (upstream & downstream), 125 nM inhibitor (upstream & downstream), 100 nM SCS, 50 nM reporter substrate, 100 nM input 1, 100 nM input 2. (b) 100 nM DNAzymes (upstream & downstream), 125 nM inhibitor (upstream), 100 nM SCS, 50 nM reporter substrate, 100 nM input. (c) 100 nM DNAzyme (upstream), 125 DNAzyme inhibitor (upstream), 100 nM SCS, 100 nM input, 100 nM fluorescent reporter strand, 125 nM downstream inhibitor labeled with quencher. Inhibited DNAzymes (either pre-annealed DNAzyme-inhibitor complexes or annealed loop-inhibited DNAzyme strands) were added to buffer first, then pre-annealed SCS molecules, then inputs. The system was incubated for 2 hours at room temperature, then the reporter (either a fluorescent reporter substrate or a strand displacement reporter complex) was added, and the endpoint fluorescence value was observed after a further 30 minutes incubation at room temperature. Each endpoint fluorescence value was baseline-corrected relative to the corresponding fluorescence value at substrate addition.

Protocol for Two-Layer Cascade Experiment in DNA Background (FIG. 8)

Sequences are listed in Table 6 (FIG. 28). Concentrations: 100 nM DNAzyme (layers 1 and 2), 125 nM inhibitor (layer 1), 100 nM SCS (SCS$_2$), 50 nM fluorescent reporter substrate (layer 1). Herring sperm DNA (Promega, Madison, Wis.) was annealed (as described above) and various amounts were added to 96 well plates containing buffer. Pre-annealed downstream DNAzyme-inhibitor complexes were added first, then pre-annealed SCS molecules, then fluorescent reporter substrate. Input (active upstream DNAzyme) was added last to initiate the reaction. Loss of FRET was observed over 30 minutes. Each positive kinetic trace was baseline-corrected by subtracting each time point observed from a negative control (run in the same experimental conditions but no active upstream DNAzyme present) from the corresponding time point in each positive trace. None of the negative controls showed a significant increase in fluorescence.

Figure 9:
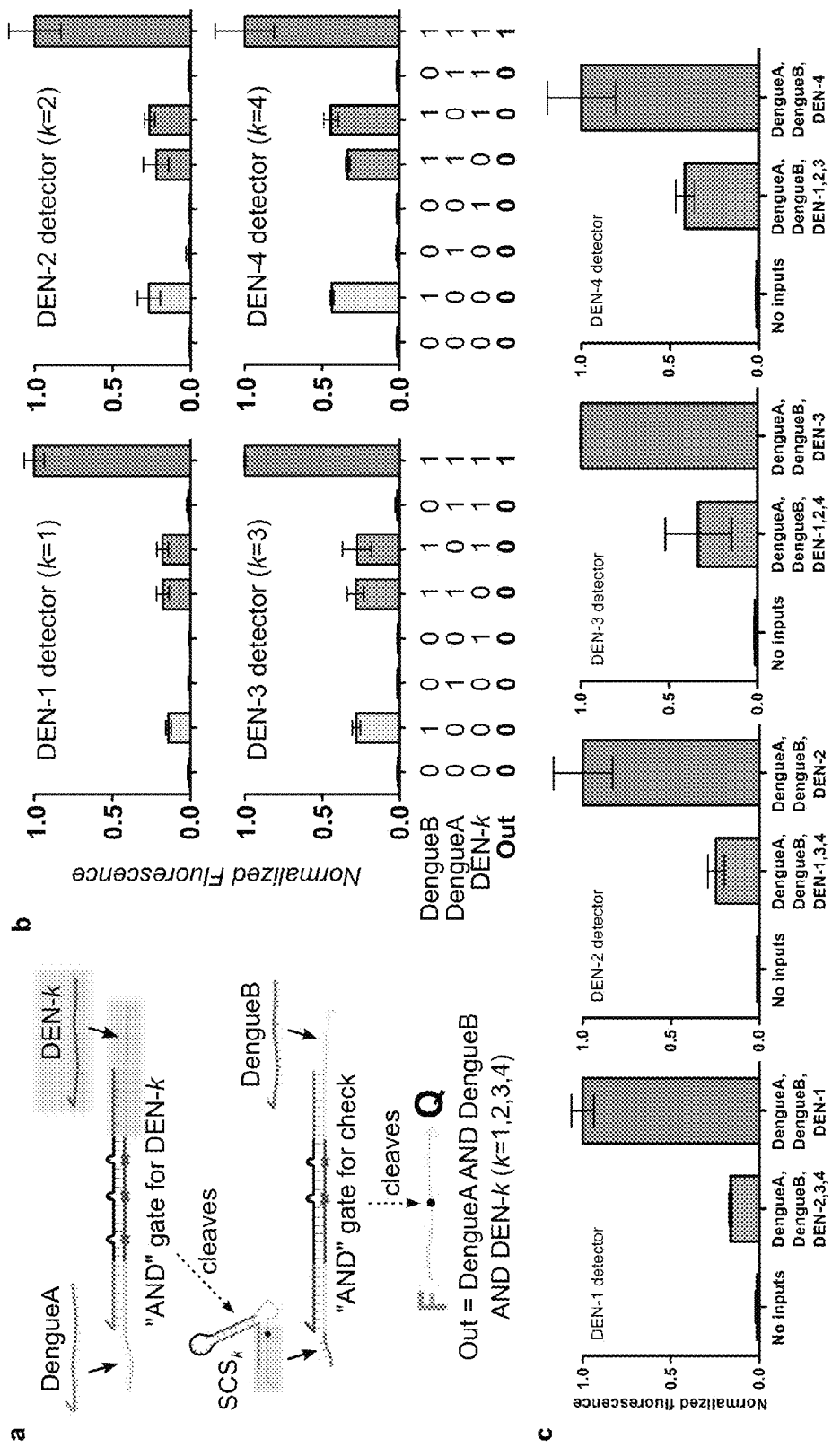
FIG. 9. Example application of the SCS in a multi-layer diagnostic logic circuit. a) Design of multi-layer diagnostic logic circuits for detection of sequences from the genomes of all four dengue serotypes. The circuit template for serotype DEN-k (k=1, 2, 3, 4) requires the presence of two conserved sequences from the dengue viral genome (DengueA and DengueB) and one sequence specific to the serotype of interest (DEN-k). This is implemented by DNAzyme displacement "AND" gates with mismatched inhibitors, which are connected by a SCS molecule. When both upstream inputs are present, the active upstream DNAzyme cleaves the SCS, producing an activator that serves as one input to the downstream gate. If the second input to the downstream gate is also present, the downstream DNAzyme is activated and we observe this via loss of FRET following substrate cleavage. The upstream "AND" gate uses the 3 mismatch design characterized in FIG. 4C, whereas the downstream gate uses an asymmetric pattern of mismatches because the activator produced by the SCS can displace into the catalytic core. We derived detection circuits for all four dengue serotypes (DEN1-4) by modifying only the domains highlighted in yellow. b) Demonstrations of serotyping circuits for DEN1-4, which show correct operation of all four instantiations of the three-input "AND" circuit template. Each serotyping circuit was characterized using all eight combinations of the two conserved sequences and the correct serotype-specific sequence. Variations in the normalized fluorescence levels (i.e., different levels of activation and leakage) may be attributed to variations in the stability of the corresponding $SCS_k$ structure in each case. Error bars represent the 95% confidence interval from three replicate experiments. c) Demonstration of serotype-specific response from dengue serotyping circuits. In each case, the negative control (grey) is the response in the absence of all three inputs, and the positive control (green) is the response in the presence of the two conserved inputs and the correct serotype-specific input (DEN-1, DEN-2, DEN-3 or DEN-4). The orange bar is the response in the presence of the two conserved inputs and all three incorrect serotype-specific sequences. In all cases, we observe a significantly reduced response when the incorrect serotype-specific sequences are present. In fact, the magnitudes of the non-specific responses to the incorrect serotype-sequences correlate with the background activations observed in the presence of the downstream DengueB input sequence, so it is likely that the non-specific activation seen in the presence of the incorrect serotype-specific sequences is in fact largely caused by the presence of DengueB. Hence we conclude that our four dengue detection circuits are in fact serotype-specific. Error bars represent the 95% confidence interval from three replicate experiments.

Protocol for Two-Layer Dengue Serotyping Circuits (FIG. 9)

Sequences for FIG. 9 are listed in Table 10 (FIG. 32). Concentrations: 100 nM DNAzyme (upstream & downstream), 125 nM inhibitor (upstream & downstream), 100 nM inputs (DengueA, DengueB, DEN-k for k=1, 2, 3, 4 as appropriate), 250 nM fluorescent reporter substrate. In FIG. 9C, experiments using multiple serotype-specific input strands were run using 100 nM of each serotype-specific input. Pre-annealed DNAzyme-inhibitor complexes were added to buffer first, then pre-annealed SCS molecules, then inputs. The system was incubated at room temperature for 2 hours, then fluorescent reporter substrate was added, and the endpoint fluorescence value was observed after incubation at room temperature for a further 6 hours. All endpoint fluorescence values were baseline-corrected relative to the corresponding fluorescence value at the time of substrate addition. The baseline-corrected fluorescence values were normalized to the endpoint fluorescence of the positive trace, so that values between 0 and 1 could be reported.

Example 3—Characterization of Modular DNAzyme Gates for Biosensing Applications

Materials

All oligonucleotides were purchased from Integrated DNA Technologies (Coralville, Iowa). Substrate molecules (DNA-RNA chimeras) were purified by RNase-free HPLC by the manufacturer. Sequences for all oligonucleotides used in these experiments are presented in Table 11 (FIG. 33).

Gate Preparation

DNAzymes and inhibitors were heated together at 95° C. for three minutes on a heat block, and subsequently annealed by cooling to room temperature over a minimum of 90 minutes. An excess of inhibitor was typically used to ensure complete inhibition and the resulting solution (including free inhibitor) was used without further purification.

Assay Conditions and Instrumentation

All assays were performed at room temperature (23° C.) in a buffer of 1M NaCl, 50 mM HEPES, 1 mM ZnCl$_2$, pH 7.0. Fluorescence was read on a Spectramax M2e fluorescent plate reader (Molecular Devices, Sunnyvale, Calif.) in a 200 μL reaction volume (492 nm excitation, 518 nm emission).

Example 4—Preliminary SCS Molecule Designs

Tables 12-20 (FIG. 11C) show sequences and concentrations for each variant of SCS Design 1 for DNAzyme cascades. The variant used in FIG. 11A is italicized in Table 16.

Tables 21-22 (FIG. 12C) depicts oligonucleotide sequences and concentrations for each variant of SCS Design 2 for DNAzyme cascades. The variant used in FIG. 12A is italicized in Table 21.

Table 23 (FIG. 13C) depicts oligonucleotide sequences and concentrations for SCS Design 3 for DNAzyme cascades in FIG. 13A.

Table 24 (FIG. 14C) depicts oligonucleotide sequences and concentrations for SCS Design 4 for DNAzyme cascades in FIG. 14A.

Table 25 (FIG. 14C) depicts proposed variants of the SCS Design 4, testing various properties to observe their contribution to stability and activation. Bold bases were targeted for variation, as described by the strand name. This is an example of the granularity of the rational design process. Here, M2 indicates the mutation of two bases, either on the 3' end or the 5' end of the activator. The corresponding sequences for each of these SCS Design 4 variants are found in Table 24. These sequences were not explicitly tested but such targeted locations for optimization were used in later variants.

Tables 26-27 (FIG. 15C) show oligonucleotide sequences and concentrations for each variant of SCS Design 5 for DNAzyme cascades. The variant used in FIG. 15A is italicized in Table 26.

Table 28 (FIG. 16C) shows oligonucleotide sequences and concentrations for SCS Design 6 for DNAzyme cascades in FIG. 16A.

Tables 29-32 (FIG. 17C) shows oligonucleotide sequences and concentrations for each variant of SCS Design 7 for DNAzyme cascades. The variant used in FIG. 17A is italicized.

Tables 33-36 (FIG. 18D) depicts oligonucleotide sequences and concentrations for each variant of SCS Design 8 for DNAzyme cascades. The variant used in FIG. 18A is italicized. Manual adjustments were made between the original variant (D8v1) and the final variant (v4).

Typically, 60 μL of DNAzyme and 75 μL inhibitor (25% excess inhibitor) of 2.5 μM working stock solutions were added together and heated together at 95° C. for three minutes on a heat block, and subsequently annealed by cooling to room temperature over a minimum of 90 minutes. All other strands that required an initially hybridized state, including all SCS and ACT molecules, were also annealed using the same protocol.

All assays were performed at room temperature (23° C.) in a buffer of 1M NaCl, 50 mM HEPES, 1 mM $ZnCl_2$, pH 7.0. Order of strand addition was as follows: Substrate, Dz/INH, SCS or ACT, depending on the experiment. Upstream DNAzyme (UE) was added last to SCS designs with an RNA cleavage site. Fluorescence was read on either a Spectramax M2e fluorescent plate reader (Molecular Devices, Sunnyvale, Calif.) in a 200 μL reaction volume or Quantamaster 40 fluorimeter (PTI, Binghamton, N.J.) in a 300 μL reaction volume. Fluorescence was monitored at 492 nm excitation and 518 nm emission wavelengths.

Example 5—Plasmid Extraction and Denaturation Protocol

Figure 25:
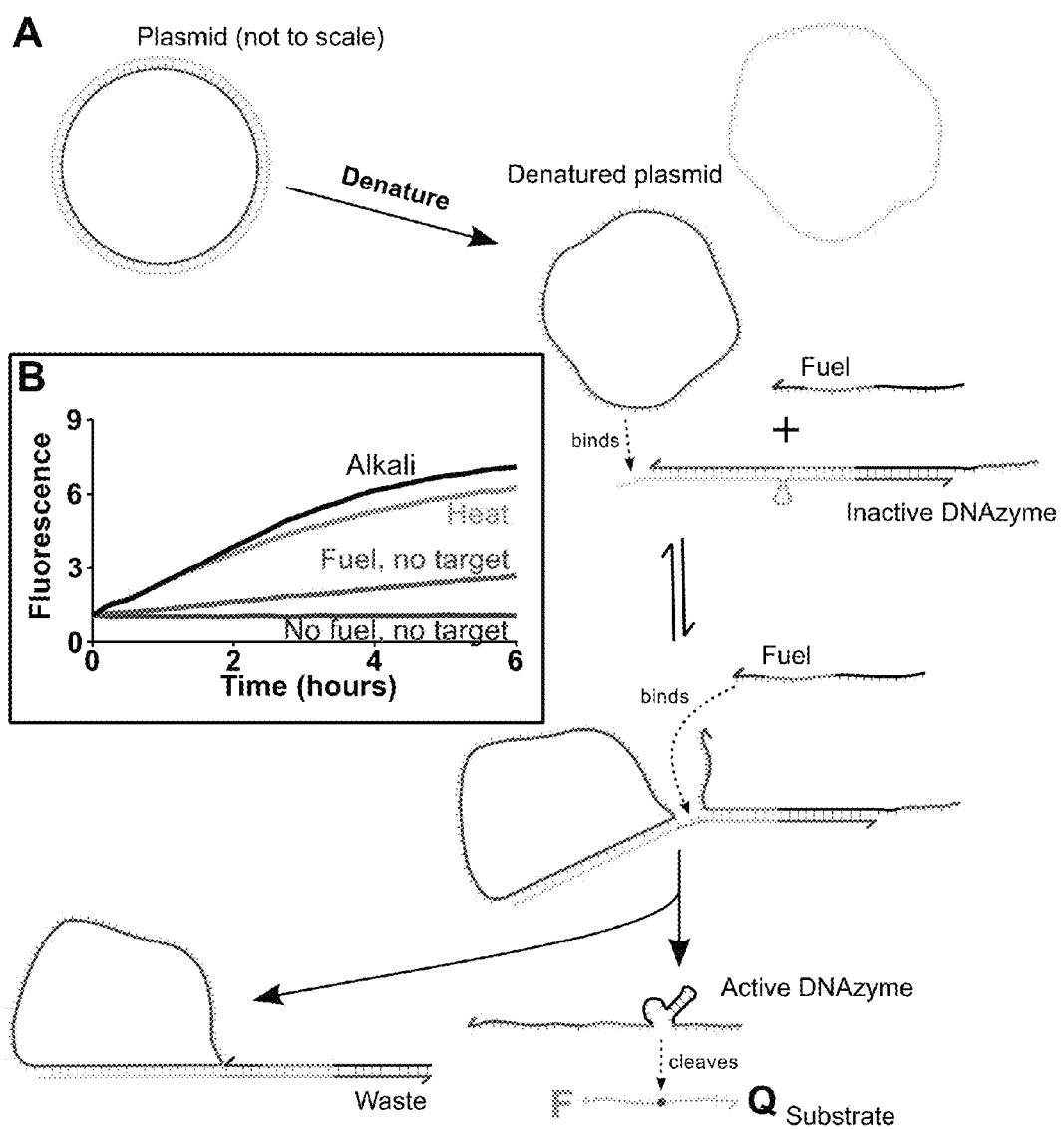
FIG. 25. Detection of double-stranded plasmid DNA using a modular DNAzyme biosensor gate. (A) Schematic of detection protocol for plasmid DNA. After the plasmid is extracted, it is denatured either by pH cycling (an isothermal treatment involving addition of a strong alkali to denature the double helix of the plasmid, followed by addition of a strong acid to bring the pH down to conditions in which the DNAzyme logic gate can operate) or by thermal denaturation (heating to denature the plasmid followed by rapid cooling). This produces two complementary circular ssDNA strands that are slow to reform into the double-stranded conformation due to the kinetic and thermodynamic barriers to refolding such a large double-stranded complex. A DNAzyme logic gate whose detection domain is targeted against part of the sequence of one of the plasmid strands is added. Binding of the plasmid to the target detection domain of the DNAzyme logic gate displaces the stem in the detection domain as before, opening up the secondary toehold to enable the fuel strand to bind. Fuel binding initiates a strand displacement reaction that releases a catalytically active DNAzyme, which proceeds to cleave a fluorescently-labeled substrate. (B) Results of plasmid detection assays using a modular DNAzyme biosensor gate. We observe the highest response in the presence of denatured plasmid: both chemically and thermally denatured plasmids gave similar responses.

Although this protocol relates to the preparation of a single plasmid sequence, as shown in FIG. 25, the protocol is generally useful for preparation of any dsDNA, including other plasmids or genomic DNA such as that found in STEC.

pRSET emGFP (Life Technologies, Grand Island, N.Y.) was transformed into SCS110 cells (Agilent Technologies, Santa Clara, Calif.). Cells were thawed on ice for roughly 30 minutes until liquid. One ng plasmid DNA was added to 100 μL cells, and incubated on ice for 30 minutes. Cells were then heat-shocked at 42° C. for 45 seconds, and placed back on ice for two minutes. Cells were then incubated at 37° C. for 10 minutes. After incubation, 20 μL cells were pipetted onto LB plates containing 50 μg/mL carbenicillin (Sigma-Aldrich, St. Louis, Mo.) and incubated overnight at 37° C.

Individual colonies were selected and grown in a 5 mL starter culture containing LB media+50 μg/mL carbenicillin. After an overnight incubation, cells were added to 250 mL LB+50 μg/mL carbenicillin and grown overnight. After incubation, cells were pelleted by centrifugation at 20,000×g and lysed using a Maxiprep kit (Qiagen, Venlo, Limburg, Netherlands). Pelleted DNA was resuspended in RNAse free water. To denature the plasmid, 20 μL 1M NaOH was added to 90 μL plasmid DNA in RNAse free water. After 10 minutes, 20 μL 1M HCl was added to the solution to bring the pH back down. Plasmid added to wells with DNAzyme gates comprised a maximum of 10% of the total volume.

Example 6—Biodetection Protocol

The first step in biodetection protocols is to extract the nucleic acids for analysis, using any of the commercially available kits (e.g., the Blood and Cell Culture Kit from Qiagen). In the case of single-stranded viral RNA detection targets such as flaviviruses, this may involve a chaotropic agent such as urea or guanidinium chloride to denature the viral capsids and destabilize any RNA secondary structure. In the case of double-stranded DNA, e.g. from bacterial genomes or plasmids, this may involve thermal or pH cycling to denature the duplexes. Once these targets are in single-stranded form, they may be detected by our gate technology.

Once the sample has been prepared, we prepare the components of the logic circuit. DNAzyme-inhibitor complexes may be prepared by annealing the desired quantity of DNAzyme with a ~25% excess of inhibitor, in the presence of streptavidin-coated magnetic beads functionalized with a biotinylated capture strand complementary to the inhibitor strand. Following the annealing step, a magnetic stand can be used to remove the beads from the solution, producing a solution of purified DNAzyme-inhibitor complexes with equimolar stoichiometry. Any SCS molecules needed for inter-DNAzyme signaling can be prepared by annealing the single strands in isolation The complete disclosure of all patents, patent applications, and publications, and electronically available material (including, for instance, nucleotide sequence submissions in, e.g., GenBank and RefSeq, and amino acid sequence submissions in, e.g., SwissProt, PR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for detecting a pathogen, the method comprising:
   providing a sample that is suspected to contain the pathogen;
   providing a structured chimeric substrate (SCS) polynucleotide having:
      at least one binding site which binds at least one target sequence;
      at least one protected cleavage site; and
      at least one protected effector sequence;
   wherein binding of a target sequence by the binding site is indicative of the presence of the pathogen in the sample;
   wherein binding of the target sequence to the binding site thermodynamically alters the SCS polynucleotide, thereby making at least one previously protected cleavage site accessible;
   wherein cleaving the SCS polynucleotide at the cleavage site made newly accessibly by the binding of the target sequence; further alters the thermodynamic stability of the SCS polynucleotide making at least one previously protected effector sequence accessible, wherein accessibility of the effector sequence results in the output of one or more downstream signals; exposing the sample to the SCS polynucleotide; and
   detecting at least one of the one or more of the downstream signals.

2. The method of claim 1 wherein at least one of the one or more downstream signals comprises the target sequence.

3. The method of claim 1 wherein at least one of the one or more downstream signals that is detected is a reporter molecule that does not comprise the target sequence.

4. The method of claim 1 wherein at least one of the target sequences is a sequence from the pathogen's genome.

5. The method of claim 1 wherein at least one of the target sequences is from a byproduct of the presence of the pathogen in the sample.

6. The method of claim 1 further comprising multiple SCS polynucleotides having multiple, different binding sites which bind multiple target sequences.

7. The method of claim 6 wherein the multiple target sequences are from different pathogens.

8. The method of claim 1 wherein the pathogen is bacteria.

9. The method of claim 8 wherein the pathogen is *E. coli*.

10. The method of claim 9 wherein the pathogen is Shiga toxin-bearing *E. coli*.

11. The method of claim 1 wherein the pathogen is a virus.

12. The method of claim 11 wherein the virus is a flavivirus.

13. The method of claim 12 wherein the flavivirus is selected from the group consisting of: dengue, West Nile, and St. Louis encephalitis.

14. The method of claim 1 further comprising exposing the sample to a second SCS polynucleotide having at least one binding site which binds at least one of the downstream signals;
   wherein binding of the downstream signal to the binding site of the second SCS polynucleotide thermodynamically alters the SCS polynucleotide resulting in one or more cleavage events; and
   wherein the one or more cleavage events alters the thermodynamic stability of the SCS polynucleotide resulting in the output of one or more downstream signals, which may be identical to or different from the downstream signal that bound to the second SCS polynucleotide.

15. The method of claim 14 wherein the downstream signal comprises a detectable label.

16. The method of claim 1 wherein the downstream signal comprises a sequence that is able to bind a DNA logic gate.

17. The method of claim 16 wherein the logic gate comprises a full DNAzyme, a multi-component self-assembling DNAzyme, a strand displacement gate, an aptamer, an aptazyme, or a hairpin assembly gate.

18. The method of claim 1 wherein the SCS has an initial conformation; at least one protected cleavage site is protected by the initial conformation of the SCS; and
   binding of the target sequence to the SCS causes a first conformational change that exposes at least one cleavage site.

19. The method of claim 18 wherein the at least one protected effector sequence is protected by the initial conformation and remains protected after the first conformational change; and
   wherein cleavage of the exposed cleavage site causes a second conformational change that exposes the effector sequence.

* * * * *